United States Patent
White et al.

(10) Patent No.: US 11,801,070 B2
(45) Date of Patent: *Oct. 31, 2023

(54) SURGICAL ACCESS PORT STABILIZATION

(71) Applicant: Medos International Sarl, Le Locle (CH)

(72) Inventors: Michael White, Liestal (CH); Stephane Gully, Rixheim (FR); Jan Klett, Aesch (CH); Peter Senn, Waldenburg (CH); Joern Richter, Kandern (DE)

(73) Assignee: Medos International Sarl, Le Locle (CH)

( * ) Notice: Subject to any disclaimer, the term of this patent is extended or adjusted under 35 U.S.C. 154(b) by 494 days.

This patent is subject to a terminal disclaimer.

(21) Appl. No.: 15/931,839

(22) Filed: May 14, 2020

(65) Prior Publication Data

US 2020/0268368 A1  Aug. 27, 2020

Related U.S. Application Data

(63) Continuation of application No. 15/786,891, filed on Oct. 18, 2017, now Pat. No. 10,682,130, which is a
(Continued)

(51) Int. Cl.
  *A61B 17/34* (2006.01)
  *A61B 90/00* (2016.01)
  (Continued)

(52) U.S. Cl.
  CPC ...... *A61B 17/3421* (2013.01); *A61B 1/00045* (2013.01); *A61B 1/00089* (2013.01);
  (Continued)

(58) Field of Classification Search
  CPC ....... A61B 17/02; A61B 17/025; A61B 17/34; A61B 17/3439; A61B 90/00
  See application file for complete search history.

(56) References Cited

U.S. PATENT DOCUMENTS

| 4,132,227 A | 1/1979 | Ibe |
| 4,318,401 A | 3/1982 | Zimmerman |

(Continued)

FOREIGN PATENT DOCUMENTS

| CN | 2659368 Y | 12/2004 |
| CN | 1735380 A | 2/2006 |

(Continued)

OTHER PUBLICATIONS

Chinese Office Action for Application No. 201880013056.7, dated Oct. 26, 2021 (6 Pages).
(Continued)

*Primary Examiner* — Christopher J Beccia
(74) *Attorney, Agent, or Firm* — Barnes & Thornburg LLP

(57) ABSTRACT

Surgical access port stabilization systems and methods are described herein. Such systems and methods can be employed to provide ipsilateral stabilization of a surgical access port, e.g., during spinal surgeries. In one embodiment, a surgical system can include an access port configured for percutaneous insertion into a patient to define a channel to a surgical site and an anchor configured for insertion into the patient's bone. Further, the access port can be coupled to the anchor such that a longitudinal axis of the access port and a longitudinal axis of the anchor are non-coaxial. With such a system, a surgeon or other user can access a surgical site through the access port without the need for external or other stabilization of the access port, but can instead position the access port relative to an anchor already placed in the patient's body.

18 Claims, 33 Drawing Sheets

Related U.S. Application Data continuation-in-part of application No. 15/437,792, filed on Feb. 21, 2017, now Pat. No. 10,874,425, which is a continuation-in-part of application No. 15/254,877, filed on Sep. 1, 2016, now Pat. No. 10,987,129.

(60) Provisional application No. 62/468,475, filed on Mar. 8, 2017, provisional application No. 62/214,297, filed on Sep. 4, 2015.

(51) Int. Cl.

| | | |
|---|---|---|
| *A61B 90/50* | (2016.01) | |
| *A61B 90/57* | (2016.01) | |
| *A61B 1/00* | (2006.01) | |
| *A61B 1/012* | (2006.01) | |
| *A61B 1/018* | (2006.01) | |
| *A61B 1/05* | (2006.01) | |
| *A61B 1/055* | (2006.01) | |
| *A61B 1/07* | (2006.01) | |
| *A61B 1/12* | (2006.01) | |
| *A61B 1/233* | (2006.01) | |
| *A61B 1/267* | (2006.01) | |
| *A61B 1/313* | (2006.01) | |
| *A61B 1/317* | (2006.01) | |
| *A61B 1/32* | (2006.01) | |
| *A61B 5/06* | (2006.01) | |
| *A61B 5/00* | (2006.01) | |
| *A61B 17/00* | (2006.01) | |
| *A61B 17/02* | (2006.01) | |
| *A61B 17/32* | (2006.01) | |
| *A61B 17/60* | (2006.01) | |
| *A61B 17/70* | (2006.01) | |
| *A61B 18/18* | (2006.01) | |
| *A61F 2/44* | (2006.01) | |
| *A61F 2/46* | (2006.01) | |
| *A61B 5/24* | (2021.01) | |
| *A61B 34/20* | (2016.01) | |
| *A61B 34/00* | (2016.01) | |
| *A61B 90/30* | (2016.01) | |
| *A61B 17/16* | (2006.01) | |
| *A61B 17/17* | (2006.01) | |
| *A61B 17/56* | (2006.01) | |
| *A61B 18/00* | (2006.01) | |
| *A61B 34/30* | (2016.01) | |

(52) U.S. Cl.
CPC ...... *A61B 1/00091* (2013.01); *A61B 1/00094* (2013.01); *A61B 1/00096* (2013.01); *A61B 1/00103* (2013.01); *A61B 1/00128* (2013.01); *A61B 1/00133* (2013.01); *A61B 1/00135* (2013.01); *A61B 1/00154* (2013.01); *A61B 1/012* (2013.01); *A61B 1/018* (2013.01); *A61B 1/05* (2013.01); *A61B 1/051* (2013.01); *A61B 1/055* (2013.01); *A61B 1/07* (2013.01); *A61B 1/126* (2013.01); *A61B 1/233* (2013.01); *A61B 1/2676* (2013.01); *A61B 1/317* (2013.01); *A61B 1/3132* (2013.01); *A61B 1/3135* (2013.01); *A61B 1/32* (2013.01); *A61B 5/068* (2013.01); *A61B 5/24* (2021.01); *A61B 5/407* (2013.01); *A61B 5/4041* (2013.01); *A61B 17/00234* (2013.01); *A61B 17/025* (2013.01); *A61B 17/0218* (2013.01); *A61B 17/0293* (2013.01); *A61B 17/320068* (2013.01); *A61B 17/3423* (2013.01); *A61B 17/3462* (2013.01); *A61B 17/60* (2013.01); *A61B 17/708* (2013.01); *A61B 17/7032* (2013.01); *A61B 17/7074* (2013.01); *A61B 18/1815* (2013.01); *A61B 90/03* (2016.02); *A61B 90/361* (2016.02); *A61B 90/50* (2016.02); *A61B 90/57* (2016.02); *A61F 2/4455* (2013.01); *A61F 2/4611* (2013.01); *A61B 1/00149* (2013.01); *A61B 17/0206* (2013.01); *A61B 17/1637* (2013.01); *A61B 17/1671* (2013.01); *A61B 17/1703* (2013.01); *A61B 17/1757* (2013.01); *A61B 17/3403* (2013.01); *A61B 17/3439* (2013.01); *A61B 17/70* (2013.01); *A61B 17/7083* (2013.01); *A61B 34/30* (2016.02); *A61B 34/70* (2016.02); *A61B 90/30* (2016.02); *A61B 2017/0034* (2013.01); *A61B 2017/00261* (2013.01); *A61B 2017/00314* (2013.01); *A61B 2017/00345* (2013.01); *A61B 2017/00407* (2013.01); *A61B 2017/00477* (2013.01); *A61B 2017/00557* (2013.01); *A61B 2017/00738* (2013.01); *A61B 2017/00831* (2013.01); *A61B 2017/00858* (2013.01); *A61B 2017/00871* (2013.01); *A61B 2017/00946* (2013.01); *A61B 2017/00991* (2013.01); *A61B 2017/0256* (2013.01); *A61B 2017/0262* (2013.01); *A61B 2017/320075* (2017.08); *A61B 2017/345* (2013.01); *A61B 2017/347* (2013.01); *A61B 2017/3443* (2013.01); *A61B 2017/3445* (2013.01); *A61B 2017/3447* (2013.01); *A61B 2017/3454* (2013.01); *A61B 2017/3484* (2013.01); *A61B 2017/564* (2013.01); *A61B 2018/00339* (2013.01); *A61B 2018/00565* (2013.01); *A61B 2018/00577* (2013.01); *A61B 2018/1861* (2013.01); *A61B 2018/1869* (2013.01); *A61B 2034/2055* (2016.02); *A61B 2090/034* (2016.02); *A61B 2090/036* (2016.02); *A61B 2090/08021* (2016.02); *A61B 2090/306* (2016.02); *A61B 2090/371* (2016.02); *A61B 2090/3983* (2016.02); *A61B 2218/002* (2013.01); *A61B 2218/007* (2013.01); *A61F 2002/4635* (2013.01)

(56) References Cited

U.S. PATENT DOCUMENTS

| | | |
|---|---|---|
| 4,573,448 A | 3/1986 | Kambin |
| 4,646,738 A | 3/1987 | Trott |
| 4,678,459 A | 7/1987 | Onik et al. |
| 4,807,593 A | 2/1989 | Ito |
| 4,863,430 A | 9/1989 | Klyce et al. |
| 4,874,375 A | 10/1989 | Ellison |
| 4,888,146 A | 12/1989 | Dandeneau |
| 5,080,662 A | 1/1992 | Paul |
| 5,195,541 A | 3/1993 | Obenchain |
| 5,207,213 A | 5/1993 | Auhll et al. |
| 5,285,795 A | 2/1994 | Ryan et al. |
| 5,395,317 A | 3/1995 | Kambin |
| 5,439,464 A | 8/1995 | Shapiro |
| 5,529,580 A | 6/1996 | Kusunoki et al. |
| 5,540,706 A | 7/1996 | Aust et al. |
| 5,569,290 A | 10/1996 | McAfee |
| 5,591,187 A | 1/1997 | Dekel |
| 5,601,569 A | 2/1997 | Pisharodi |
| 5,615,690 A | 4/1997 | Giurtino et al. |
| 5,618,293 A | 4/1997 | Sample et al. |
| 5,662,300 A | 9/1997 | Michelson |
| 5,688,222 A | 11/1997 | Hluchy et al. |
| 5,697,888 A | 12/1997 | Kobayashi et al. |
| 5,730,754 A | 3/1998 | Obenchain |
| 5,733,242 A | 3/1998 | Rayburn et al. |
| 5,735,792 A | 4/1998 | Vanden Hoek et al. |
| 5,749,602 A | 5/1998 | Delaney et al. |

(56) References Cited

U.S. PATENT DOCUMENTS

| | | | |
|---|---|---|---|
| 5,792,044 A | 8/1998 | Foley et al. | |
| 5,820,623 A | 10/1998 | Ng | |
| 5,885,300 A | 3/1999 | Tokuhashi et al. | |
| 5,894,369 A | 4/1999 | Akiba et al. | |
| 5,899,425 A | 5/1999 | Corey Jr et al. | |
| 5,928,137 A | 7/1999 | Green | |
| 5,954,635 A | 9/1999 | Foley et al. | |
| 5,976,075 A | 11/1999 | Beane et al. | |
| 5,989,183 A | 11/1999 | Reisdorf et al. | |
| 6,017,333 A | 1/2000 | Bailey | |
| 6,033,105 A | 3/2000 | Barker et al. | |
| 6,053,907 A | 4/2000 | Zirps | |
| 6,063,021 A | 5/2000 | Hossain et al. | |
| 6,110,182 A | 8/2000 | Mowlai-Ashtiani | |
| 6,126,592 A | 10/2000 | Proch et al. | |
| 6,139,563 A | 10/2000 | Cosgrove et al. | |
| 6,200,322 B1 | 3/2001 | Branch et al. | |
| 6,217,509 B1 | 4/2001 | Foley et al. | |
| 6,234,961 B1 | 5/2001 | Gray | |
| 6,283,966 B1 | 9/2001 | Houfburg | |
| 6,286,179 B1 | 9/2001 | Byrne | |
| 6,296,644 B1 | 10/2001 | Saurat et al. | |
| 6,322,498 B1 | 11/2001 | Gravenstein et al. | |
| 6,354,992 B1 | 3/2002 | Kato | |
| 6,357,710 B1 | 3/2002 | Fielden et al. | |
| 6,371,968 B1 | 4/2002 | Kogasaka et al. | |
| 6,383,191 B1 | 5/2002 | Zdeblick et al. | |
| 6,447,446 B1 | 9/2002 | Smith et al. | |
| 6,468,289 B1 | 10/2002 | Bonutti | |
| 6,520,495 B1 | 2/2003 | La Mendola | |
| 6,558,407 B1 | 5/2003 | Ivanko et al. | |
| 6,575,899 B1 | 6/2003 | Foley et al. | |
| 6,579,281 B2 | 6/2003 | Palmer et al. | |
| 6,596,008 B1 | 7/2003 | Kambin | |
| 6,626,830 B1 | 9/2003 | Califiore et al. | |
| 6,648,915 B2 | 11/2003 | Sazy | |
| 6,663,563 B1 * | 12/2003 | Sharratt | A61B 1/00149 600/227 |
| 6,676,597 B2 | 1/2004 | Guenst et al. | |
| 6,679,833 B2 | 1/2004 | Smith et al. | |
| 6,685,724 B1 | 2/2004 | Haluck | |
| 6,688,564 B2 | 2/2004 | Salvermoser et al. | |
| 6,758,809 B2 | 7/2004 | Briscoe et al. | |
| 6,808,505 B2 | 10/2004 | Kadan | |
| 6,887,198 B2 | 5/2005 | Phillips et al. | |
| 6,983,930 B1 | 1/2006 | La Mendola et al. | |
| 7,001,342 B2 | 2/2006 | Faciszewski | |
| 7,087,058 B2 | 8/2006 | Cragg | |
| 7,104,986 B2 | 9/2006 | Hovda et al. | |
| 7,137,949 B2 | 11/2006 | Scirica et al. | |
| 7,179,261 B2 | 2/2007 | Sicvol et al. | |
| 7,182,731 B2 | 2/2007 | Nguyen et al. | |
| 7,226,413 B2 | 6/2007 | McKinley | |
| 7,341,556 B2 | 3/2008 | Shalman | |
| 7,434,325 B2 | 10/2008 | Foley et al. | |
| 7,491,168 B2 | 2/2009 | Raymond et al. | |
| 7,591,790 B2 | 9/2009 | Pflueger | |
| 7,594,888 B2 | 9/2009 | Raymond et al. | |
| 7,618,431 B2 | 11/2009 | Roehm, III et al. | |
| 7,636,596 B2 | 12/2009 | Solar | |
| 7,637,905 B2 | 12/2009 | Saadat et al. | |
| 7,641,659 B2 | 1/2010 | Emstad et al. | |
| 7,766,313 B2 | 8/2010 | Panosian | |
| 7,771,384 B2 | 8/2010 | Ravo | |
| 7,794,456 B2 | 9/2010 | Sharps et al. | |
| 7,794,469 B2 | 9/2010 | Kao et al. | |
| 7,811,303 B2 | 10/2010 | Fallin et al. | |
| 7,931,579 B2 | 4/2011 | Bertolero et al. | |
| 7,946,981 B1 | 5/2011 | Cubb | |
| 7,951,141 B2 | 5/2011 | Sharps et al. | |
| 7,959,564 B2 | 6/2011 | Ritland | |
| 7,988,623 B2 | 8/2011 | Pagliuca et al. | |
| 8,007,492 B2 | 8/2011 | DiPoto et al. | |
| 8,038,606 B2 | 10/2011 | Otawara | |
| 8,043,381 B2 | 10/2011 | Hestad et al. | |
| 8,062,218 B2 | 11/2011 | Sebastian et al. | |
| 8,079,952 B2 | 12/2011 | Fujimoto | |
| 8,092,464 B2 | 1/2012 | McKay | |
| 8,096,944 B2 | 1/2012 | Harrel | |
| 8,202,216 B2 | 6/2012 | Melkent et al. | |
| 8,206,357 B2 | 6/2012 | Bettuchi | |
| 8,230,863 B2 | 7/2012 | Ravikumar et al. | |
| 8,236,006 B2 | 8/2012 | Hamada | |
| 8,267,896 B2 | 9/2012 | Hartoumbekis et al. | |
| 8,303,492 B2 | 11/2012 | Ito | |
| 8,333,690 B2 | 12/2012 | Ikeda | |
| 8,360,970 B2 | 1/2013 | Mangiardi | |
| 8,372,131 B2 | 2/2013 | Hestad et al. | |
| 8,382,048 B2 | 2/2013 | Nesper et al. | |
| 8,397,335 B2 | 3/2013 | Gordin et al. | |
| 8,419,625 B2 | 4/2013 | Ito | |
| 8,435,174 B2 | 5/2013 | Cropper et al. | |
| 8,460,180 B1 | 6/2013 | Zarate et al. | |
| 8,460,186 B2 | 6/2013 | Ortiz et al. | |
| 8,460,310 B2 | 6/2013 | Stern | |
| 8,518,087 B2 | 8/2013 | Lopez et al. | |
| 8,535,220 B2 | 9/2013 | Mondschein | |
| 8,556,809 B2 | 10/2013 | Vijayanagar | |
| 8,585,726 B2 | 11/2013 | Yoon et al. | |
| 8,602,979 B2 | 12/2013 | Kitano | |
| 8,622,894 B2 | 1/2014 | Banik et al. | |
| 8,636,655 B1 | 1/2014 | Childs | |
| 8,648,932 B2 | 2/2014 | Talbert et al. | |
| 8,688,186 B1 | 4/2014 | Mao et al. | |
| 8,690,764 B2 | 4/2014 | Clark et al. | |
| 8,721,536 B2 | 5/2014 | Marino et al. | |
| 8,740,779 B2 | 6/2014 | Koshida | |
| 8,784,421 B2 | 7/2014 | Garrison et al. | |
| 8,821,378 B2 | 9/2014 | Morgenstern Lopez et al. | |
| 8,834,507 B2 | 9/2014 | Mire et al. | |
| 8,845,734 B2 | 9/2014 | Weiman | |
| 8,852,242 B2 | 10/2014 | Morgenstern Lopez et al. | |
| 8,870,753 B2 | 10/2014 | Boulais et al. | |
| 8,870,756 B2 | 10/2014 | Maurice | |
| 8,876,712 B2 | 11/2014 | Yee et al. | |
| 8,888,689 B2 | 11/2014 | Poll et al. | |
| 8,888,813 B2 | 11/2014 | To | |
| 8,894,573 B2 | 11/2014 | Loftus et al. | |
| 8,894,653 B2 | 11/2014 | Solsberg et al. | |
| 8,926,502 B2 | 1/2015 | Levy et al. | |
| 8,932,207 B2 | 1/2015 | Greenburg et al. | |
| 8,932,360 B2 | 1/2015 | Womble et al. | |
| 8,936,545 B2 | 1/2015 | To | |
| 8,936,605 B2 | 1/2015 | Greenberg | |
| 8,952,312 B2 | 2/2015 | Blanquart et al. | |
| 8,961,404 B2 | 2/2015 | Ito | |
| 8,972,714 B2 | 3/2015 | Talbert et al. | |
| 8,974,381 B1 | 3/2015 | Lovell et al. | |
| 8,986,199 B2 | 3/2015 | Weisenburgh, II et al. | |
| 8,992,580 B2 | 3/2015 | Bar et al. | |
| 9,028,522 B1 | 5/2015 | Prado | |
| 9,050,036 B2 | 6/2015 | Poll et al. | |
| 9,050,037 B2 | 6/2015 | Poll et al. | |
| 9,050,146 B2 | 6/2015 | Woolley et al. | |
| 9,055,936 B2 | 6/2015 | Mire et al. | |
| 9,072,431 B2 | 7/2015 | Adams et al. | |
| 9,078,562 B2 | 7/2015 | Poll et al. | |
| 9,123,602 B2 | 9/2015 | Blanquart | |
| 9,131,948 B2 | 9/2015 | Fang et al. | |
| 9,144,374 B2 | 9/2015 | Maurice, Jr. | |
| 9,153,609 B2 | 10/2015 | Blanquart | |
| 9,198,674 B2 | 12/2015 | Benson et al. | |
| 9,211,059 B2 | 12/2015 | Drach et al. | |
| 9,216,016 B2 | 12/2015 | Fiechter et al. | |
| 9,216,125 B2 | 12/2015 | Sklar | |
| 9,226,647 B2 | 1/2016 | Sugawara | |
| 9,232,935 B2 | 1/2016 | Brand et al. | |
| 9,247,997 B2 | 2/2016 | Stefanchik et al. | |
| 9,265,491 B2 | 2/2016 | Lins et al. | |
| 9,277,928 B2 | 3/2016 | Morgenstern Lopez | |
| 9,307,972 B2 | 4/2016 | Lovell et al. | |
| 9,320,419 B2 | 4/2016 | Kirma et al. | |
| RE46,007 E | 5/2016 | Banik et al. | |
| RE46,062 E | 7/2016 | James et al. | |

(56) References Cited

U.S. PATENT DOCUMENTS

| | | | |
|---|---|---|---|
| 9,386,971 B1 | 7/2016 | Casey et al. | |
| 9,387,313 B2 | 7/2016 | Culbert et al. | |
| 9,414,828 B2 | 8/2016 | Abidin et al. | |
| 9,462,234 B2 | 10/2016 | Blanquart et al. | |
| 9,486,296 B2 | 11/2016 | Mire et al. | |
| 9,492,194 B2 | 11/2016 | Morgenstern Lopez et al. | |
| 9,509,917 B2 | 11/2016 | Blanquart et al. | |
| 9,510,853 B2 | 12/2016 | Aljuri et al. | |
| 9,516,239 B2 | 12/2016 | Blanquart et al. | |
| 9,522,017 B2 | 12/2016 | Poll et al. | |
| 9,526,401 B2 | 12/2016 | Saadat et al. | |
| 9,579,012 B2 | 2/2017 | Vazales et al. | |
| 9,603,510 B2 | 3/2017 | Ammirati | |
| 9,603,610 B2 | 3/2017 | Richter et al. | |
| 9,610,007 B2 | 4/2017 | Kienzle et al. | |
| 9,610,095 B2 | 4/2017 | To | |
| 9,622,650 B2 | 4/2017 | Blanquart | |
| 9,629,521 B2 | 4/2017 | Ratnakar | |
| 9,641,815 B2 | 5/2017 | Richardson et al. | |
| 9,655,605 B2 | 5/2017 | Serowski et al. | |
| 9,655,639 B2 | 5/2017 | Mark | |
| 9,668,643 B2 | 6/2017 | Kennedy, II et al. | |
| 9,675,235 B2 | 6/2017 | Lieponis | |
| 9,700,378 B2 | 7/2017 | Mowlai-Ashtiani | |
| 9,706,905 B2 | 7/2017 | Levy | |
| 10,111,712 B2 * | 10/2018 | Chegini | A61B 17/3423 |
| 10,561,427 B2 | 2/2020 | Weitzman et al. | |
| 10,576,231 B2 | 3/2020 | Gunday et al. | |
| 10,682,130 B2 * | 6/2020 | White | A61B 90/57 |
| 10,758,220 B2 | 9/2020 | White et al. | |
| 10,869,659 B2 | 12/2020 | Thommen et al. | |
| 10,874,425 B2 | 12/2020 | Thommen et al. | |
| 10,987,129 B2 | 4/2021 | Thommen et al. | |
| 11,000,312 B2 | 5/2021 | Thommen et al. | |
| 11,331,090 B2 | 5/2022 | Thommen et al. | |
| 11,439,380 B2 | 9/2022 | Thommen et al. | |
| 11,559,328 B2 | 1/2023 | Richter et al. | |
| 2002/0022762 A1 | 2/2002 | Beane et al. | |
| 2002/0035313 A1 | 3/2002 | Scirica et al. | |
| 2002/0091390 A1 | 7/2002 | Michelson | |
| 2002/0138020 A1 | 9/2002 | Pflueger | |
| 2002/0165560 A1 | 11/2002 | Danitz et al. | |
| 2003/0083555 A1 | 5/2003 | Hunt et al. | |
| 2003/0083688 A1 | 5/2003 | Simonson | |
| 2003/0171744 A1 | 9/2003 | Leung et al. | |
| 2003/0191474 A1 | 10/2003 | Cragg et al. | |
| 2004/0092940 A1 | 5/2004 | Zwirnmann | |
| 2004/0122446 A1 | 6/2004 | Solar | |
| 2004/0127992 A1 | 7/2004 | Serhan et al. | |
| 2004/0143165 A1 | 7/2004 | Alleyne | |
| 2004/0158260 A1 | 8/2004 | Blau et al. | |
| 2004/0158286 A1 | 8/2004 | Roux et al. | |
| 2004/0249246 A1 | 12/2004 | Campos | |
| 2005/0021040 A1 | 1/2005 | Bertagnoli | |
| 2005/0075540 A1 | 4/2005 | Shluzas et al. | |
| 2005/0075644 A1 | 4/2005 | DiPoto et al. | |
| 2005/0080435 A1 | 4/2005 | Smith et al. | |
| 2005/0085692 A1 | 4/2005 | Kiehn et al. | |
| 2005/0090848 A1 | 4/2005 | Adams | |
| 2005/0107671 A1 | 5/2005 | McKinley | |
| 2005/0137461 A1 | 6/2005 | Marchek et al. | |
| 2005/0187570 A1 | 8/2005 | Nguyen et al. | |
| 2005/0192589 A1 | 9/2005 | Raymond et al. | |
| 2005/0256525 A1 | 11/2005 | Culbert et al. | |
| 2006/0020165 A1 | 1/2006 | Adams | |
| 2006/0041270 A1 | 2/2006 | Lenker et al. | |
| 2006/0052671 A1 | 3/2006 | McCarthy | |
| 2006/0074445 A1 | 4/2006 | Gerber et al. | |
| 2006/0142643 A1 | 6/2006 | Parker | |
| 2006/0161189 A1 | 7/2006 | Harp | |
| 2006/0173521 A1 | 8/2006 | Pond et al. | |
| 2006/0200186 A1 | 9/2006 | Marchek et al. | |
| 2006/0206118 A1 | 9/2006 | Kim et al. | |
| 2006/0264895 A1 | 11/2006 | Flanders | |
| 2007/0049794 A1 | 3/2007 | Glassenberg et al. | |
| 2007/0055259 A1 | 3/2007 | Norton et al. | |
| 2007/0129634 A1 | 6/2007 | Hickey et al. | |
| 2007/0149975 A1 | 6/2007 | Oliver et al. | |
| 2007/0162223 A1 | 7/2007 | Clark | |
| 2007/0203396 A1 | 8/2007 | McCutcheon et al. | |
| 2007/0213716 A1 | 9/2007 | Lenke et al. | |
| 2007/0225556 A1 | 9/2007 | Ortiz et al. | |
| 2007/0249899 A1 | 10/2007 | Seifert | |
| 2007/0255100 A1 | 11/2007 | Barlow et al. | |
| 2007/0260113 A1 | 11/2007 | Otawara | |
| 2007/0260120 A1 | 11/2007 | Otawara | |
| 2007/0260184 A1 | 11/2007 | Justis et al. | |
| 2007/0270866 A1 | 11/2007 | von Jako | |
| 2008/0015621 A1 | 1/2008 | Emanuel | |
| 2008/0033251 A1 | 2/2008 | Araghi | |
| 2008/0064921 A1 | 3/2008 | Larkin et al. | |
| 2008/0064928 A1 | 3/2008 | Otawara | |
| 2008/0081951 A1 | 4/2008 | Frasier et al. | |
| 2008/0139879 A1 | 6/2008 | Olson et al. | |
| 2008/0147109 A1 | 6/2008 | Kambin et al. | |
| 2008/0183189 A1 | 7/2008 | Teichman et al. | |
| 2008/0188714 A1 | 8/2008 | McCaffrey | |
| 2008/0242930 A1 | 10/2008 | Hanypsiak et al. | |
| 2008/0260342 A1 | 10/2008 | Kuroiwa | |
| 2009/0018566 A1 | 1/2009 | Escudero et al. | |
| 2009/0024158 A1 | 1/2009 | Viker | |
| 2009/0062871 A1 | 3/2009 | Chin et al. | |
| 2009/0105543 A1 | 4/2009 | Miller et al. | |
| 2009/0125032 A1 | 5/2009 | Gutierrez et al. | |
| 2009/0149857 A1 | 6/2009 | Culbert et al. | |
| 2009/0156898 A1 | 6/2009 | Ichimura | |
| 2009/0187080 A1 | 7/2009 | Seex | |
| 2009/0240111 A1 | 9/2009 | Kessler et al. | |
| 2009/0253964 A1 | 10/2009 | Miyamoto | |
| 2009/0253965 A1 | 10/2009 | Miyamoto | |
| 2009/0259184 A1 | 10/2009 | Okoniewski | |
| 2009/0264895 A1 | 10/2009 | Gasperut et al. | |
| 2009/0287061 A1 | 11/2009 | Feigenbaum et al. | |
| 2009/0318765 A1 | 12/2009 | Torii | |
| 2010/0004651 A1 | 1/2010 | Biyani | |
| 2010/0022841 A1 | 1/2010 | Takahashi et al. | |
| 2010/0076476 A1 | 3/2010 | To et al. | |
| 2010/0081875 A1 | 4/2010 | Fowler et al. | |
| 2010/0114147 A1 | 5/2010 | Biyani | |
| 2010/0151161 A1 | 6/2010 | Da Rolo | |
| 2010/0161060 A1 | 6/2010 | Schaller et al. | |
| 2010/0256446 A1 | 10/2010 | Raju | |
| 2010/0268241 A1 | 10/2010 | Flom et al. | |
| 2010/0280325 A1 | 11/2010 | Ibrahim et al. | |
| 2010/0284580 A1 | 11/2010 | OuYang et al. | |
| 2010/0286477 A1 | 11/2010 | OuYang et al. | |
| 2010/0312053 A1 | 12/2010 | Larsen | |
| 2010/0317928 A1 | 12/2010 | Subramaniam | |
| 2010/0324506 A1 | 12/2010 | Pellegrino et al. | |
| 2011/0009905 A1 | 1/2011 | Shluzas | |
| 2011/0028791 A1 | 2/2011 | Marino et al. | |
| 2011/0040333 A1 | 2/2011 | Simonson et al. | |
| 2011/0054507 A1 | 3/2011 | Batten et al. | |
| 2011/0056500 A1 | 3/2011 | Shin et al. | |
| 2011/0073594 A1 | 3/2011 | Bonn | |
| 2011/0098628 A1 | 4/2011 | Yeung et al. | |
| 2011/0106261 A1 | 5/2011 | Chin et al. | |
| 2011/0112588 A1 | 5/2011 | Linderman et al. | |
| 2011/0125158 A1 | 5/2011 | Diwan et al. | |
| 2011/0130634 A1 | 6/2011 | Solitario, Jr. et al. | |
| 2011/0201888 A1 | 8/2011 | Verner | |
| 2011/0230965 A1 | 9/2011 | Schell et al. | |
| 2011/0251597 A1 | 10/2011 | Bharadwaj et al. | |
| 2011/0257478 A1 | 10/2011 | Kleiner et al. | |
| 2011/0295070 A1 | 12/2011 | Yasunaga | |
| 2011/0319941 A1 | 12/2011 | Bar et al. | |
| 2012/0016192 A1 | 1/2012 | Jansen et al. | |
| 2012/0029412 A1 | 2/2012 | Yeung et al. | |
| 2012/0095296 A1 | 4/2012 | Trieu et al. | |
| 2012/0101338 A1 | 4/2012 | O'Prey et al. | |
| 2012/0111682 A1 | 5/2012 | Andre | |
| 2012/0116170 A1 | 5/2012 | Vayser et al. | |
| 2012/0157788 A1 | 6/2012 | Serowski et al. | |
| 2012/0172664 A1 | 7/2012 | Hayman et al. | |

(56) References Cited

U.S. PATENT DOCUMENTS

| | | |
|---|---|---|
| 2012/0209273 A1 | 8/2012 | Zaretzka et al. |
| 2012/0221007 A1 | 8/2012 | Batten et al. |
| 2012/0232350 A1 | 9/2012 | Seex |
| 2012/0232552 A1 | 9/2012 | Morgenstern Lopez et al. |
| 2012/0259173 A1 | 10/2012 | Waldron et al. |
| 2012/0265022 A1 | 10/2012 | Menn |
| 2012/0296171 A1 | 11/2012 | Lovell et al. |
| 2012/0298820 A1 | 11/2012 | Manolidis |
| 2012/0316400 A1 | 12/2012 | Vijayanagar |
| 2012/0323080 A1 | 12/2012 | DeRidder et al. |
| 2013/0030535 A1 | 1/2013 | Foley et al. |
| 2013/0103067 A1 | 4/2013 | Fabro et al. |
| 2013/0103103 A1 | 4/2013 | Mire et al. |
| 2013/0150670 A1 | 6/2013 | O'Prey et al. |
| 2013/0150674 A1 | 6/2013 | Haig et al. |
| 2013/0172674 A1 | 7/2013 | Kennedy, II et al. |
| 2013/0172676 A1 | 7/2013 | Levy et al. |
| 2013/0211202 A1 | 8/2013 | Perez-Cruet et al. |
| 2013/0282022 A1 | 10/2013 | Yousef |
| 2013/0289399 A1 | 10/2013 | Choi et al. |
| 2013/0303846 A1 | 11/2013 | Cybulski et al. |
| 2013/0304106 A1 | 11/2013 | Breznock |
| 2014/0025121 A1 | 1/2014 | Foley et al. |
| 2014/0066940 A1 | 3/2014 | Fang et al. |
| 2014/0074170 A1 | 3/2014 | Mertens et al. |
| 2014/0088367 A1 | 3/2014 | DiMauro et al. |
| 2014/0128979 A1 | 5/2014 | Womble et al. |
| 2014/0142584 A1 | 5/2014 | Sweeney |
| 2014/0148647 A1 | 5/2014 | Okazaki |
| 2014/0163319 A1 | 6/2014 | Blanquart et al. |
| 2014/0180321 A1 | 6/2014 | Dias et al. |
| 2014/0194697 A1 | 7/2014 | Seex |
| 2014/0215736 A1 | 8/2014 | Gomez et al. |
| 2014/0221749 A1 | 8/2014 | Grant et al. |
| 2014/0222092 A1 | 8/2014 | Anderson et al. |
| 2014/0257296 A1 | 9/2014 | Morgenstern Lopez |
| 2014/0257332 A1 | 9/2014 | Zastrozna |
| 2014/0257489 A1 | 9/2014 | Warren et al. |
| 2014/0261545 A1 | 9/2014 | Jenkins et al. |
| 2014/0275793 A1 | 9/2014 | Song |
| 2014/0275799 A1 | 9/2014 | Schuele |
| 2014/0276840 A1 | 9/2014 | Richter et al. |
| 2014/0276916 A1 | 9/2014 | Ahluwalia et al. |
| 2014/0277204 A1 | 9/2014 | Sandhu |
| 2014/0285644 A1 | 9/2014 | Richardson et al. |
| 2014/0318582 A1 | 10/2014 | Mowlai-Ashtiani |
| 2014/0336764 A1 | 11/2014 | Masson et al. |
| 2014/0357945 A1 | 12/2014 | Duckworth |
| 2014/0371763 A1 | 12/2014 | Poll et al. |
| 2014/0378985 A1 | 12/2014 | Mafi |
| 2015/0018623 A1 | 1/2015 | Friedrich et al. |
| 2015/0065795 A1 | 3/2015 | Titus |
| 2015/0073218 A1 | 3/2015 | Ito |
| 2015/0087913 A1 | 3/2015 | Dang et al. |
| 2015/0112398 A1 | 4/2015 | Morgenstern Lopez et al. |
| 2015/0133727 A1 | 5/2015 | Bacich et al. |
| 2015/0164496 A1 | 6/2015 | Karpowicz et al. |
| 2015/0216593 A1 | 8/2015 | Biyani |
| 2015/0223671 A1 | 8/2015 | Sung et al. |
| 2015/0223676 A1 | 8/2015 | Bayer et al. |
| 2015/0230697 A1 | 8/2015 | Phee et al. |
| 2015/0238073 A1 | 8/2015 | Charles et al. |
| 2015/0250377 A1 | 9/2015 | Iizuka |
| 2015/0257746 A1 | 9/2015 | Seifert |
| 2015/0272694 A1 | 10/2015 | Charles |
| 2015/0313585 A1 | 11/2015 | Abidin et al. |
| 2015/0313633 A1 | 11/2015 | Gross et al. |
| 2015/0327757 A1 | 11/2015 | Rozenfeld et al. |
| 2015/0335389 A1 | 11/2015 | Greenberg |
| 2015/0342619 A1 | 12/2015 | Weitzman |
| 2015/0342621 A1 | 12/2015 | Jackson, III |
| 2015/0366552 A1 | 12/2015 | Sasaki et al. |
| 2015/0374213 A1 | 12/2015 | Maurice, Jr. |
| 2015/0374354 A1 | 12/2015 | Boyd et al. |
| 2016/0015467 A1 | 1/2016 | Vayser et al. |
| 2016/0030061 A1 | 2/2016 | Thommen et al. |
| 2016/0066965 A1 | 3/2016 | Chegini et al. |
| 2016/0067003 A1 | 3/2016 | Chegini et al. |
| 2016/0074029 A1 | 3/2016 | O'Connell et al. |
| 2016/0095505 A1 | 4/2016 | Johnson et al. |
| 2016/0106408 A1 | 4/2016 | Ponmudi et al. |
| 2016/0166135 A1 | 6/2016 | Fiset |
| 2016/0174814 A1 | 6/2016 | Igov |
| 2016/0192921 A1 | 7/2016 | Pimenta et al. |
| 2016/0213500 A1 | 7/2016 | Beger et al. |
| 2016/0228280 A1 | 8/2016 | Schuele et al. |
| 2016/0235284 A1 | 8/2016 | Yoshida et al. |
| 2016/0256036 A1 | 9/2016 | Gomez et al. |
| 2016/0287264 A1 | 10/2016 | Chegini et al. |
| 2016/0296220 A1 | 10/2016 | Mast et al. |
| 2016/0324541 A1 | 11/2016 | Pellegrino et al. |
| 2016/0345952 A1 | 12/2016 | Kucharzyk et al. |
| 2016/0353978 A1 | 12/2016 | Miller et al. |
| 2016/0367294 A1 | 12/2016 | Boyd et al. |
| 2017/0003493 A1 | 1/2017 | Zhao |
| 2017/0007226 A1 | 1/2017 | Fehling |
| 2017/0007294 A1 | 1/2017 | Iwasaka et al. |
| 2017/0027606 A1 | 2/2017 | Cappelleri et al. |
| 2017/0042408 A1 | 2/2017 | Washburn et al. |
| 2017/0042411 A1 | 2/2017 | Kang et al. |
| 2017/0065269 A1 | 3/2017 | Thommen et al. |
| 2017/0065287 A1 | 3/2017 | Silva et al. |
| 2017/0086939 A1 | 3/2017 | Vayser et al. |
| 2017/0105770 A1 | 4/2017 | Woolley et al. |
| 2017/0135699 A1 | 5/2017 | Wolf |
| 2017/0156755 A1 | 6/2017 | Poll et al. |
| 2017/0156814 A1 | 6/2017 | Thommen et al. |
| 2017/0196549 A1 | 7/2017 | Piskun et al. |
| 2017/0224391 A1 | 8/2017 | Biester et al. |
| 2017/0245930 A1 | 8/2017 | Brannan et al. |
| 2017/0280969 A1 | 10/2017 | Levy et al. |
| 2017/0296038 A1 | 10/2017 | Gordon et al. |
| 2017/0311789 A1 | 11/2017 | Mulcahey et al. |
| 2018/0008138 A1 | 1/2018 | Thommen et al. |
| 2018/0008253 A1 | 1/2018 | Thommen et al. |
| 2018/0014858 A1 | 1/2018 | Biester et al. |
| 2018/0098788 A1 | 4/2018 | White et al. |
| 2018/0098789 A1 | 4/2018 | White et al. |
| 2018/0110503 A1 | 4/2018 | Flock et al. |
| 2018/0110506 A1 | 4/2018 | Thommen et al. |
| 2018/0153592 A1* | 6/2018 | Larson .............. A61B 17/7074 |
| 2018/0214016 A1 | 8/2018 | Thommen et al. |
| 2018/0249992 A1 | 9/2018 | Truckey |
| 2018/0333061 A1 | 11/2018 | Pracyk et al. |
| 2019/0209154 A1 | 7/2019 | Richter et al. |
| 2019/0216454 A1 | 7/2019 | Thommen et al. |
| 2019/0216486 A1 | 7/2019 | Weitzman |
| 2019/0374236 A1 | 12/2019 | Weitzman et al. |
| 2020/0360048 A1 | 11/2020 | White et al. |
| 2020/0367737 A1 | 11/2020 | Matsumoto et al. |
| 2021/0052298 A1 | 2/2021 | Thommen et al. |
| 2021/0186316 A1 | 6/2021 | Thommen et al. |
| 2021/0204973 A1 | 7/2021 | Thommen et al. |
| 2021/0282806 A1 | 9/2021 | Thommen et al. |
| 2022/0192700 A1 | 6/2022 | Thommen et al. |
| 2022/0249125 A1 | 8/2022 | Thommen et al. |
| 2022/0265134 A1 | 8/2022 | Thommen et al. |

FOREIGN PATENT DOCUMENTS

| | | |
|---|---|---|
| CN | 1742685 A | 3/2006 |
| CN | 101426437 A | 5/2009 |
| CN | 201290744 Y | 8/2009 |
| CN | 101815476 A | 8/2010 |
| CN | 102448380 A | 5/2012 |
| CN | 202211669 U | 5/2012 |
| CN | 102497828 A | 6/2012 |
| CN | 102821673 A | 12/2012 |
| CN | 102843984 A | 12/2012 |
| CN | 202740102 U | 2/2013 |
| CN | 102727309 B | 11/2014 |
| CN | 105286776 A | 2/2016 |
| CN | 103976779 B | 9/2016 |
| CN | 106794032 A | 5/2017 |

(56) References Cited

FOREIGN PATENT DOCUMENTS

| | | |
|---|---|---|
| CN | 107126254 A | 9/2017 |
| DE | 9415039 U1 | 11/1994 |
| DE | 29916026 U1 | 11/1999 |
| DE | 20309079 U1 | 8/2003 |
| EP | 0 537 116 A1 | 4/1993 |
| EP | 0 807 415 A2 | 11/1997 |
| EP | 0 891 156 A1 | 1/1999 |
| EP | 0890341 A1 | 1/1999 |
| EP | 2 491 848 A1 | 8/2012 |
| GB | 2481727 A | 1/2012 |
| JP | 05-207962 A | 8/1993 |
| JP | 08-278456 A | 10/1996 |
| JP | 2000126190 A | 5/2000 |
| JP | 2000-511788 A | 9/2000 |
| JP | 2001520906 A | 11/2001 |
| JP | 2007-007438 A | 1/2007 |
| JP | 2008-508943 A | 3/2008 |
| JP | 2009543612 A | 12/2009 |
| JP | 2011-512943 A | 4/2011 |
| JP | 2012527327 A | 11/2012 |
| JP | 2012527930 A | 11/2012 |
| JP | 2013059688 A | 4/2013 |
| JP | 2013-538624 A | 10/2013 |
| JP | 2014-517710 A | 7/2014 |
| JP | 2015-500680 A | 1/2015 |
| JP | 2015-521913 A | 8/2015 |
| WO | 96/29014 A1 | 9/1996 |
| WO | 97/34536 A2 | 9/1997 |
| WO | 2001/056490 A1 | 8/2001 |
| WO | 2001/089371 A1 | 11/2001 |
| WO | 2002/002016 A1 | 1/2002 |
| WO | 2004/039235 A2 | 5/2004 |
| WO | 2004/103430 A2 | 12/2004 |
| WO | 2006/017507 A2 | 2/2006 |
| WO | 2007/059068 A1 | 5/2007 |
| WO | 2008/121162 A1 | 10/2008 |
| WO | 2009/033207 A1 | 3/2009 |
| WO | 2009/108318 A2 | 9/2009 |
| WO | 2010/111629 A2 | 9/2010 |
| WO | 2010138083 A1 | 12/2010 |
| WO | 2012/004766 A2 | 1/2012 |
| WO | 2012/040239 A1 | 3/2012 |
| WO | 2012/122294 A1 | 9/2012 |
| WO | 2013/033426 A2 | 3/2013 |
| WO | 2013/059640 A1 | 4/2013 |
| WO | 2013/074396 A1 | 5/2013 |
| WO | 2014/041540 A1 | 3/2014 |
| WO | 2014/050236 A1 | 4/2014 |
| WO | 2014/100761 A2 | 6/2014 |
| WO | 2014/185334 A1 | 11/2014 |
| WO | 2015026793 A1 | 2/2015 |
| WO | 2015/175635 A1 | 11/2015 |
| WO | 2016/111373 A1 | 7/2016 |
| WO | 2016/131077 A1 | 8/2016 |
| WO | 2016/168673 A1 | 10/2016 |
| WO | 2016/201292 A1 | 12/2016 |
| WO | 2017/006684 A1 | 1/2017 |
| WO | 2017/015480 A1 | 1/2017 |
| WO | 2017/040873 A1 | 3/2017 |
| WO | 2017/083648 A1 | 5/2017 |
| WO | 2018/131039 A1 | 7/2018 |
| WO | 2018/165365 A2 | 9/2018 |
| WO | 2021/209987 A1 | 10/2021 |

OTHER PUBLICATIONS

Extended European Search Report for Application No. 18758290.3, dated Nov. 27, 2020 (7 pages).
Australian Examination Report for Application No. 2018225113, dated Jul. 15, 2022 (4 pages).
Chinese Office Action for Application No. 201880016688.9, dated Mar. 8, 2022, with Translation (21 pages).
Extended European Search Report for Application No. 18764249.1, dated Mar. 11, 2022 (8 pages).
Extended European Search Report for Application No. 18764504.9, dated Mar. 18, 2022 (7 pages).
Extended European Search Report for Application No. 18764370.5, dated Mar. 25, 2022 (8 pages).
Japanese Office Action for Application No. 2019-548591, dated Oct. 5, 2021, (14 pages).
Japanese Office Action for Application No. 2020-513791, dated May 17, 2022 (8 Pages).
Japanese Office Action for Application No. 2020-177880, dated May 31, 2022 (3 pages).
U.S. Appl. No. 15/254,877, filed Sep. 1, 2016, Multi-Shield Spinal Access System.
U.S. Appl. No. 15/437,792, filed Feb. 21, 2017, Multi-Shield Spinal Access System.
U.S. Appl. No. 15/931,839, filed Aug. 31, 2017, Surgical Visualization Systems and Related Methods.
U.S. Appl. No. 15/697,494, filed Sep. 7, 2017, Multi-Shield Spinal Access System.
U.S. Appl. No. 15/786,846, filed Oct. 18, 2017, Devices and Methods for Surgical Retraction.
U.S. Appl. No. 15/786,858, filed Oct. 18 2017, Devices and Methods for Providing Surgical Access.
U.S. Appl. No. 15/786,891, filed Oct. 18, 2017, Surgical Access Port Stabilization.
U.S. Appl. No. 15/786,923, filed Oct. 18, 2017, Surgical Instrument Connectors and Related.
U.S. Appl. No. 15/901,435, filed Feb. 21 2018, Surgical Visualization Systems and Related.
U.S. Appl. No. 15/931,839, filed May 14, 2020, Surgical Access Port Stabilization.
U.S. Appl. No. 15/966,293, filed Apr. 30, 2018, Neural Monitoring Devices and Methods.
U.S. Appl. No. 16/352,654, filed Mar. 13, 2019, Multi-Shield Spinal Access System.
U.S. Appl. No. 16/985 200, filed Aug. 4 2020, Devices and Methods for Providing Surgical Access.
U.S. Appl. No. 17/192,889, filed Mar. 5, 2021, Surgical Visualization Systems and Related Methods.
Extended European Search Report for Application No. 20212396.4, dated Sep. 23, 2021 (9 pages).
Extended European Search Report for Application No. 18854503, dated Apr. 15, 2021 (10 pages).
Extended European Search Report for Application No. 19758283.6, dated Sep. 28, 2021 (8 pages).
U.S. Appl. No. 16/362,497, filed Mar. 22, 2019, Surgical Instrument Connectors and Related Methods.
U.S. Appl. No. 17/089,695, filed Nov. 4, 2020, Multi-Shield Spinal Access System.
U.S. Appl. No. 17/159,129, filed Jan. 26, 2021, Multi-Shield Spinal Access System.
U.S. Appl. No. 17/692,942, filed Mar. 11, 2022, Multi-Shield Spinal Access System.
Extended European Search Report for Application No. 16843037.9; dated Mar. 14, 2019 (8 pages).
Hott, J. S., et al., "A new table-fixed retractor for anterior odontoid screw fixation: technical note," J Neurosurg (Spine 3), 2003, v. 98, pp. 118-120.
International Preliminary Report on Patentability issued for Application No. PCT/US2016/050022, dated Mar. 15, 2018.
International Search Report and Written Opinion for Application No. PCT/EP2020/056706, dated Jun. 9, 2020 (17 pages).
International Search Report and Written Opinion for Application No. PCT/US18/21449, dated Aug. 27, 2018 (13 pages).
International Search Report and Written Opinion for Application No. PCT/US18/21454, dated Jul. 3, 2018 (16 pages).
International Search Report and Written Opinion for Application No. PCT/US18/21466 dated Jul. 3, 2018 (8 pages).
International Search Report and Written Opinion for Application No. PCT/US18/47136, dated Jan. 23, 2019 (9 pages).
International Search Report and Written Opinion for Application No. PCT/US19/18700, dated May 3, 2019 (7 pages).
International Search Report and Written Opinion for Application No. PCT/US2015/043554, dated Nov. 19, 2015 (8 pages).

(56) References Cited

OTHER PUBLICATIONS

International Search Report and Written Opinion for Application No. PCT/US2015/048485, dated Feb. 9, 2016. 16 pages).
International Search Report and Written Opinion for Application No. PCT/US2015/060978, dated Feb. 15, 2016 8 pages).
International Search Report and Written Opinion for Application No. PCT/US2016/050022, dated Feb. 1, 2017 49 pages).
International Search Report and Written Opinion for Application No. PCT/US2018/018905, dated May 7, 2018 (10 pages).
International Search Report and Written Opinion issued for Application No. PCT/US2018/021472, dated Jul. 19, 2018.
International Search Report for Application No. PCT/IB18/57367, dated Jan. 29, 2019, (4 pages).
Invitation to Pay Additional Fees for Application No. PCT/US2016/050022, dated Nov. 3, 2016 (2 pages).
Iprenburg, M, "Percutaneous Transforaminal Endoscopic Discectomy: The Thessys Method," in Lewandrowski, K., et al, Minimally Invasive Spinal Fusion Techniques, Summit Communications, 2008 pp. 65-81.
Japanese Office Action issued in Appln. No. JP 2018-511695, dated May 26, 2020 (21 pages).
Jung, K., et al., "A hands-free region-of-interest selection interface for solo surgery with a wide-angle endoscope: preclinical proof of concept," Surg Endosc, 2017, v. 31, pp. 974-980.
Regan, J. M et al., "Burr Hole Washout versus Craniotomy for Chronic Subdural Hematoma: Patient Outcome and Cost Analysis," Plos One, Jan. 22, 2015, DOI:10.1371/journal.pone.0115085.
Shalayev, S. G. et al., "Retrospective analysis and modifications of retractor systems for anterior odontoid screw fixation," Neurosurg Focus 16 (1):Article 14, 2004, pp. 1-4.
Chinese Office Action for Application No. 201880013056.7, dated Mar. 25, 2021 (15 pages).
U.S. Appl. No. 17/214,759, filed Mar. 26, 2021, Multi-Shield Spinal Access System.
Japanese Office Action for Application No. 2019-545263, dated Jan. 4, 2022 (11 pages).
U.S. Appl. No. 17/728,967, filed Apr. 25, 2022, Surgical Visualization Systems and Related Methods.
U.S. Appl. No. 17/740,305, filed May 9, 2022, Surgical Visualization Systems and Related Methods.
U.S. Appl. No. 18/091,255 filed Dec. 29, 2022, Multi-Shield Spinal Access System.
Chinese Decision of Reexamination issued for 201680051245.4, dated Aug. 23, 2022, (23 pages).
Chinese Office Action and Search Report issued for Application No. 201880058099, dated Nov. 2, 2022 (14 pages).
Clinical Workbook of Neurosurgery in Xijing [M], edited by Fei Zhou, Xi'an: Fourth Military Medical University Press, Aug. 2012, pp. 431-432: an endoscope with a diameter of 3.7 mm is used for intramedullary examination).
Japanese Office Action for Application No. 2019-545263, dated Aug. 9, 2022 (8 pages).

* cited by examiner

FIG. 13A
FIG. 13B
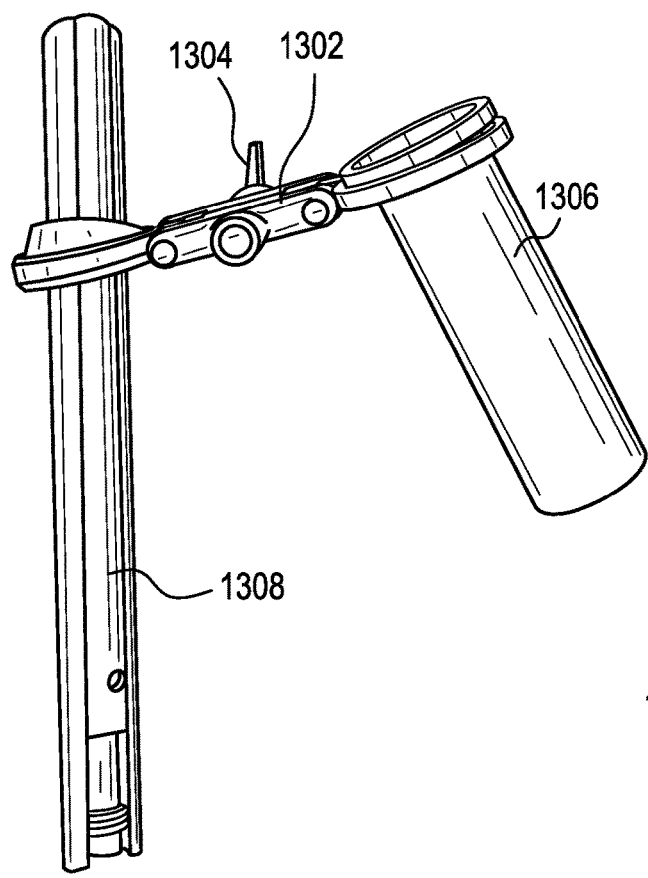
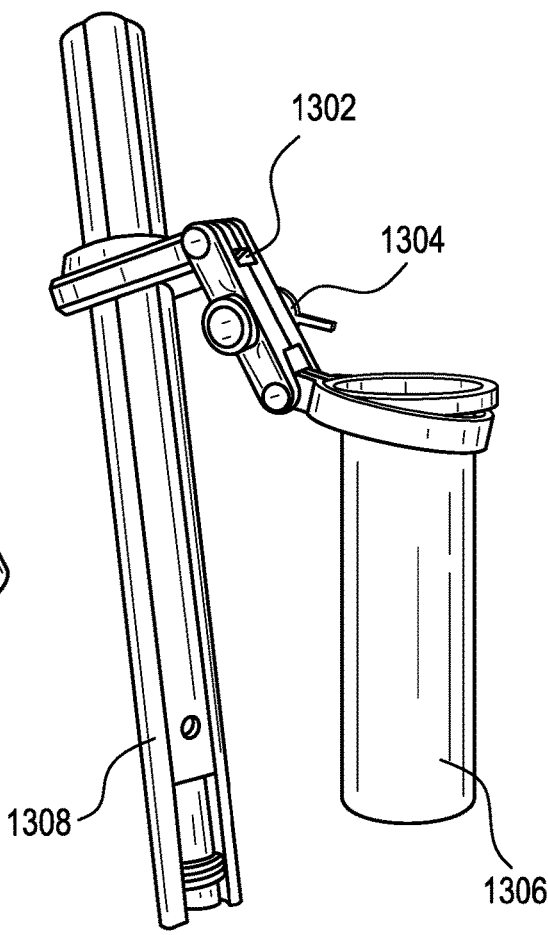

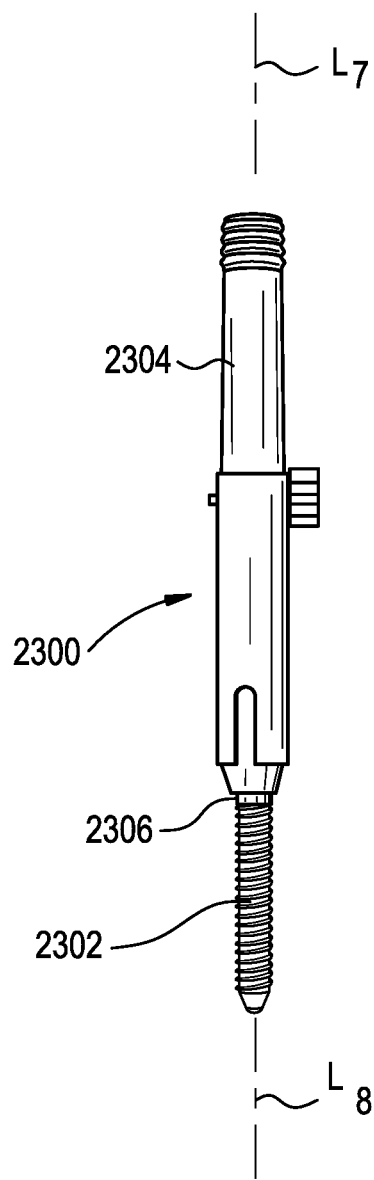
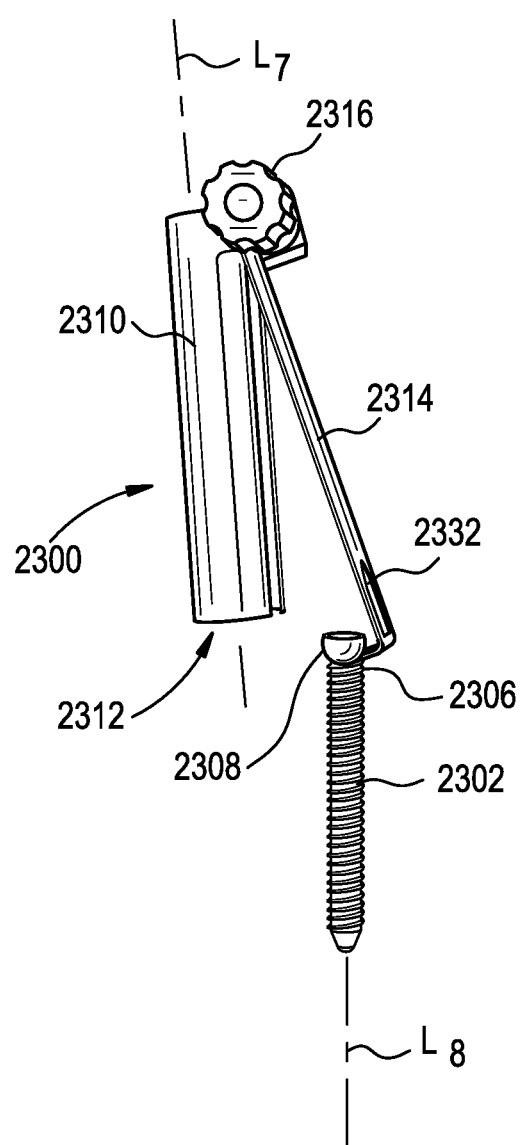

FIG. 26
FIG. 27
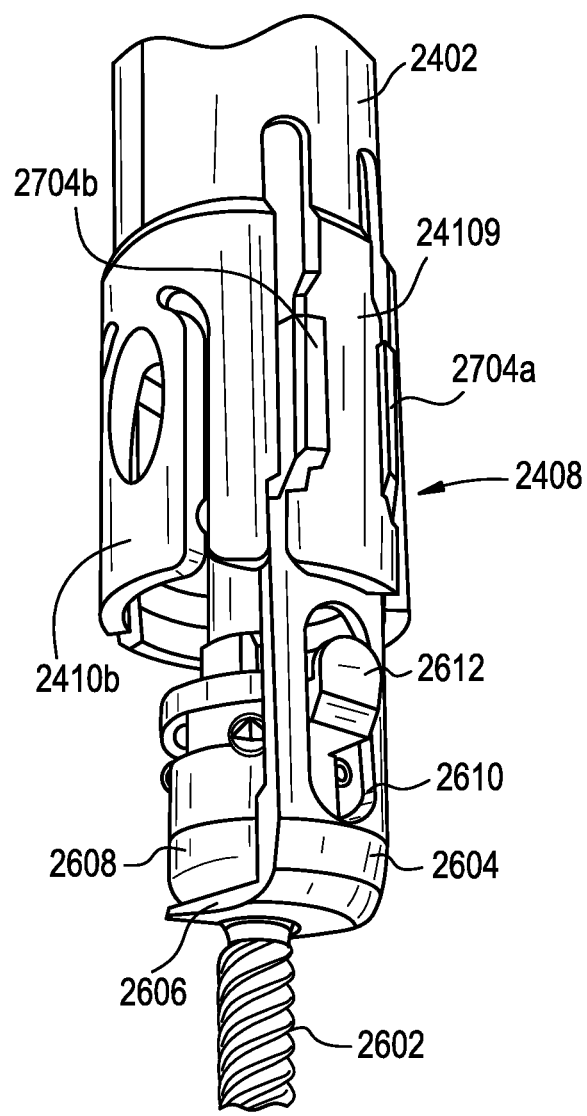
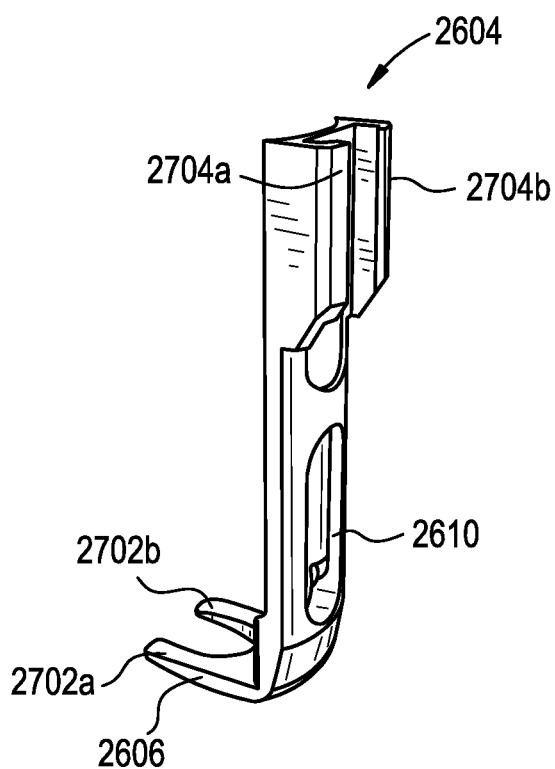

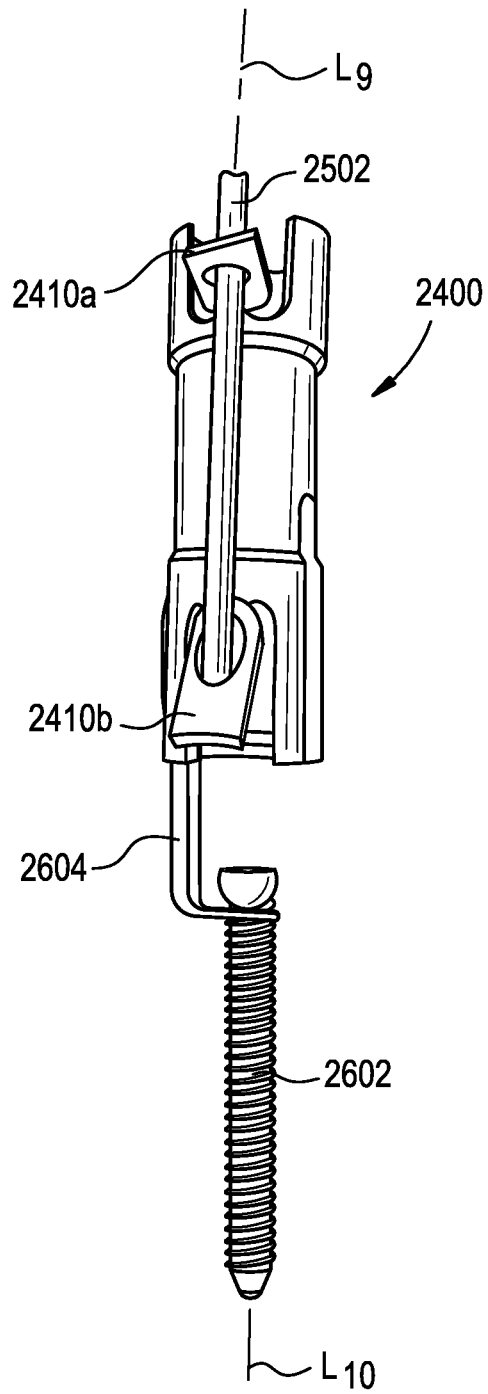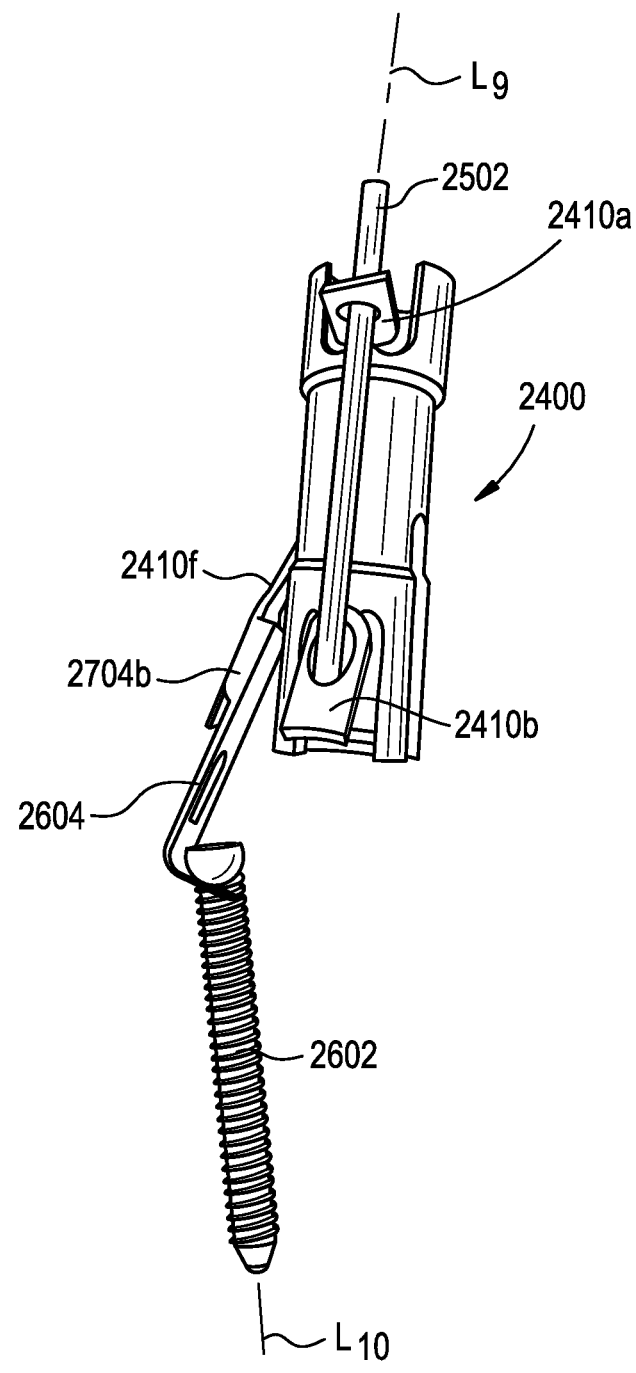

FIG. 29
FIG. 30
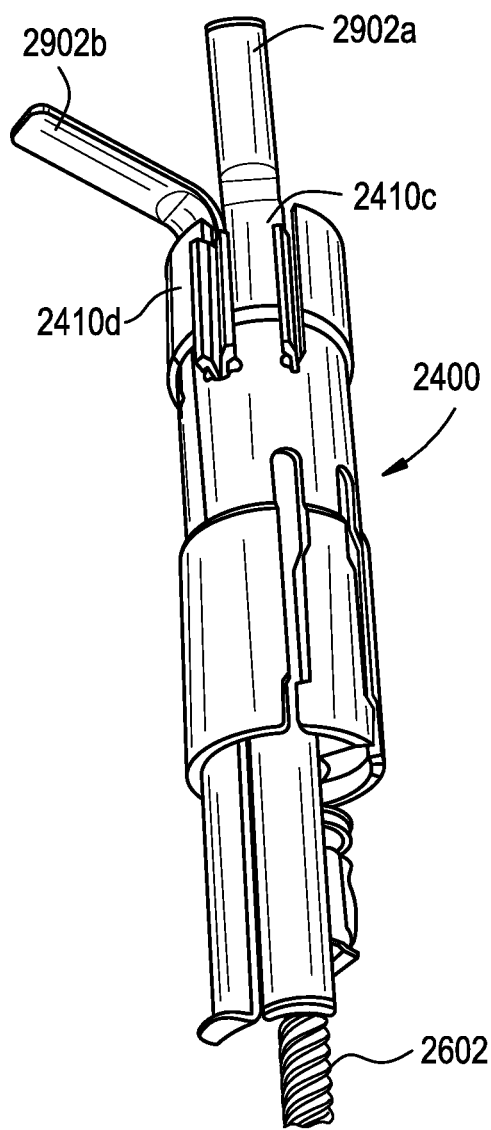
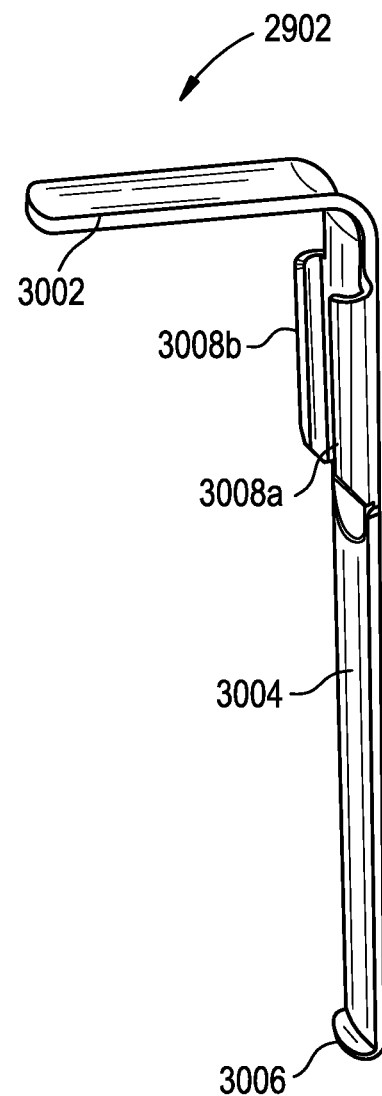

FIG. 31C
FIG. 31D
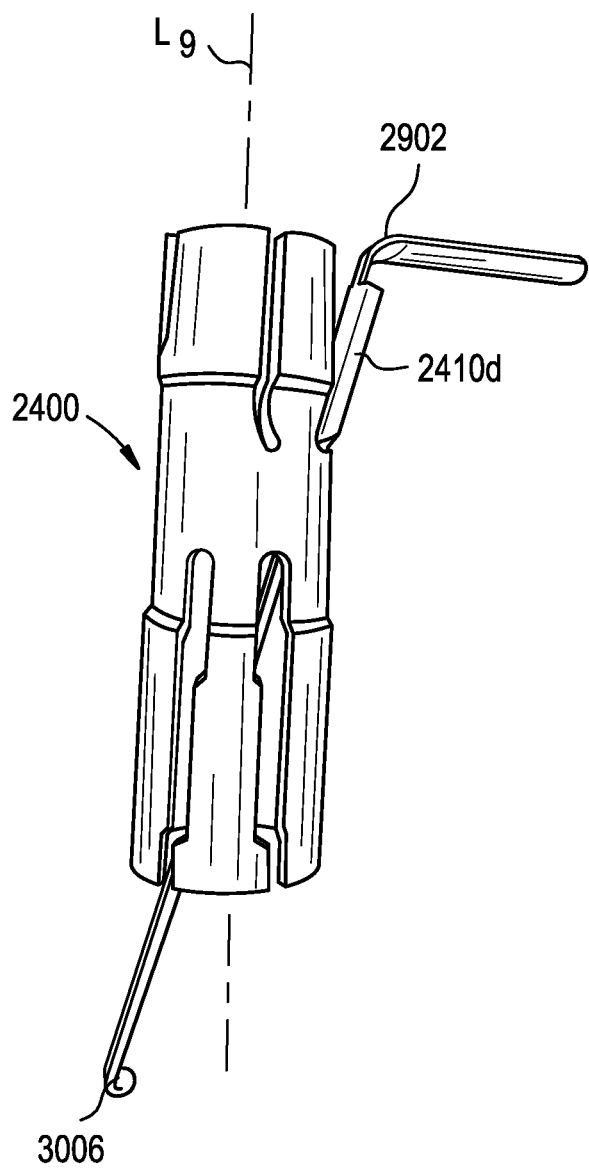
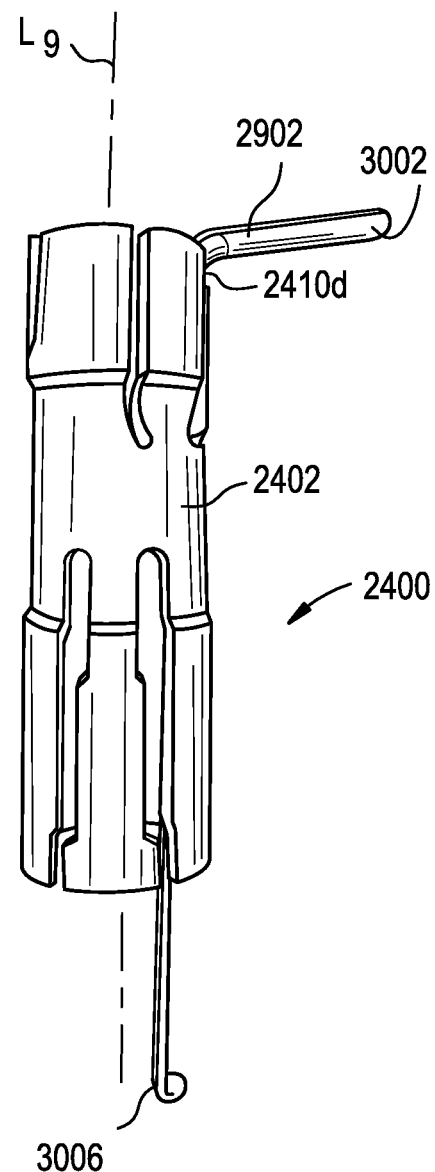

SURGICAL ACCESS PORT STABILIZATION

CROSS-REFERENCE TO RELATED APPLICATIONS

The present application is a continuation of U.S. application Ser. No. 15/786,891, filed Oct. 18, 2017. U.S. application Ser. No. 15/786,891 claims priority to U.S. Provisional Application No. 62/468,475, filed on Mar. 8, 2017. U.S. application Ser. No. 15/786,891 is also a continuation-in-part of U.S. application Ser. No. 15/437,792 filed on Feb. 21, 2017. U.S. application Ser. No. 15/437,792 is a continuation-in-part of U.S. application Ser. No. 15/254,877 filed on Sep. 1, 2016. U.S. application Ser. No. 15/254,877 claims priority to U.S. Provisional Application No. 62/214,297 filed on Sep. 4, 2015. The entire contents of each of these applications are incorporated by reference herein.

FIELD

This disclosure relates generally to surgical instruments, systems, and methods, and more particularly to instruments, systems, and methods for stabilization of a surgical access port that can be used in various procedures, e.g., orthopedic or neurologic surgical procedures such as spinal fusion surgery.

BACKGROUND

Surgical procedures are used to treat and cure a wide range of diseases, conditions, and injuries. Surgery often requires access to internal tissue through open or minimally invasive surgical procedures. The term "minimally invasive" refers to all types of minimally invasive surgical procedures, including endoscopic, laparoscopic, arthroscopic, natural orifice intraluminal, and natural orifice transluminal procedures. Minimally invasive surgery can have numerous advantages compared to traditional open surgical procedures, including reduced trauma, faster recovery, reduced risk of infection, and reduced scarring.

Whether minimally invasive or not, there are a number of surgical procedures in which it can be desirable to form a working channel in a patient to provide access to a surgical site within the patient. One such example is orthopedic or neurologic surgical procedures, including, e.g., spinal fusion procedures where it can be desirable to form a working channel through a patient's tissue to access their vertebrae and/or the intervertebral discs disposed between adjacent vertebrae.

A variety of surgical access devices are known, including various devices that are anchored to a surgical table upon which a patient is disposed, or devices that penetrate tissue without being anchored to any other structure. In such arrangements, the access device may be inadequately supported, or the access device may undesirably move relative to the patient if the patient moves relative to the operating table. Accordingly, there is a need for improved access port stabilization devices, systems, and methods that can streamline the instrumentation and methodology of various surgical procedures.

SUMMARY

In some embodiments, improved ipsilateral access port stabilization is provided via an access port configured to couple to an anchor, such as a bone screw, implanted in a patient at a location nearby the surgical site, e.g., on an ipsilateral side. The access port can be coupled to the anchor via a linkage and can have a variety of degrees of freedom to adjust its position relative to the anchor and patient. Further, the access port can be configured to be selectively locked in a desired position to permit stabilized access to a surgical site. While the systems, devices, and methods described herein can be utilized in a variety of surgical procedures, they can have particular utility in various orthopedic or neurologic surgical procedures, such as spinal operations.

In one aspect, a surgical system is provided that can include an access port configured for percutaneous insertion into a patient to define a channel to a surgical site, and an anchor configured for insertion into the patient's bone. Further, the access port can be coupled to the anchor such that a longitudinal axis of the access port and a longitudinal axis of the anchor are non-coaxial.

The devices and methods described herein can have a number of additional features and/or variations, all of which are within the scope of the present disclosure. In some embodiments, for example, the access port can be configured to be coupled to an anchor on an ipsilateral side of a patient's body, i.e., a same side. For example, in the context of spinal orthopedic surgery, this can mean that the access port can be coupled to an anchor disposed in a patient's vertebra on a same side of the spine or patient midline as the access port. This is in contrast to other techniques, such as those mentioned above, that couple access ports to anchors disposed on a contralateral side of the patient's body, i.e., an opposite side. In some embodiments, the access port can be configured to be coupled to an anchor on a contralateral side of a patient's body.

In some embodiments, a position of the access port relative to the anchor can be selectively locked to maintain the access port in a desired position relative to the anchor. This can be useful, for example, to maintain the access port in alignment with a desired surgical site. A variety of locking mechanisms are possible, as described below.

In certain embodiments, the access port can be coupled to the anchor by a linkage. The linkage can have a variety of forms. In some embodiments, the linkage can be a single shaft protruding from the access port, while in other embodiments the linkage can be a multi-component structure capable of adjustment and selective locking.

In some embodiments, the linkage can be deformable. For example, in some embodiments the linkage can be formed from metal capable of deformation under force (i.e., manipulation by a user). In other embodiments, the linkage can be selectively lockable so as to no longer be deformable. For example, the linkage can be selectively locked by application of electricity thereto in some embodiments, while in other embodiments the linkage can be selectively locked by an adjustment screw or other mechanical locking mechanism.

In some embodiments, a length of the access port can be adjusted. For example, a length of the access port can be adjusted by telescoping an inner sleeve of the access port relative to an outer sleeve of the access port. This can allow the access port to have varying heights and extend varying distances both into a patient's body and away from a patient's skin surface.

In some embodiments, the linkage can form a portion of an outer circumference of the access port and pivot relative to the access port. In other embodiments, the access port can include a deformable portion. The deformable portion can couple with the anchor in certain embodiments. Still further, in some embodiments the deformable portion can couple with the anchor below a polyaxial head of the anchor. A number of additional components can be included and coupled to the access port in a variety of manners. For example, in some embodiments a nerve shield or other soft tissue retractor can be coupled to the deformable portion of the access port.

In some embodiments, the anchor can include opposed extensions extending proximally away from a distal portion thereof and the access port can couple to the anchor by compressing a portion of the access port between the opposed extensions. In such an embodiment, the system can further include a clamp configured to compress the opposed extensions toward one another.

The clamp can have a variety of forms. For example, in some embodiments the clamp can define an inner lumen configured to receive the opposed extensions such that the clamp slides along a length of the opposed extensions. In other embodiments, the access port can include a shaft extending transversely to a longitudinal axis of the access port and a split ball disposed around the shaft between the opposed extensions. The clamp can cause the extensions to compress against the split ball and the shaft, thereby locking a position of the access port relative to the anchor. In some embodiments, the clamp can be coupled to the split ball and configured to pivot relative thereto to compress the opposed extensions onto the split ball.

In another aspect, a surgical method is provided that can include inserting an anchor into a patient's bone, coupling an access port to the anchor, and positioning the access port relative to the anchor on a same side of the patient's body such that a longitudinal axis of the access port and a longitudinal axis of the anchor are non-coaxial. Further, the access port can define a channel to a surgical site.

As with the system described above, a number of variations and additional features are possible. For example, in some embodiments the anchor can be inserted into a patient's vertebra, such as during a spinal orthopedic procedure.

Moreover, in some embodiments the method can further include locking a position of the access port relative to the anchor. In some embodiments, positioning the access port can include deforming a linkage extending between the access port and the anchor.

In some embodiments, the method can include applying electricity to the linkage to lock a position of the access port relative to the anchor. In some embodiments, the method can include actuating an adjustment screw to lock the position of the access port relative to the anchor. In some embodiments, the method can further include adjusting a length of the access port by telescoping an inner sleeve of the access port relative to an outer sleeve of the access port.

In some embodiments, the method can further include deforming a portion of the access port. Moreover, in some embodiments coupling the access port to the anchor can include coupling the anchor with a deformable portion of the access port. Still further, in some embodiments the method can further include coupling a nerve shield or other soft tissue retractor to a deformable portion of the access port.

In some embodiments, coupling the access port to the anchor can include compressing a portion of the access port between opposed extensions of the anchor that extend proximally away from a distal portion thereof.

In another aspect, a surgical method can include introducing an access port and an anchor into a patient's body in a configuration wherein a longitudinal axis of the access port and a longitudinal axis of the anchor are coaxial, as well as adjusting a position of the access port relative to the anchor such that the longitudinal axis of the access port and the longitudinal axis of the anchor are non-coaxial and the access port and the anchor are on a same side of the patient's body.

In some embodiments, the anchor can be inserted into a patient's vertebra, while in other embodiments the method can include inserting the anchor into a different portion of a patient's body. In some embodiments, the access port and the anchor can be coupled to a driver for introduction into the patient's body. The driver can maintain alignment of the components and provide for rotating the anchor to implant it in a patient's bone in some embodiments. The method can further include removing the driver prior to adjusting the position of the access port relative to the anchor in certain embodiments, e.g., to free the access port to move relative to the anchor where the driver maintains alignment of the access port and anchor.

In some embodiments, the method can further include inserting a second anchor into the patient's body through the access port and re-adjusting a position of the access port relative to the anchor such that the longitudinal axis of the access port and the longitudinal axis of the anchor are coaxial. The method can further include inserting a polyaxial receiving head through the access port and coupling the receiving head to the anchor, coupling the anchor and the second anchor with a spinal fixation element, and removing the access port. In still other embodiments, the method can further include locking a position of the access port relative to the anchor after adjusting a position of the access port relative to the anchor.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF THE DRAWINGS

FIG. 13A is a side view of one embodiment of a surgical system including an adjustable linkage in a first configuration;

FIG. 13B is a side view of the system of FIG. 13A in a second configuration;

FIG. 23A is a front view of one embodiment of an access port, anchor, and driver;

FIG. 23B is a side view of the access port and anchor of FIG. 23A in a first configuration;

FIG. 26 is a bottom perspective view of the access port of FIG. 24A coupled to an anchor;

FIG. 27 is a detail view of a linkage of FIG. 26 for coupling an access port to an anchor;

FIG. 28A is a side view of the access port and light and/or camera of FIG. 25 coupled to an anchor in a first configuration;

FIG. 28B is a side view of the access port and light and/or camera of FIG. 28A in a second configuration;

FIG. 29 is a bottom perspective view of the access port of FIG. 24A coupled to a nerve shield;

FIG. 30 is a detail view of a nerve shield of FIG. 29;

FIG. 31C is a front view of the access port of FIG. 31B after advancing a nerve shield;

FIG. 31D is a front view of the access port of FIG. 31C after retracting a nerve shield.

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure.

Additionally, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can easily be determined for any geometric shape. Further, in the present disclosure, like-numbered components of the embodiments generally have similar features. Still further, sizes and shapes of the devices, and the components thereof, can depend at least on the anatomy of the subject in which the devices will be used, the size and shape of components with which the devices will be used, and the methods and procedures in which the devices will be used.

Surgical devices, systems, and methods are described herein that provide access port stabilization through an access port configured to couple to an anchor, such as a bone screw, that can be implanted in a patient at a location nearby a surgical site, e.g., ipsilateral stabilization to a point on an ipsilateral side of a patient's body or contralateral stabilization to a point on a contralateral side of the patient's body. The access port can be coupled to the anchor in a manner that provides a variety of degrees of freedom to adjust its position relative to the anchor and patient. Further, the access port can be configured to be selectively locked in a desired position to permit stabilized access to a surgical site. While the devices, systems, and methods described herein can be utilized in a variety of surgical procedures, they can have particular utility in various orthopedic or neurologic surgical procedures, such as spinal operations.

Figure 1:
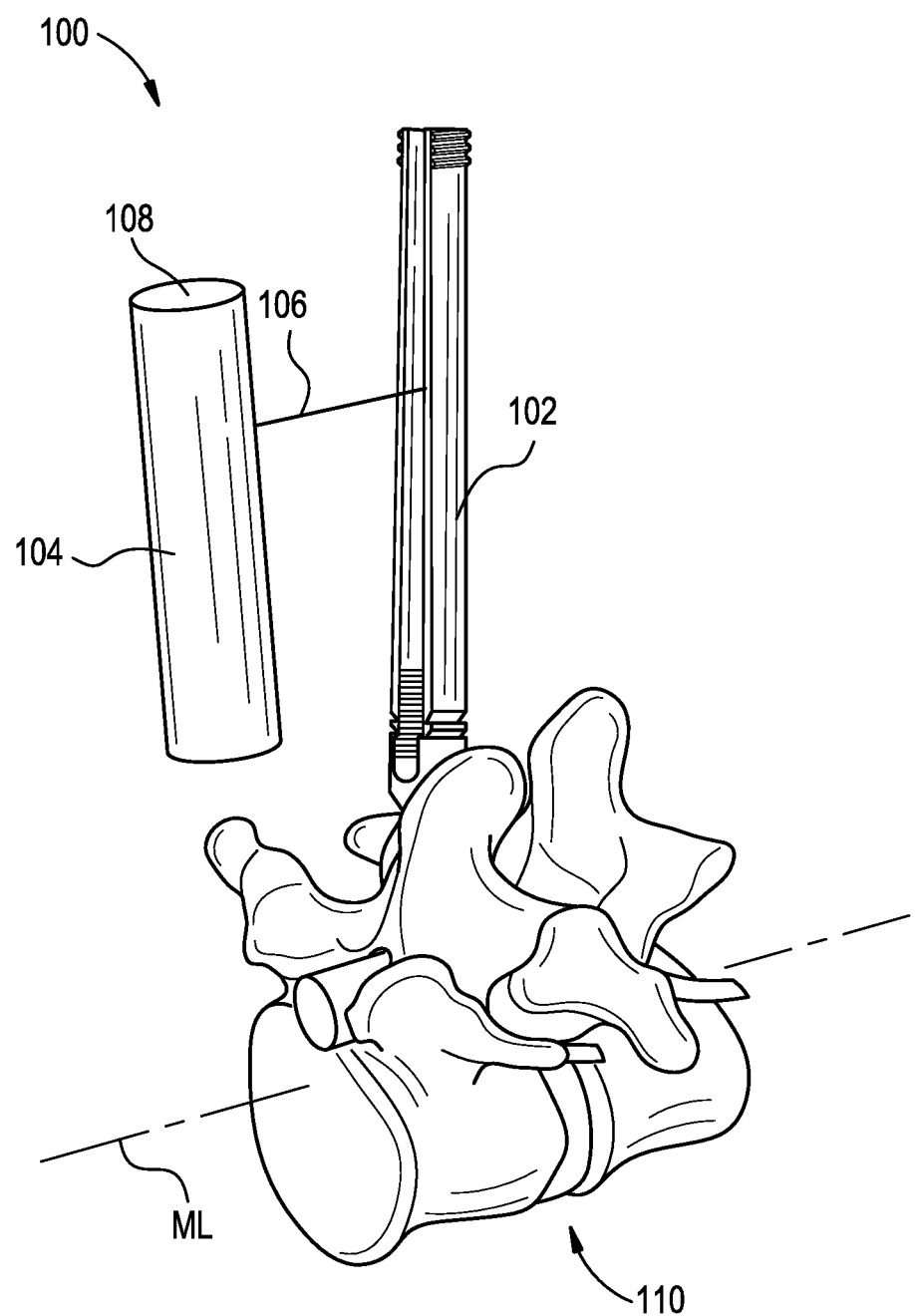
FIG. 1 is a schematic illustration of one embodiment of a surgical system according to the teachings provided herein.

FIG. 1 illustrates an exemplary surgical system 100 according to the teachings provided herein, though it will be appreciated that components of such a system can be used in various other applications instead or in addition. Further details on systems similar to that illustrated in FIG. 1 can be found in U.S. Patent Publication No. 2017/0156814 filed on Feb. 21, 2017 and entitled "Multi-Shield Spinal Access System," which is hereby incorporated by reference in its entirety. The system 100 can be used in various surgical procedures, including spinal surgeries such as microsurgical bone resection, spinal decompression, spinal fusion, and the like. In general, the system 100 can include any one or more of a pedicle post or other anchor 102 and an access port 104. Other possible components not illustrated here can include a tissue retractor, a camera or visualization system, and any of a variety of other surgical instruments. The access port 104 can have an adjustable length, e.g., as described in U.S. Patent Publication No. 2018/0098789 filed on Oct. 18, 2017, entitled "Devices And Methods For Providing Surgical Access." The access port 104 can be used with a surgical visualization system, e.g., as described in U.S. Publication No. 2018/0008138 filed on Aug. 31, 2017 and entitled "Surgical Visualization Systems And Related Methods." The access port 104 can be used with a nerve retractor or nerve shield, e.g., as described in U.S. Publication No. 2018/0110503, filed Oct. 18, 2017, entitled "Devices And Methods For Surgical Retraction." Each of the above applications is hereby incorporated by reference in its entirety.

An exemplary method of using the system of FIG. 1 can include any one or more of the following steps, performed in any of a variety of sequences: a) making an incision in a skin of a patient; b) percutaneously inserting through the incision an access device having a substantially tubular shape (such as a tube or a multi-slotted retractor), the access device having a length adapted to extend from the incision to a border between sensitive and insensitive tissue (e.g., a superior articular process (SAP), or a lamina) in the spine of the patient; c) stabilizing the access device to an anchor (e.g., a pedicle anchor); d) inserting an access device integrated optical visualization instrument; e) resecting a portion of the superior articular process, and/or performing a microsurgical decompression procedure; f) inserting or deploying a tissue retractor through or from the access device so that a distal end portion of the tissue retractor extends to the intervertebral disc, the retractor having an outer surface; g) contacting the outer surface of the retractor to a nerve root to shield the nerve root; h) microsurgically decompressing any tissue deemed to be causing nerve impingement; i) extracting intervertebral disc material including removing cartilaginous material from the vertebral endplates; j) inserting an interbody device; and k) deploying a mechanism of stabilization to stabilize the intervertebral segment.

As shown in FIG. 1, stabilization of the access port or device 104 can be accomplished by coupling it to the anchor 102. In some embodiments, this can be accomplished through a linkage 106. In still further embodiments, the system can be configured to selectively lock a position of the access port 104 relative to the anchor 102 such that a lumen, channel, or passageway 108 through the access port is aligned with a desired surgical site. In some surgical procedures, an access port can be attached to an anatomical anchor point (e.g., a pedicle screw extension tab or tower) that is disposed on an opposite side of the patient's body from the access port (contralateral). For example, in spinal surgery, the anchor can be disposed on an opposite side of the spine or patient midline from the access port. Exemplary connectors for such stabilization are described herein and disclosed in U.S. Publication No. 2018/0110506, filed Oct. 18, 2017, entitled "Surgical Instrument Connectors And Related Methods," which is hereby incorporated by reference in its entirety. In some cases, it can be desirable to stabilize an access port relative to an anchor disposed on a same side of the patient's body (ipsilateral). In the system 100 of FIG. 1, the access port 104 is stabilized relative to the anchor 102 and both components are disposed on a same side of the patient's spine 110 or midline axis ML (ipsilateral). In other arrangements, the access port 104 can be stabilized to a contralateral anchor 102 or other structure. FIGS. 2-32 illustrate various systems, devices, and methods for access port stabilization.

In some embodiments, it can be advantageous to utilize an access device or system that is anchored to a patient's body, as opposed to an external structure, such as a surgical table, etc. For example, anchoring relative to a patient's body can provide an advantage by maintaining a relative position between an access device and a patient even if a patient moves during a procedure. Moreover, in other embodiments it can be advantageous to anchor all devices on an ipsilateral side of the patient's body, e.g., on a single or same side of a patient's spine. In some procedures, this can reduce the complexity of instrumentation utilized in a surgical procedure and allow parallel operations to proceed on both sides of a patient's spine or midline axis in parallel. Further, it can reduce the number of devices or steps required to perform a procedure.

Figure 2:
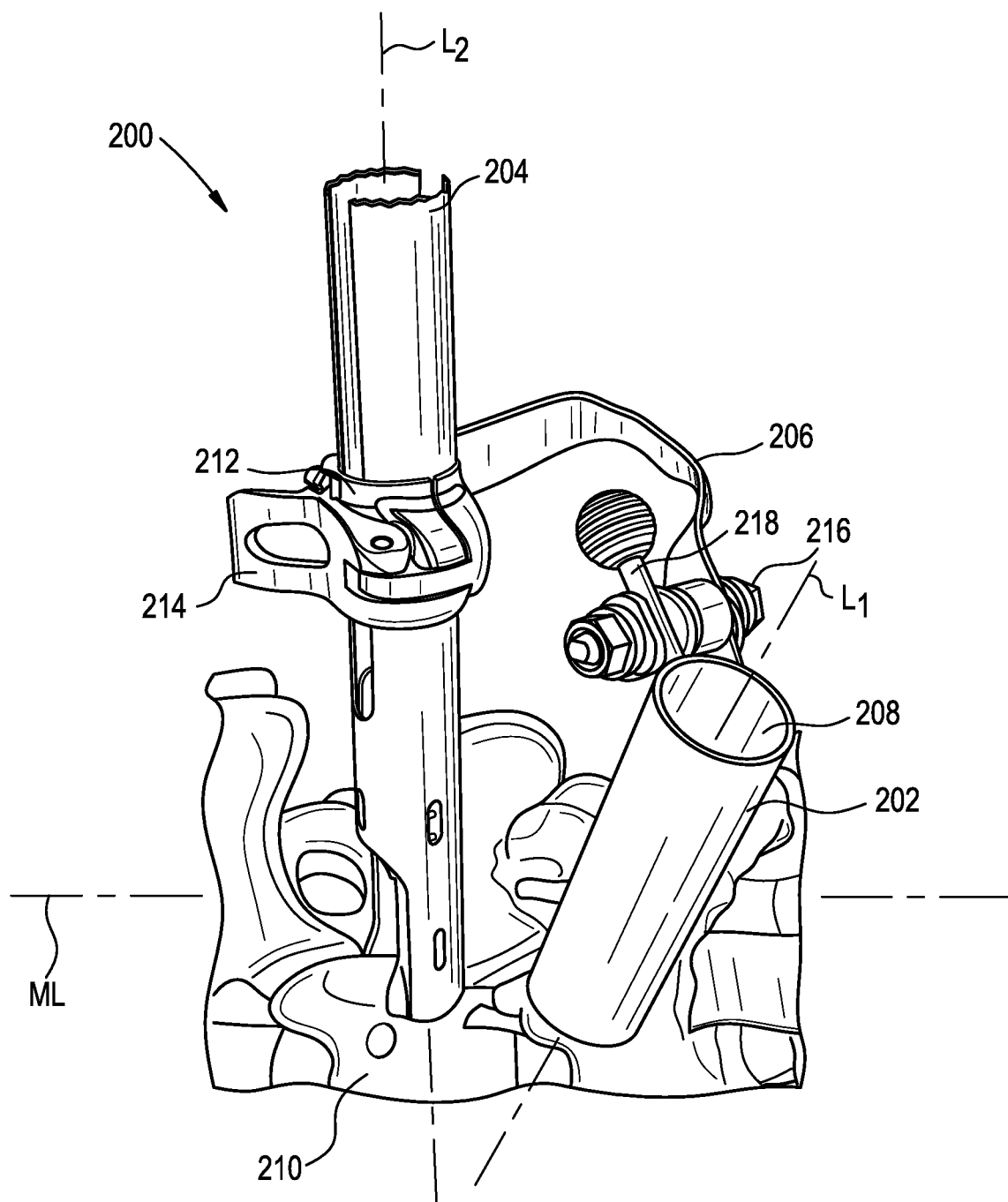
FIG. 2 is a front perspective view of one embodiment of a surgical system including a deformable linkage to adjust a position of an access port.
Figure 3:
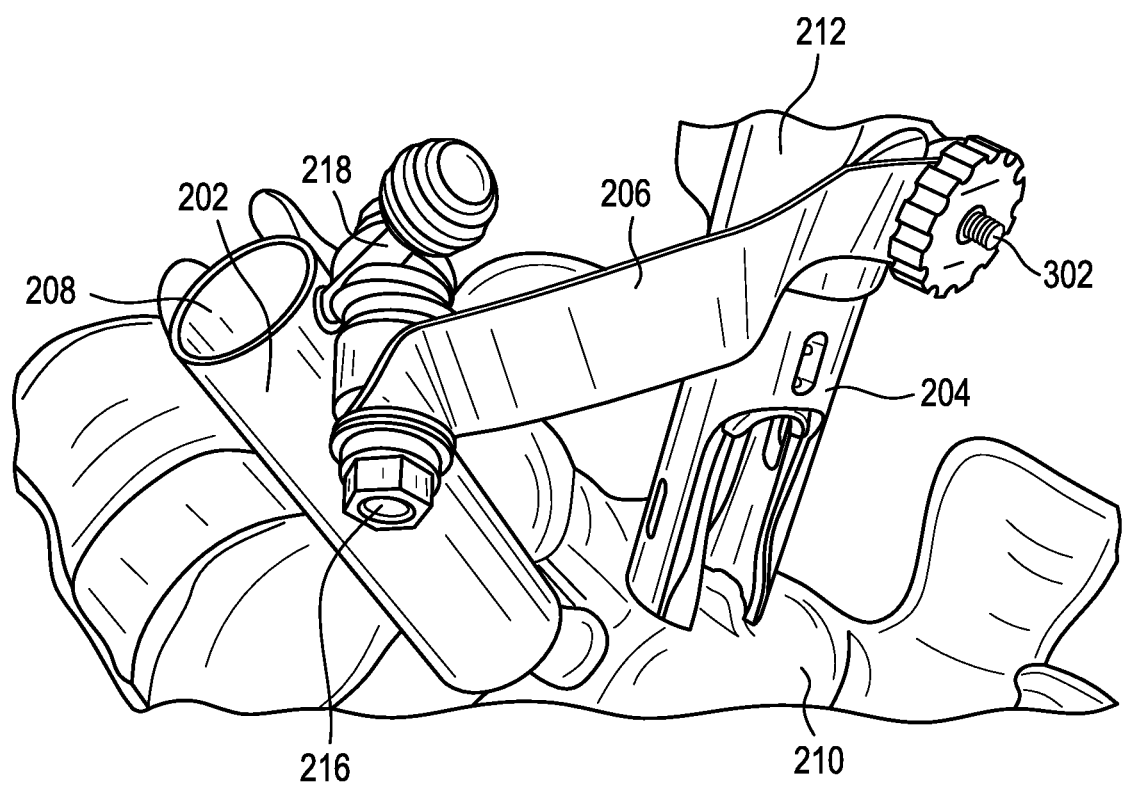
FIG. 3 is a side perspective view of the surgical system of FIG. 2.

FIGS. 2 and 3 illustrate one embodiment of a system 200 that includes an access port 202 that is coupled to an extension tower 204 by a deformable linkage 206. The access port or device 202 can have a generally cylindrical shape with an inner lumen 208 through which any of a variety of surgical instruments can be passed. The access port 202 can have any of a variety of sizes, including inner lumen diameters, lengths, sidewall thicknesses, etc. based on intended use (e.g., size of surgical site being accessed through the port, location relative to a patient's body, etc.). Further, the access port 202 can be formed from any of a variety of materials, including metals such as stainless steel and titanium, as well as various polymers.

The extension tower 204 shown in FIGS. 2 and 3 can be configured to couple to, for example, a bone screw or anchor implanted in a patient's spine 210 (anchor not shown). For example, the extension tower 204 can be configured to couple with a proximal end of a mono- or poly-axial receiver head that is coupled to a proximal portion of a bone anchor. While not shown in FIGS. 2 and 3, such bone anchor assemblies are known in the art and described, for example, in U.S. application Ser. No. 15/208,872 filed on Jul. 13, 2016 and entitled "Bone Anchor Assemblies And Related Instrumentation," now issued as U.S. Pat. No. 10,463,402, the entire contents of which are incorporated by reference herein. Moreover, the extension tower 204 can be any of a variety of such towers known in the art, including, for example, one of the towers described in U.S. Pat. No. 7,179,261 entitled "Percutaneous Access Devices And Bone Anchor Assemblies," the entire contents of which is incorporated by reference herein.

The access port 202 can be coupled to the extension tower 204 by a deformable linkage 206 that can include a length of metal or otherwise deformable material sufficiently rigid to maintain its position in the absence of force applied by a user. Moreover, the linkage 206 can couple to the extension tower 204 via a sleeve 212 disposed about an outer circumference of the tower. The sleeve 212 can include a cam lever 214 or other locking mechanism that can allow the sleeve to be selectively locked to the extension tower 204. This can allow the sleeve to be positioned at any of a variety of heights relative to the extension tower 204. In certain embodiments, the sleeve 212 can also be configured to selectively lock against rotation about the extension tower 204 with actuation of the cam lever 214.

The linkage 206 can be coupled at each end to one of the access port 202 and the extension tower 204 via any of a variety of clamping mechanisms known in the art. For example, in the illustrated embodiment a clamping assembly 216 including a bolt and a plurality of nuts is utilized to couple one end of the linkage 206 to an extension post 218 extending from a sidewall of the access port 202. An opposite end of the linkage 206 can be coupled to the sleeve 212 using a similar assembly 302 including a bolt and a thumbscrew. Such mechanisms can provide selective locking ability similar to the cam lever 214, such that the positions of the various components relative to one another can be adjusted prior to securing any of the cam lever 214, clamping assembly 216, and thumbscrew assembly 302. After tightening of each of these mechanisms, adjusting a position of the access port 202 relative to the extension tower 204 can require applying a force sufficient to deform the linkage 206.

As shown in FIG. 2, the access port 202 can be positioned such that a longitudinal axis $L_1$ of the access port is non-coaxial with a longitudinal axis $L_2$ of the extension tower 204, or a longitudinal axis of any anchor to which the extension tower is coupled. For example, the axis $L_1$ can be offset from and/or obliquely angled with respect to the axis $L_2$. As shown in FIG. 2, for example, the access port 202 can provide access to a surgical site, such as an intervertebral disc space or a vertebra adjacent to the vertebra to which the extension tower 204 is coupled on an ipsilateral side (e.g., a same side relative to a patient's spinal or midline axis ML) relative thereto.

Figure 4:
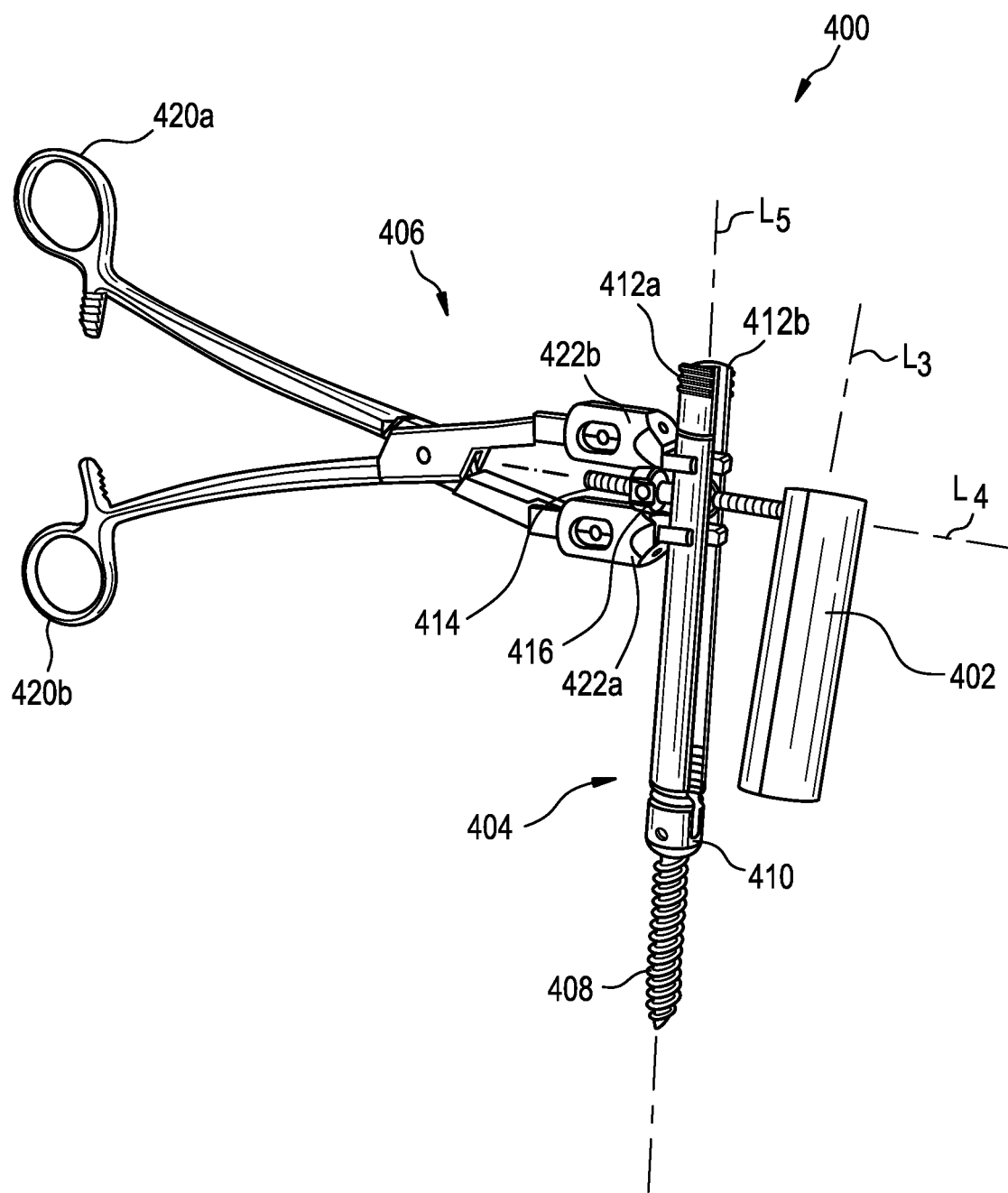
FIG. 4 is a front perspective view of one embodiment of a surgical system including opposed extensions coupled to an anchor that selectively compress to lock a position of an access port.
Figure 5:
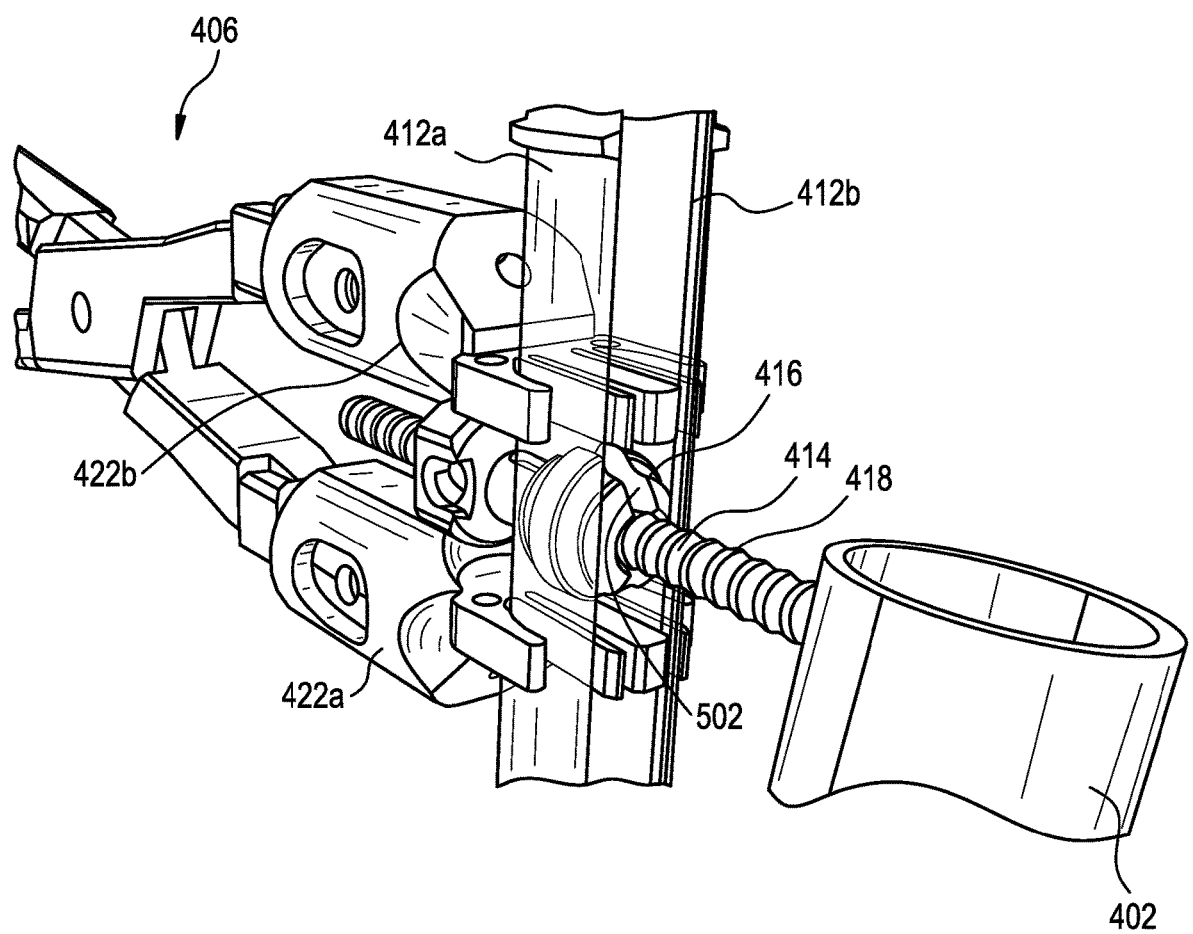
FIG. 5 is a partially-transparent detail view of the system of FIG. 4.
Figure 6:
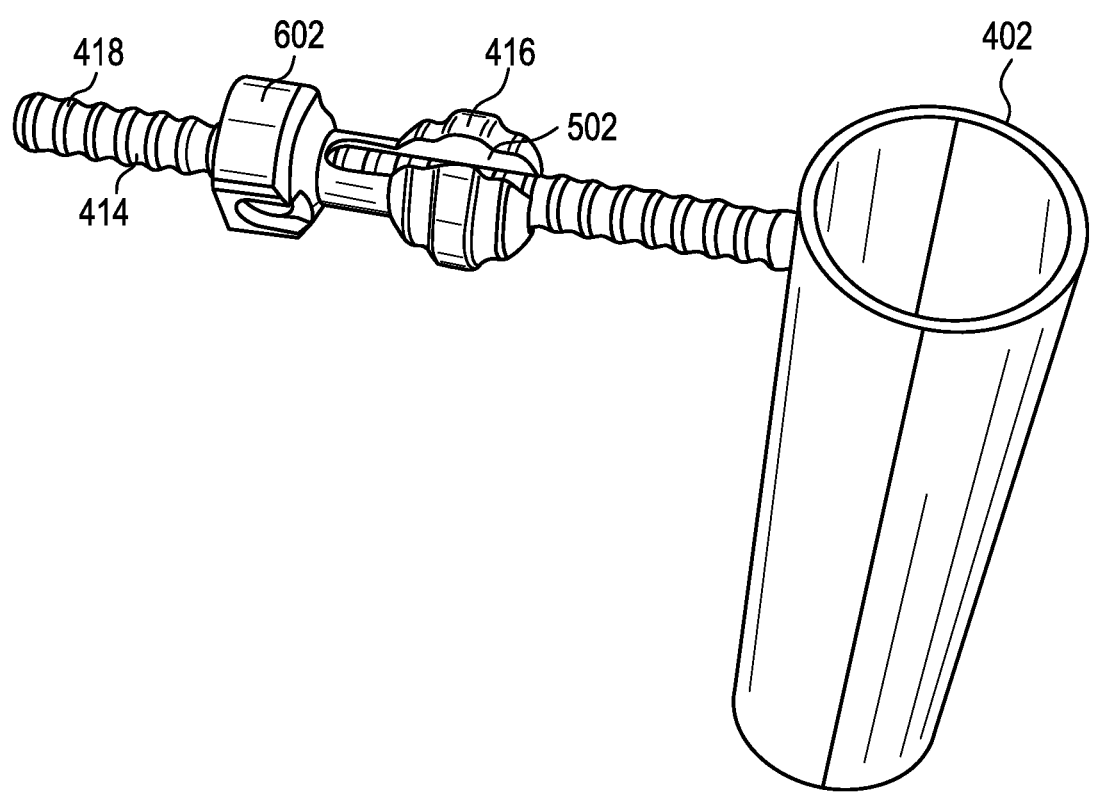
FIG. 6 is a top perspective view of an access port of the system of FIG. 4.
Figure 7:
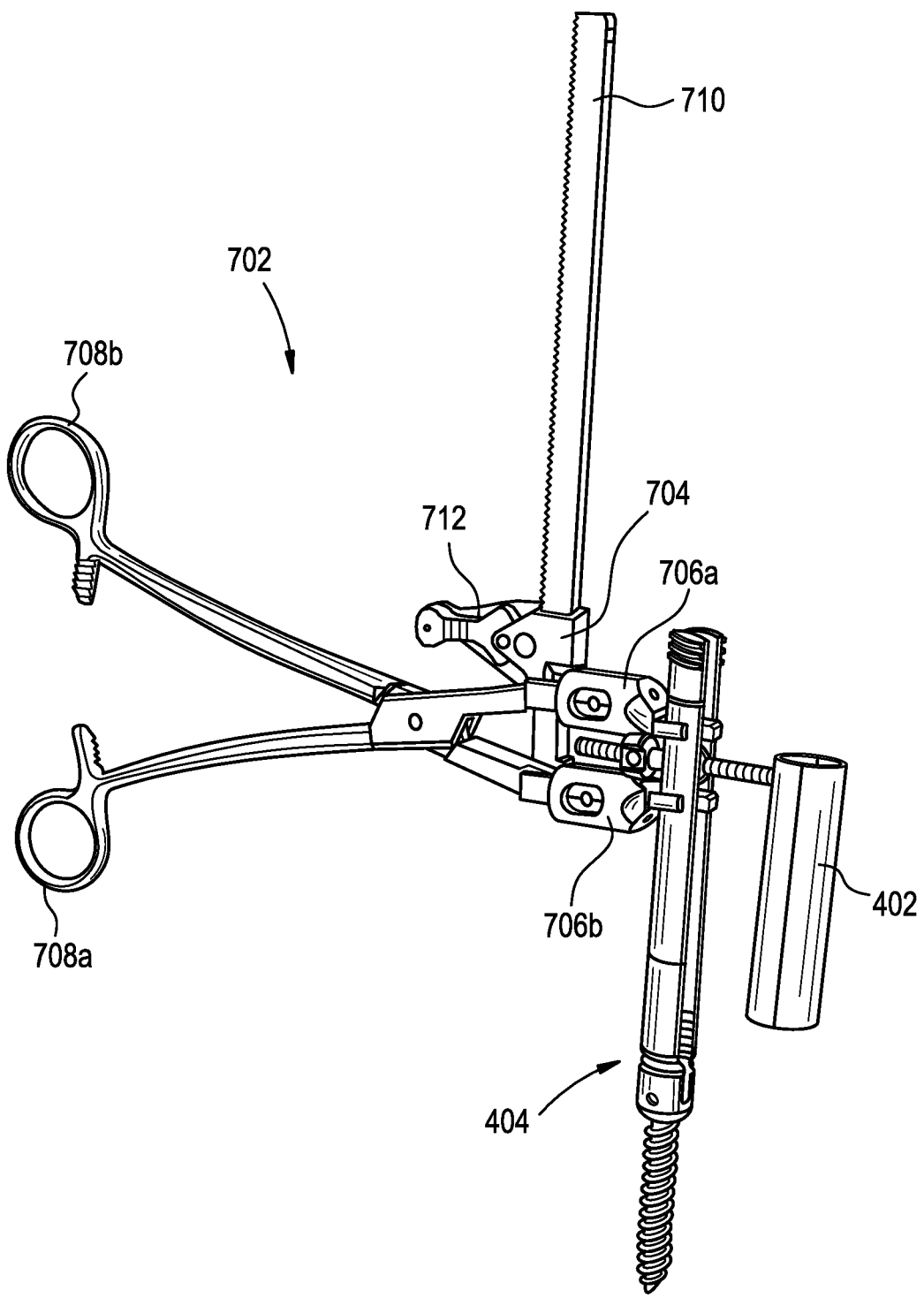
FIG. 7 is a front perspective view of one embodiment of a surgical system including a ratchet clamp.

FIGS. 4-12C illustrate embodiments of a system that utilizes extension tabs that extend proximally from a distal portion of an anchor to capture and selectively lock a position of an access port. As shown in FIGS. 4-6, a first embodiment of such a system 400 can include an access port 402 coupled to an anchor assembly 404 and a locking instrument 406 (e.g., forceps) configured to selectively lock a position of the access port relative to the anchor assembly. In the illustrated embodiment, the anchor assembly 404 is a polyaxial pedicle screw that includes a shank 408 configured for insertion into a patient's bone, as well as a receiver head 410 coupled to a proximal portion of the shank. The receiver head 410 can include extension tabs 412a, 412b that extend proximally from opposed arms of the receiver head. The extension tabs 412a, 412b can be integrally formed with the receiver head 410, or in other embodiments can be coupled thereto via any of a variety of attachment mechanisms.

The access port 402 can include a shaft 414 or other mating feature integrally formed therewith or coupled thereto and extending transversely or radially away therefrom such that a longitudinal axis $L_3$ of the access port and a longitudinal axis $L_4$ of the shaft are transverse or oblique to one another. The shaft 414 can be integrally formed with the access port 402 or can be coupled to the access port 402 via a clamp or other connecting mechanism. In some embodiments, the shaft 414 can be threaded or have a series of repeating surface features 418, such as ridges or ribs, to locate a split ball 416 or other locking element along a length thereof.

The split ball 416 can be positioned around the shaft 414 and disposed between the extension tabs 412a, 412b, as shown in the detail view of FIGS. 5 and 6. A relief slot 502 formed in the ball can allow its adjustment along a length of the shaft 414 by, e.g., translational sliding movement, rotation along threads 418 of the shaft 414, etc. The split ball 416 can move polyaxially relative to the extension tabs 412a, 412b in the absence of pressure being applied to the tabs by, e.g., the locking instrument 406, including sliding along a length of the extension tabs and rotating to adjust its orientation relative to the tabs. Once a desired position of the ball 416 relative to the shaft 414 and the extension tabs 412a, 412b is achieved, the locking instrument 406 can be actuated to urge the extension tabs toward one another, thereby clamping the split ball between the extension tabs. More particularly, in the illustrated embodiment, user actuation to bring the locking instrument handles 420a, 420b toward one another can cause distal arms 422a, 422b to move toward one another and slide along a length of the extension tabs 412a, 412b. This movement of the distal arms 422a, 422b can urge the extension tabs 412a, 412b toward one another, thereby imparting a compressive force on the split ball 416 disposed therebetween. This compressive force can prevent polyaxial movement of the split ball 416 relative to the extension tabs 412a, 412b, thereby locking a position of the ball relative to the extension tabs. Further, the compressive force can also urge opposed portions of the split ball separated by the relief slot 502 toward one another, thereby clamping the ball to the shaft 414 and preventing relative movement between these components. As a result, actuation of the locking instrument can selectively lock a position and orientation of the access port 402 relative to the anchor assembly 404.

As with the prior embodiments described above, the extension of the shaft 414 or other mating feature laterally, radially, or transversely away from the access port 402, in combination with the split ball 416 positioned along a length thereof, can allow the access port 402 to be positioned and selectively locked such that a longitudinal axis $L_3$ of the access port and a longitudinal axis $L_5$ of the anchor assembly 404 are non-coaxial. For example, the access port 402 can be positioned to access a surgical site adjacent to the anchor assembly 404 on an ipsilateral side of a patient's body.

Figure 8:
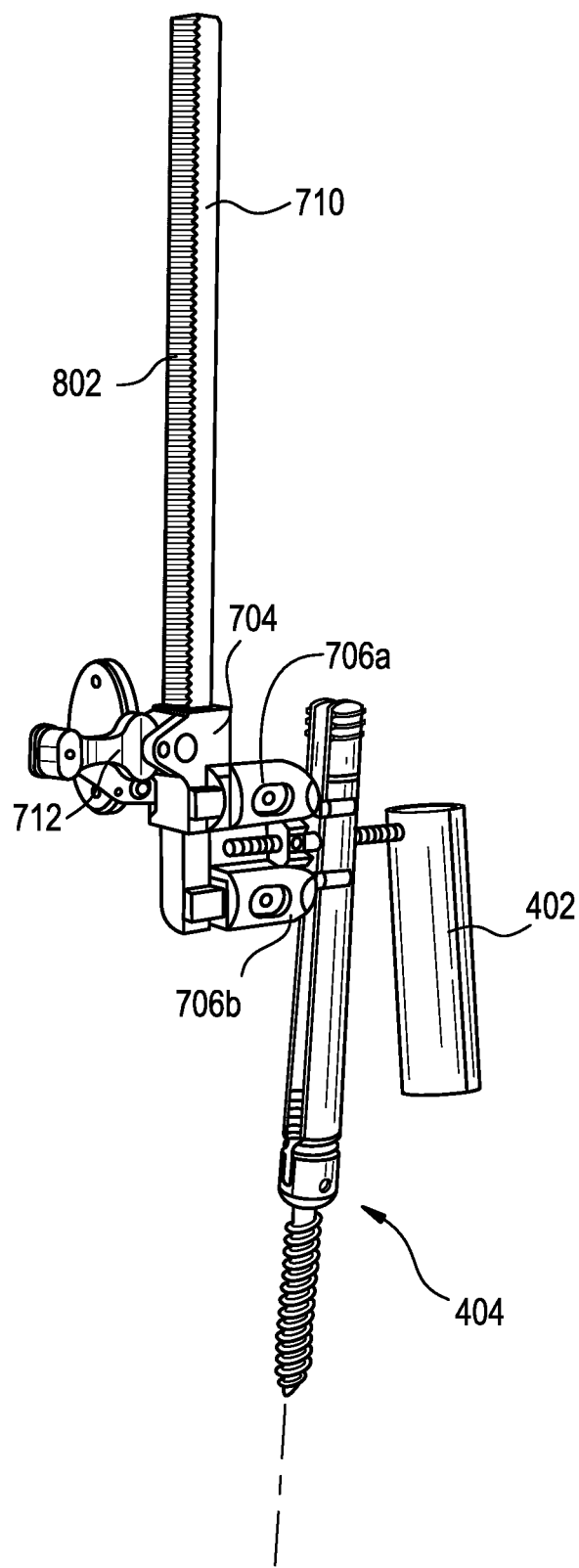
FIG. 8 is a rear perspective view of the system of FIG. 7 after removal of a clamping instrument.

There are a variety of different mechanisms possible to accomplish the selective clamping of the extension tabs 412a, 412b to lock a position of the access port 402 relative to the anchor assembly 404. In the embodiment of FIGS. 4 and 5, for example, the locking instrument 406 can directly contact the extension tabs 412a, 412b via distal arms 422a, 422b. In such an embodiment, release of the handles 420a, 420b can release pressure on the extension tabs 412a, 412b, thereby releasing the lock of the split ball 416 and access port 402. In another embodiment shown in FIGS. 7 and 8, however, a locking instrument 702 can include a ratcheting clamp 704 that can maintain a position of distal arms 706a, 706b to maintain the position lock of the access port 402 relative to the anchor assembly 404 even if a user releases the instrument handles 708a, 708b. Indeed, the instrument handles 708a, 708b can be configured to be separated from the ratchet clamp 704 after actuation, such that a more streamlined or low-profile assembly is left that includes the distal arms 706a, 706b and ratchet clamp 704, as shown in FIG. 8.

The ratchet clamp 704 can include a ratchet track 710 having a plurality of teeth 802 formed thereon, as well as a pawl 712 configured to engage the teeth to allow for movement of the distal arms 706a, 706b toward one another but resist opposite movement of the arms away from one another. A release can be included to disengage the pawl 712 from the ratchet track 710 and allow unlocking of the access port 402 relative to the anchor assembly 404.

Figure 9:
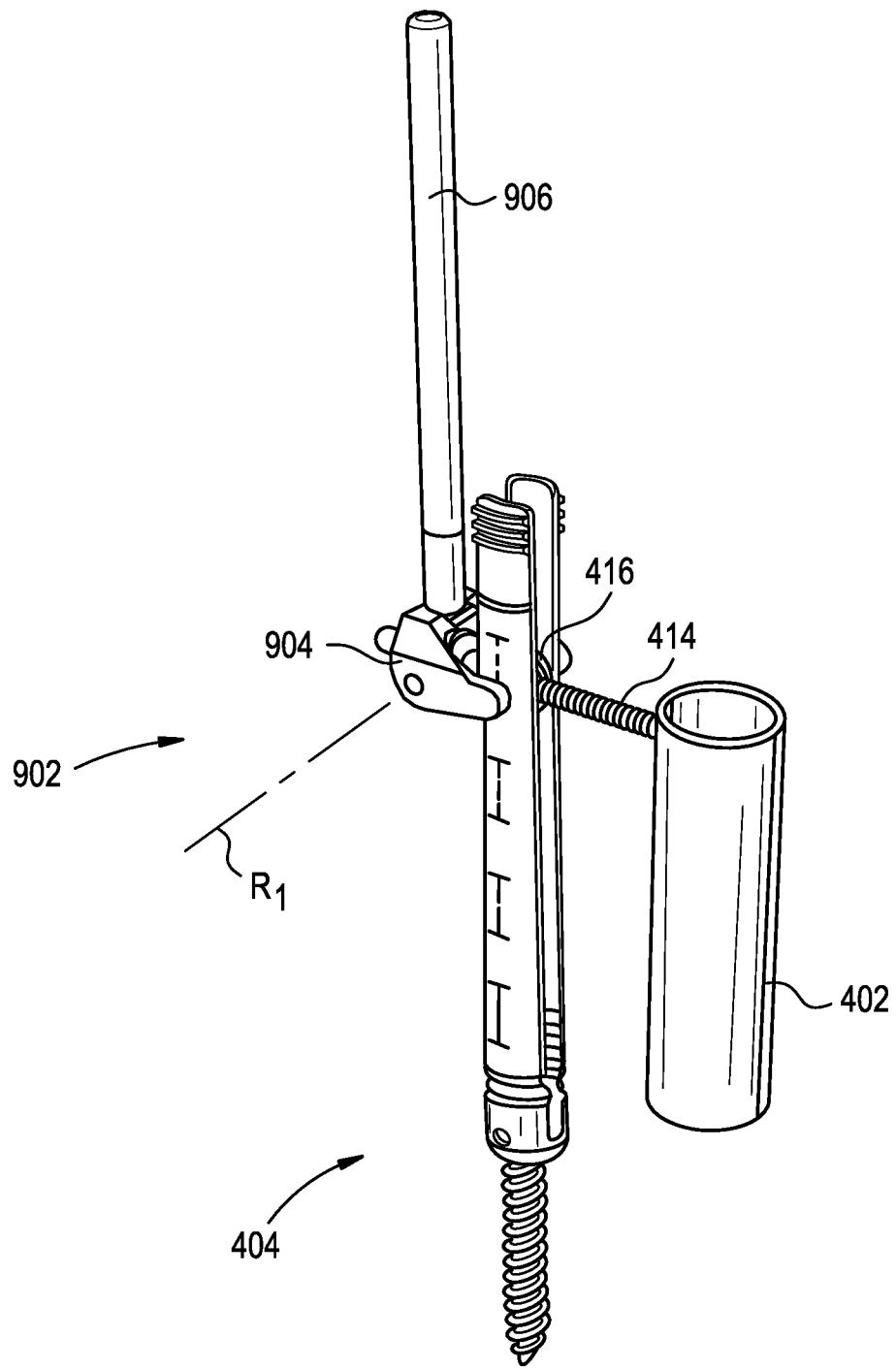
FIG. 9 is a front perspective view of one embodiment of a surgical system including a pivoting lever clamp.
Figure 10:
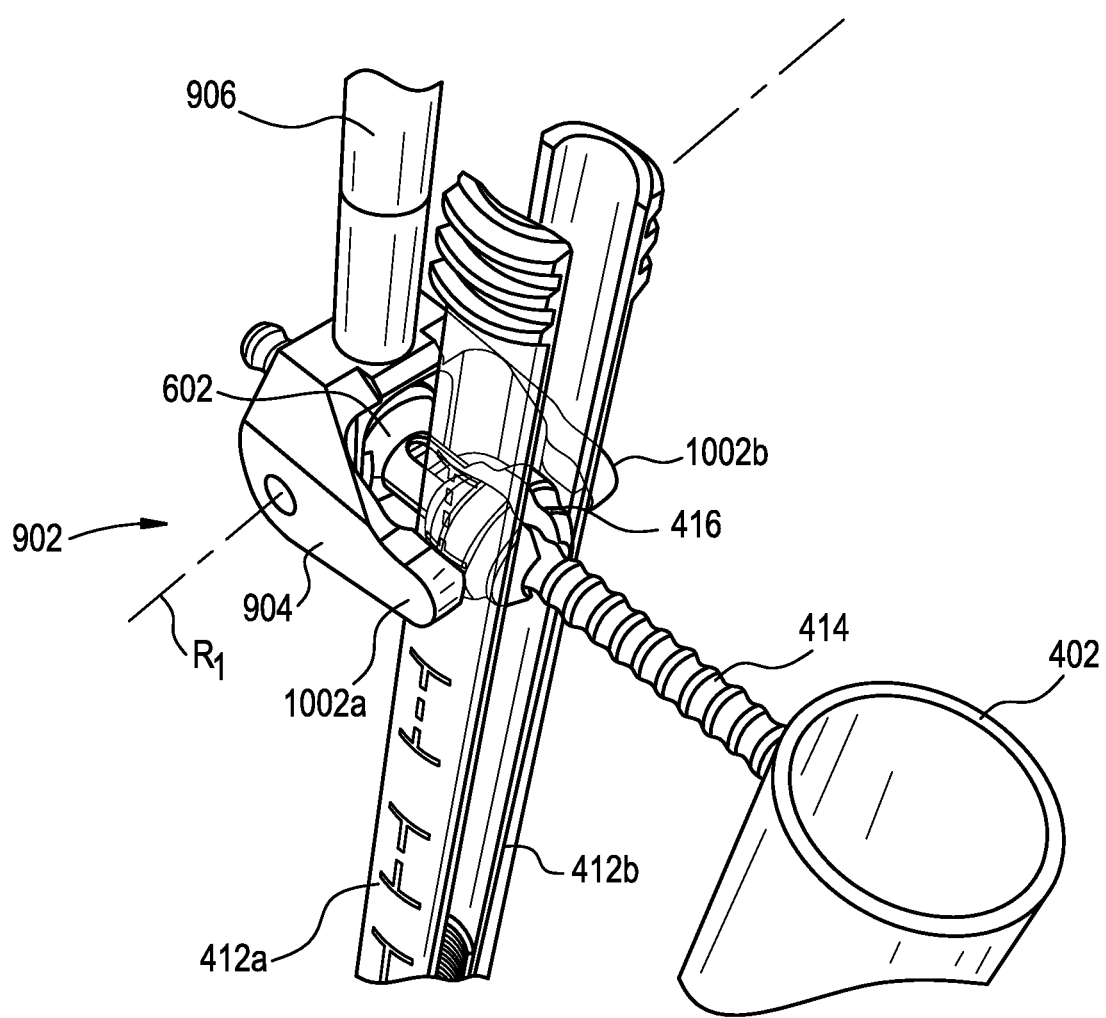
FIG. 10 is a detail view of the system of FIG. 9.

In another embodiment illustrated in FIGS. 9 and 10, a clamp 902 can replace the locking instruments 406 and 702 described above. The clamp 902 can include a body 904 pivotably coupled to a proximal portion 602 of the split ball 416 such that the body 904 can rotate relative to the split ball 416 about an axis $R_1$. A fork including a pair of arms 1002a, 1002b can extend from the body 904 and be configured to contact and slide along outer surfaces of the extension tabs 412a, 412b as the clamp body 904 and arms are rotated toward the extension tabs. The arms 1002a, 1002b can apply a compressive force to the opposed extension tabs 412a, 412b in the same manner as the distal arms 422a, 422b and 706a, 706b described above such that a position of the access port 402 can be locked relative to the anchor assembly 404. Again, such locking is accomplished by urging the extension tabs 412a, 412b toward one another to impart a compressive force on the split ball 416 and prevent relative movement between the split ball and the extension tabs. Such compression can also cause opposed portions of the split ball 416 to compress into the shaft 414, thereby preventing relative movement between the split ball and the shaft. These dual locking functions can effectively prevent relative movement between the access port 402 and the anchor assembly 404.

A handle 906 can extend from the body 904 to provide a user with leverage when actuating the lock by rotating the body 904 and arms 1002a, 1002b toward the extension tabs 412a, 412b. In some embodiments, the handle 906 can be configured to threadingly or otherwise removably couple to the body 904 such that the handle can be removed after actuation to allow for a more streamlined or low-profile assembly once a position of the access port 402 is locked.

Figure 11:
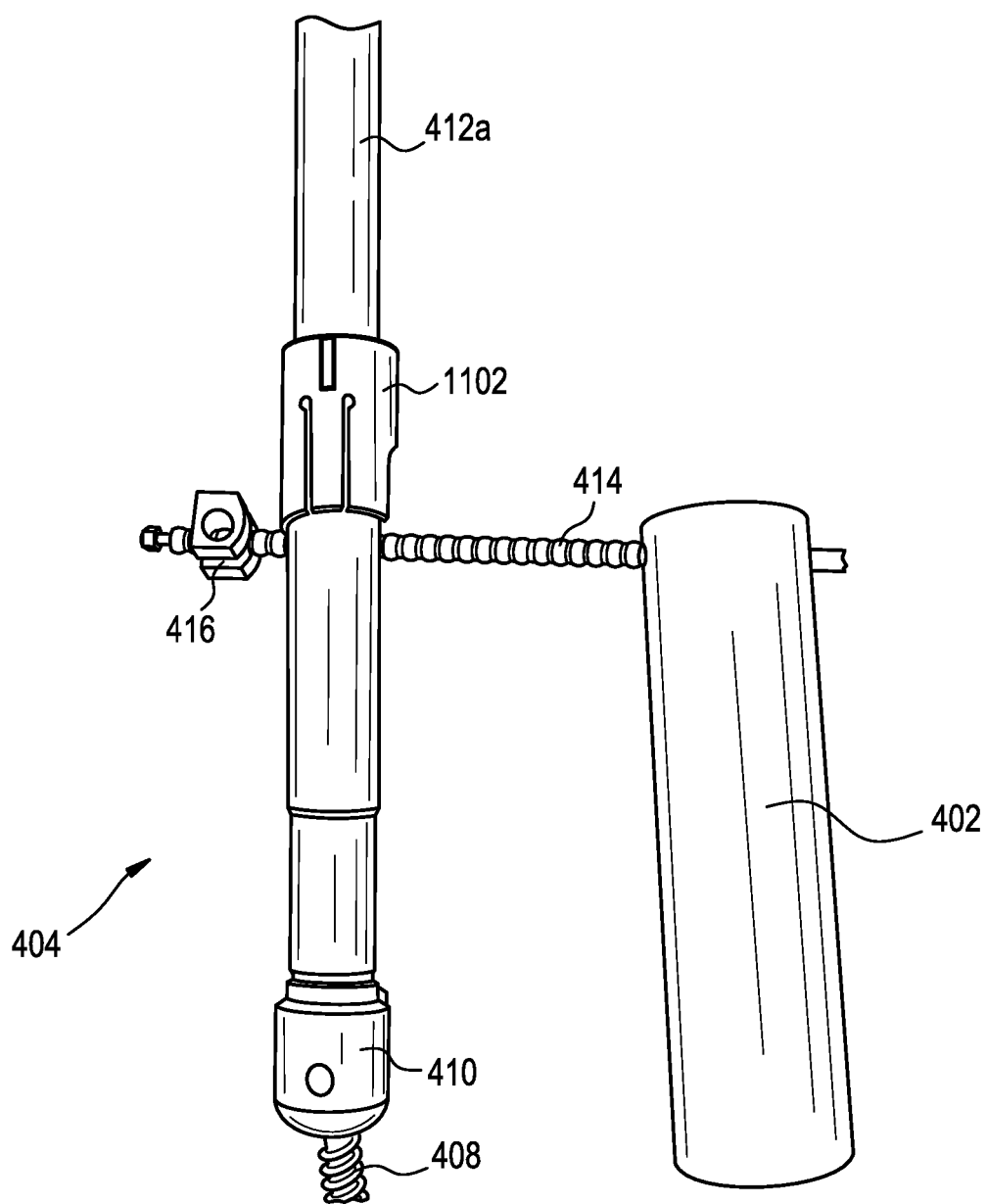
FIG. 11 is a side view of one embodiment of a surgical system including a sliding ring clamp.
Figure 12A:
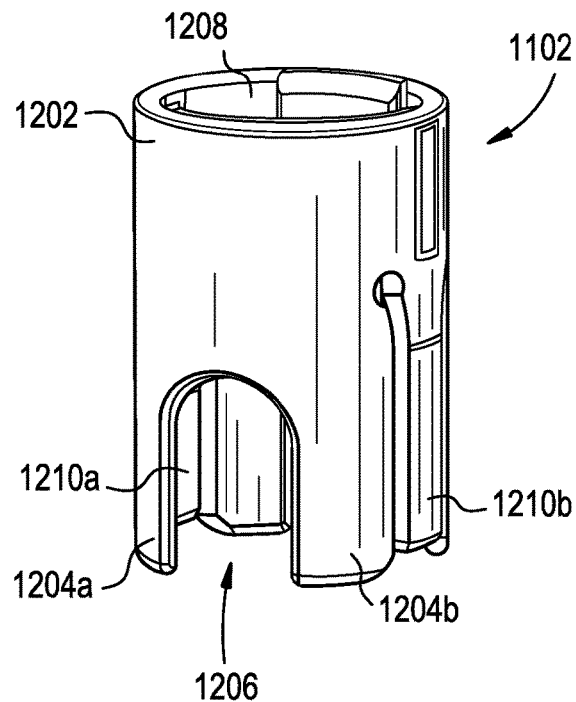
FIG. 12A is a front perspective view of the sliding ring clamp of FIG. 11.
Figure 12B:
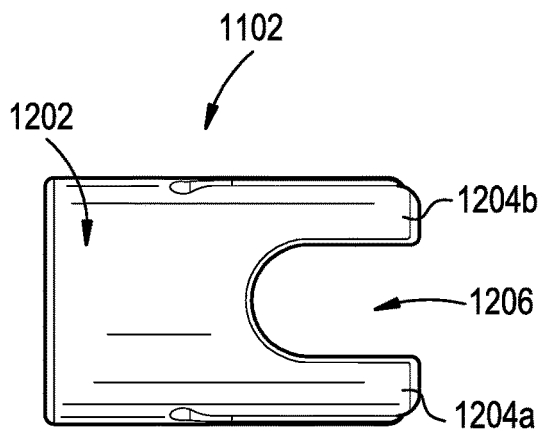
FIG. 12B is a front view of the sliding ring clamp of FIG. 11.
Figure 12C:
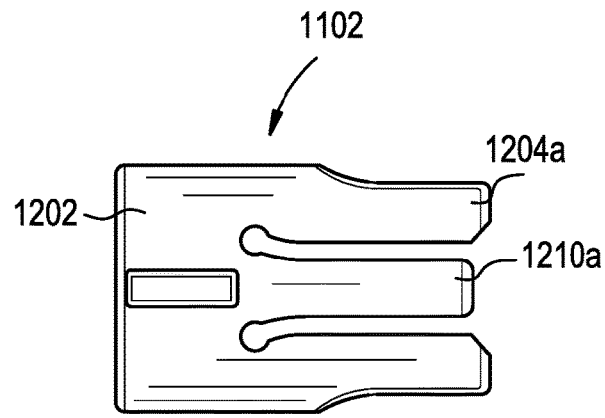
FIG. 12C is a side view of the sliding ring clamp of FIG. 11.

In still another embodiment shown in FIGS. 11-12C, a ring lock 1102 can be employed in place of the locking instruments described above. The ring lock 1102 can be slidably disposed over the extension tabs 412a, 412b such that it can translate along a length thereof. The ring lock 1102 can include a closed proximal portion 1202 defining an inner lumen 1208 through which the extension tabs 412a, 412b can extend. The ring lock 1102 can further include opposed sets of distally extending arms 1204a, 1204b that can define a U-shaped recess 1206 that can receive the shaft 414 as the ring lock is translated into position around the extension tabs 412a, 412b and the split ball 416.

In some embodiments, the diameter of the inner lumen 1208 can be smaller than the resting outer diameter of the extension tabs 412a, 412b such that the ring lock 1102 applies a compressive force to the extension tabs as it is translated along the extension tabs. In other embodiments, the inner diameter of the ring lock 1102 can be tapered such that a compressive force is applied by the distal arms 1204a, 1204b but not the proximal portion 1202. In still other embodiments, the ring lock 1102 can include opposed spring arms 1210a, 1210b that can be configured to impart a compressive force on the extension tabs 412a, 412b and thereby permit the above-described selective locking as the ring lock 1102 is slid into position over the extension tabs 412a, 412b and split ball 416. Such spring arms 1210a, 1210b can be utilized in place of, or in addition to, different inner lumen diameters to exert varying compressive forces on the extension tabs 412a, 412b and split ball 416.

FIGS. 13A-18 illustrate still other examples of linkages or mating features that can couple an access port to an anchor to define a channel to a surgical site, for example a surgical site located on an ipsilateral side of a patient's body as the anchor. More particularly, these figures illustrate various embodiments of selectively lockable and polyaxially adjustable linkages. FIGS. 13A and 13B, for example, illustrate one embodiment of a polyaxially adjustable linkage 1302 that can be selectively locked via a bolt and thumbscrew 1304 that compresses opposed body portions of the linkage together, thereby compressing a first connection at one end of the linkage to an access port 1306 and a second connection at an opposite end of the linkage to an extension tower 1308 that can be coupled to, for example, a pedicle screw or other anchor (not shown). By varying the tightness of the thumbscrew 1304, movement of the access port relative to the extension tower 1308 can be selectively permitted. Further, because the linkage 1302 is capable of polyaxial adjustment relative to each of the access port 1306 and tower 1308, the access port can be polyaxially adjusted relative to the tower, as shown in the various relative positions of these components in FIGS. 13A and 13B.

Figure 14:
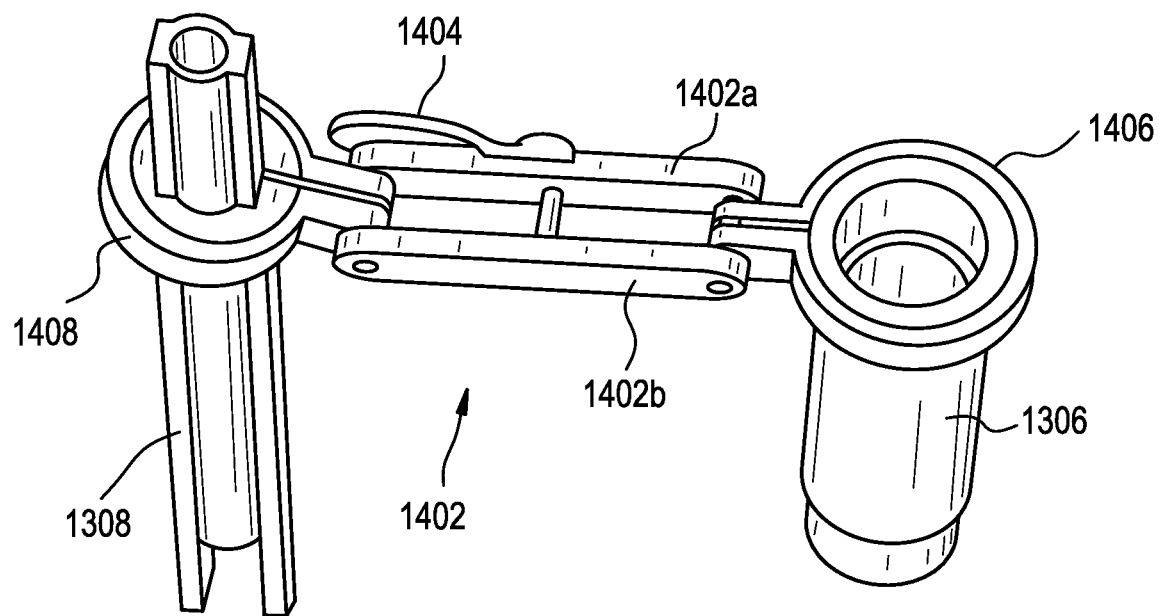
FIG. 14 is a top perspective view of one embodiment of a surgical system including an adjustable linkage.
Figure 15:
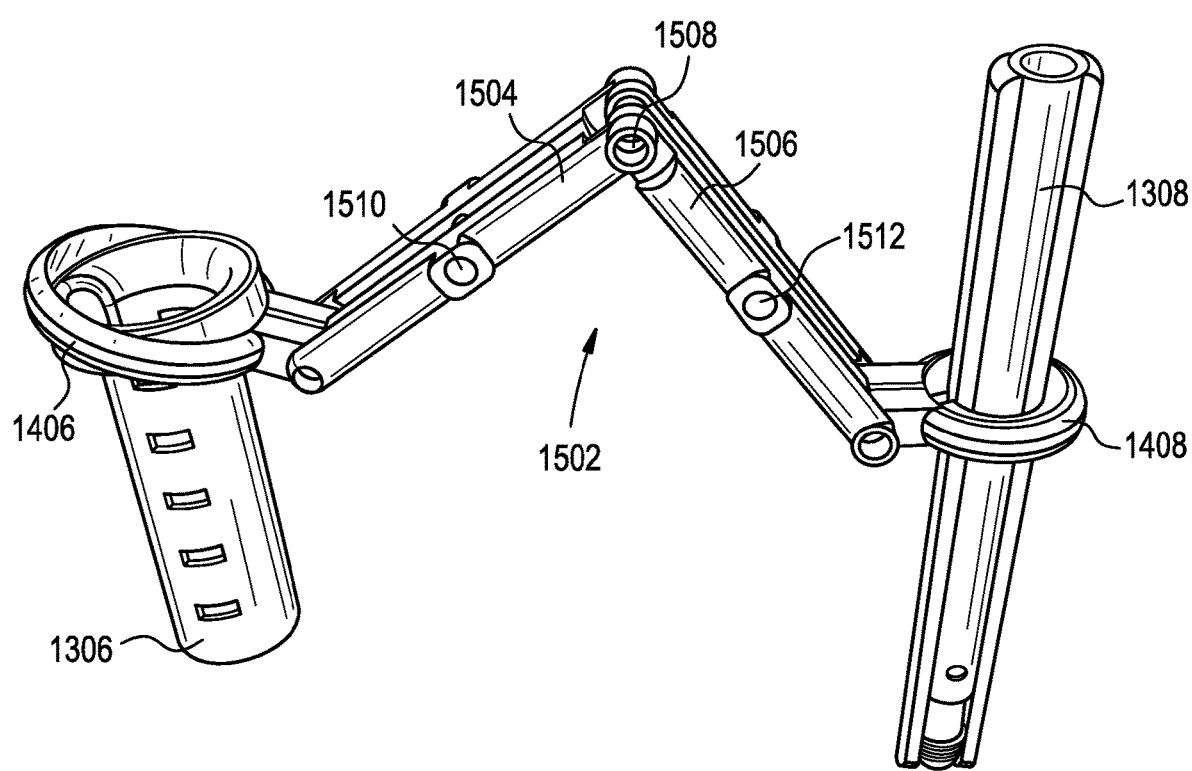
FIG. 15 is a top perspective view of one embodiment of a surgical system including an adjustable linkage.
Figure 16:
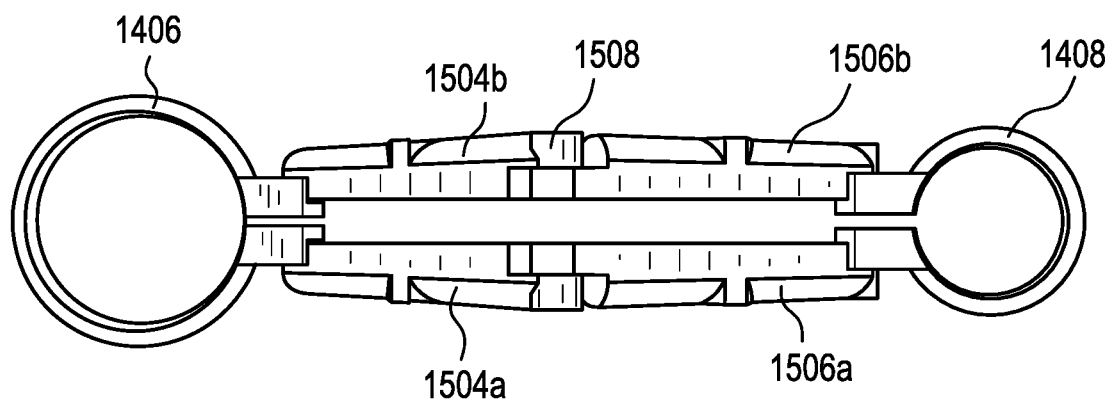
FIG. 16 is a top view of the system of FIG. 15.

While a thumbscrew 1304 is illustrated in FIGS. 13A and 13B, a variety of other locking mechanisms can be employed to selectively permit or prevent relative movement between the access port 1306 and tower 1308. For example, FIG. 14 illustrates an embodiment in which a cam 1404 is employed to selectively compress opposed portions of the linkage 1402a, 1402b to selectively lock a position of the access port 1306 relative to the extension tower 1308. Still further, in some embodiments a linkage can include a plurality of rigid segments, as shown in FIGS. 15 and 16. For example, a linkage 1502 can include a first segment 1504 coupled to the access port 1306 and a second segment 1506 coupled to the extension tower 1308. The first and second segments 1504, 1506 can be pivotably coupled to one another at a pivot joint 1508. Such a configuration can allow for greater flexibility and reach in positioning the access port 1306 relative to the extension tower 1308. For example, the linkage 1502 of FIG. 15 can be positioned to extend over or around other instrumentation disposed between the access port 1306 and the extension tower 1308. Any number of linkage segments can be included and each segment can receive a locking mechanism, e.g., a thumbscrew, cam-lock, or other locking mechanism to selectively lock movement of components coupled thereto by compressing opposed portions 1504a, 1504b or 1506a, 1506b together. In the illustrated embodiment, for example, first and second segments 1504, 1506 include through-holes 1510, 1512 to receive a thumbscrew or cam-lock mechanism, as shown in FIGS. 13A-14.

Figure 17:
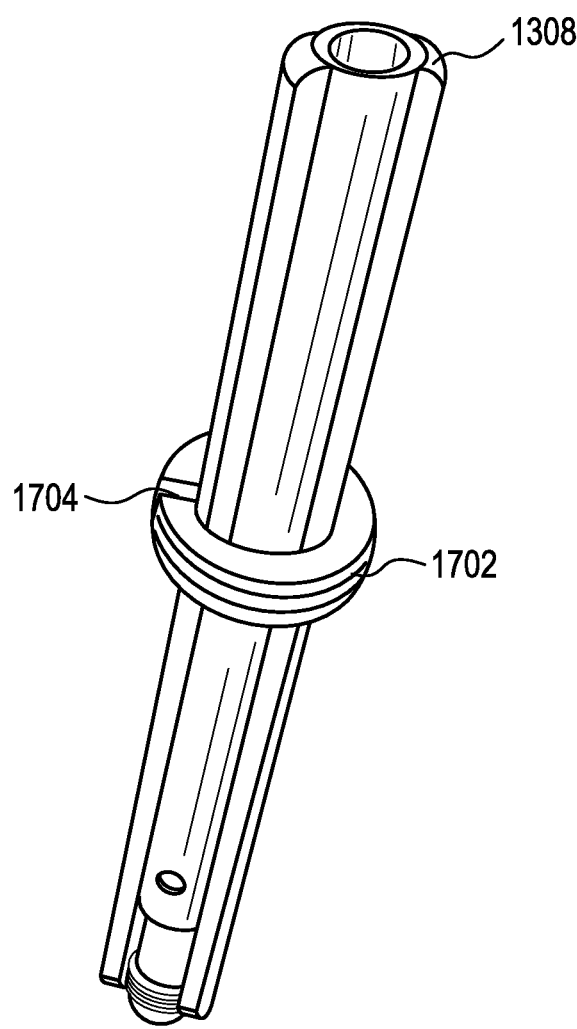
FIG. 17 is a perspective view of the anchor of FIG. 15.
Figure 18:
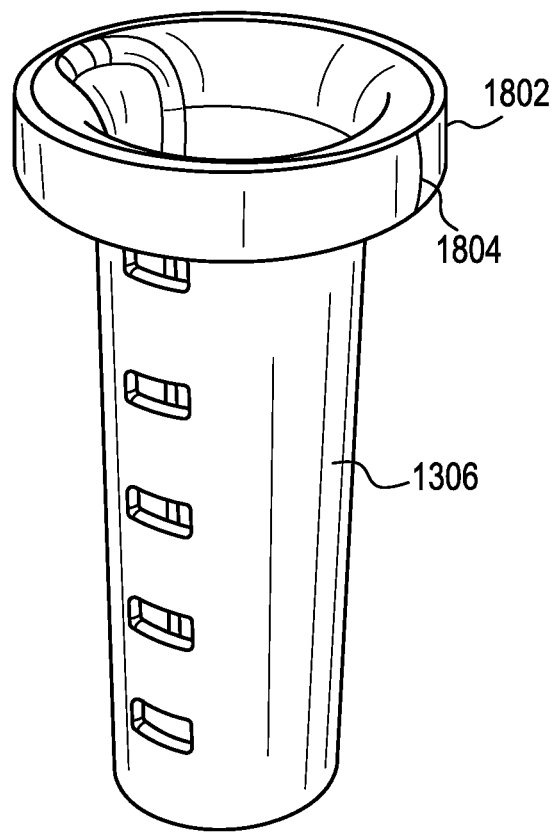
FIG. 18 is a perspective view of the access port of FIG. 15.

The embodiments illustrated in FIGS. 13A-16 can couple to an access port 1306 and extension tower 1308 using, e.g., a split ring clamp. For example, the linkage 1402 of FIG. 14 can include a first split ring clamp 1406 disposed about the access port 1306 and a second split ring clamp 1408 disposed about the extension tower 1308. The split ring clamps 1406, 1408 can include spherical inner surfaces that can interface with spherical outer surfaces of bushing rings coupled to the access port 1304 and extension tower 1308. For example, FIG. 17 illustrates one embodiment of a bushing ring 1702 coupled to the extension tower 1308 and FIG. 18 illustrates one embodiment of a bushing ring 1802 coupled to the access port 1306. The bushing rings 1702, 1802 can include outer spherical surfaces and a relief slot 1704, 1804 to allow the bushing rings to slide along and/or rotate about the extension tower 1308 and access port 1306 when no clamping force is exerted thereon. The ability to selectively move the bushing rings 1702, 1802 relative to the extension tower 1308 and access port 1306 can allow, for example, a height of the access port relative to the extension tower to be adjusted. In other embodiments, however, the bushing rings 1702, 1802 can be integrally formed with the extension tower 1308 and access port 1306 such no relative movement between these components is possible. In such embodiments, the relief slots 1704, 1804 may be eliminated.

The interfacing of the inner and outer spherical surfaces of the split ring clamps 1406, 1408 and bushing rings 1702, 1802 can allow for polyaxial movement between the components in the absence of compressive force. When compressive force is applied to the split ring clamps 1406, 1408 via, for example, the thumbscrew 1304 or cam-lock 1404, the split ring clamps 1406, 1408 can compress around the bushing rings 1702, 1802, thereby causing the bushing rings to compress around the access port 1306 and extension tower 1308 and prevent relative movement between these components. This can effectively lock the entire linkage to prevent relative movement between the access port 1306 and the extension tower 1308. In the multi-part linkage 1502 of FIGS. 15 and 16, it can be possible to selectively lock each segment 1504, 1506 of the linkage separately.

Figure 19A:
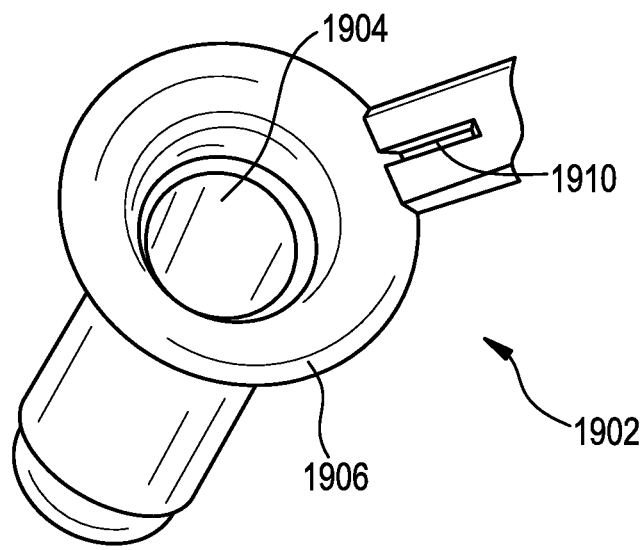
FIG. 19A is a perspective view of one embodiment of a telescoping access port.
Figure 19B:
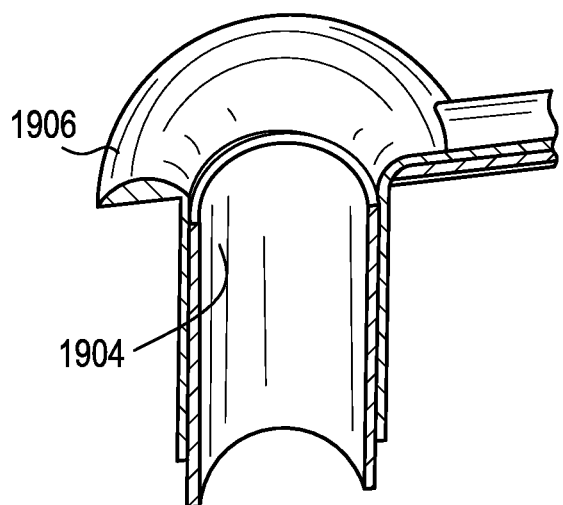
FIG. 19B is a perspective cross-sectional view of the telescoping access port of FIG. 19A.
Figure 19C:
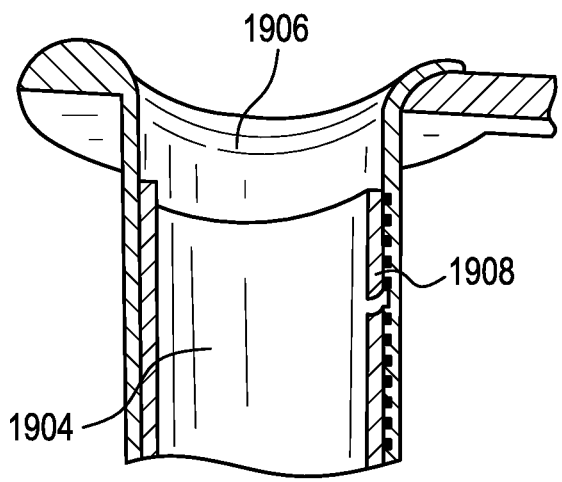
FIG. 19C is an alternative perspective cross-sectional view of the telescoping access port of FIG. 19A.

In some embodiments, a height of an access port can be adjustable such that the access port can be extend from a variety of heights above a patient's skin surface (e.g., positions along an extension tower or screw extension tabs, etc.) to various depths within a patient's body (e.g., to surgical sites located at various positions below a patient's skin surface). FIGS. 19A-19C illustrate one embodiment of an access port 1902 with an adjustable height achieved by relative movement of an inner tube or sleeve 1904 and an outer tube or sleeve 1906. More particularly, the inner tube 1904 can translate relative to the outer tube 1906. Such movement can be guided, in some embodiments, by various locating features 1908, such as cooperating ridges and notches, formed on the surfaces of the inner and outer tubes 1904, 1906. In some embodiments, a flat spring arm can be provided on the inner tube 1904 and the outer tube 1906 can include a plurality of teeth for engaging the spring arm. Moreover, in some embodiments relative movement of the inner and outer sleeves 1904, 1906 can be selectively locked to prevent further adjustment of a height of the access port. For example, a relief slot 1910 formed in the outer sleeve 1906 can allow the outer sleeve to be compressed around the inner sleeve 1904 to lock their relative positions when, for example, a split ring clamp, such as the clamp 1406, compresses around the outer sleeve 1906 or a bushing 1802 disposed about the outer sleeve 1906. Accordingly, in some embodiments a locking mechanism, such as the thumbscrew 1304 or the cam-lock 1404, can be utilized to lock both relative positions of an access port and an anchor, as well as a height of the access port.

FIGS. 20A-31D illustrate still other embodiments of access ports that can be coupled to an anchor, e.g., on an ipsilateral side of a patient's body, such that longitudinal axes of the access port and the anchor are non-coaxial. In the illustrated embodiments, however, a linkage coupling the anchor to the access port can form a portion of an outer circumference of the access port that pivots relative thereto. Such embodiments can be adjustable such that, in certain configurations, a longitudinal axis of the access port aligns with a longitudinal axis of the anchor. In certain procedures, such as spinal fixation or deformity correction procedures, this can advantageously allow the access port to also serve as a screw tower for spinal fixation rod insertion during a different portion of the procedure.

Figure 20A:
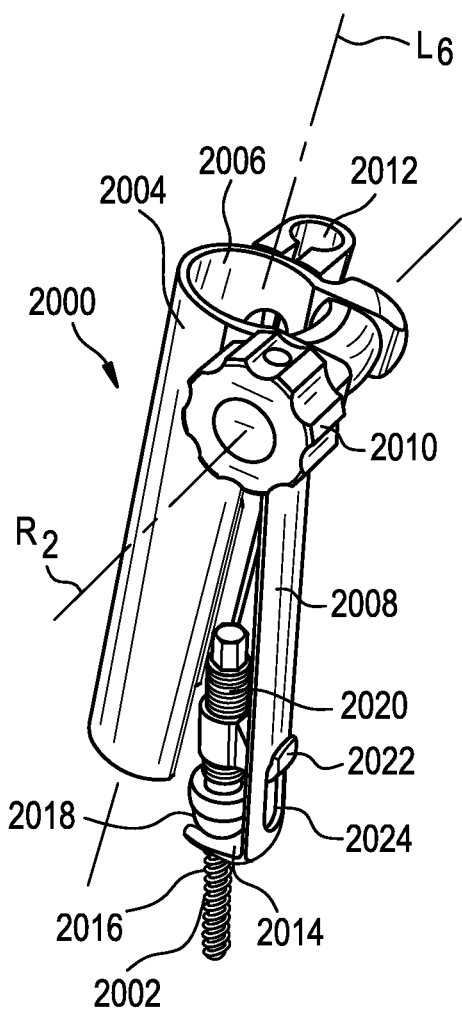
FIG. 20A is a perspective view of one embodiment of an access port coupled to an anchor.
Figure 20B:
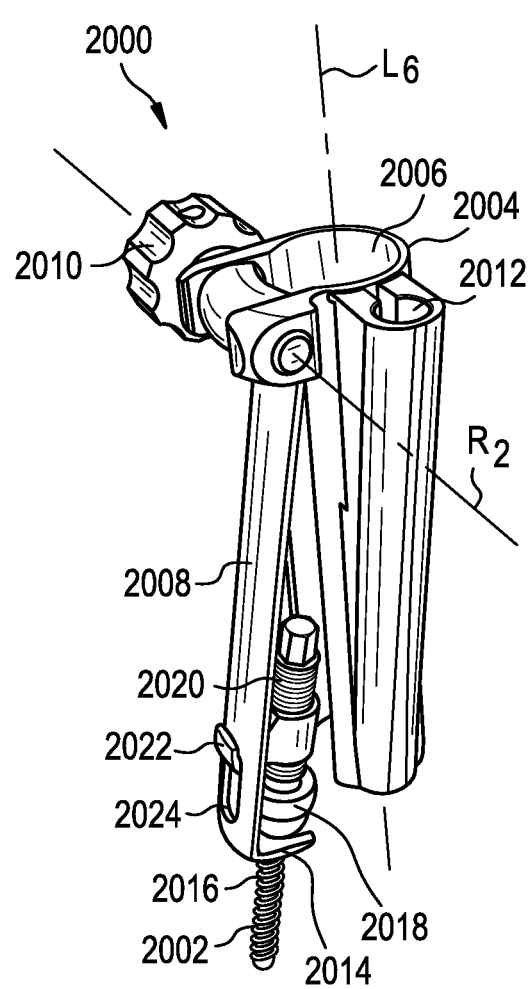
FIG. 20B is an alternative perspective view of one embodiment of an access port coupled to an anchor.

FIGS. 20A and 20B illustrate alternative views of one embodiment of a split-tube access port 2000 that can be coupled to an anchor 2002, such as a pedicle screw. The access port 2000 can include a generally cylindrical body 2004 defining an inner lumen 2006 extending along a longitudinal axis $L_6$ thereof. A linkage portion 2008 of the body 2004 can be split from the remainder and capable of pivoting relative thereto about an axis $R_2$. A thumbscrew 2010 can be included to selectively lock the pivoting motion between the body 2004 and linkage portion 2008. Of course, a cam-lock or any of a variety of other locking mechanisms can also be employed in place of the thumbscrew 2010. In addition to the inner lumen 2006, a secondary lumen 2012 can be provided to receive additional surgical instruments. For example, the secondary lumen 2012 in the illustrated embodiment can be configured to receive a camera and/or light source to aid a user in performing a surgical procedure. The secondary lumen 2012 can extend parallel to the inner lumen 2006 or transversely thereto, and the two lumens can merge in certain embodiments. For example, the secondary lumen 2012 can extend transversely to the inner lumen 2006 such that a light source and/or camera passed through the secondary lumen 2012 extends into the inner lumen 2006 distal to a proximal end of the access port 2000 in some embodiments. In other embodiments, the lumens can remain separate but the secondary lumen 2012 can be angled relative to the inner lumen 2006 such that, e.g., an endoscope camera emerging from a distal end of the secondary lumen 2012 can be viewing a surgical site located beyond a distal end of the inner lumen 2006.

The linkage portion 2008 can couple to the anchor 2002 in any of a variety of manners. For example, in some embodiments, a fork 2014 including a pair of opposed arms can be formed at a distal end of the linkage portion 2008 and configured to receive the anchor 2002 in a recess between the arms. In some embodiments, for example, the arms of the fork 2014 can be configured to receive a narrowed neck or shank portion 2016 of the anchor 2002 that extends distally from a wider proximal head portion 2018. For example, bone anchor portions of polyaxial pedicle screws typically include a cylindrical shank extending from a more spherically-shaped proximal head portion that interfaces with a polyaxial receiver head. By placing the opposed arms of the fork 2014 below the proximal head portion 2018 of the anchor 2002, the linkage portion 2008 can be selectively locked relative to the anchor by applying upward or proximal force to frictionally lock the arms of the fork 2014 against the proximal head 2018 of the anchor 2002.

Such locking force can be applied in a variety of manners. For example, in some embodiments tissue forming incision walls surrounding the anchor 2002 can exert sufficient force against the fork 2014 to prevent relative movement between the fork 2014 and the anchor 2002. Such force might be an inward or compression force exerted by tissue surrounding the anchor 2002, or the fork 2014 can be pulled upward such that a skin surface of the patient is disposed below the fork and exerts an upward force on the fork. As another example, the anchor 2002 can be tightened to compress the fork 2014 between the head portion 2018 of the anchor and a bone surface.

In other embodiments, any of a variety of locking mechanisms can be provided to selectively lock the linkage portion 2008 relative to the anchor 2002. In FIGS. 20A and 20B, for example, a locking screw 2020 can be utilized to drive the linkage portion 2008 upward relative to the anchor 2002. More particularly, a distal end of the locking screw 2020 can be configured to contact a proximal surface of the anchor 2002 and a hook 2022 can be threaded onto the locking screw 2020. The hook 2022 can engage a through-hole 2024 formed in the linkage portion 2008 such that, as the locking screw 2020 is rotated, the hook 2022 translates upward and exerts an upward force on the linkage portion 2008, thereby forcing the fork 2014 into contact with the proximal head 2018 of the anchor 2002. The locking screw 2020 can exert a sufficient force to lock a relative position of the linkage portion 2008 relative to the anchor 2002. In combination with the thumbscrew 2010, a position of the access port 2000 relative to the anchor 2002 can be selectively locked, or movement can be permitted to allow polyaxial movement between these components.

Figure 21:
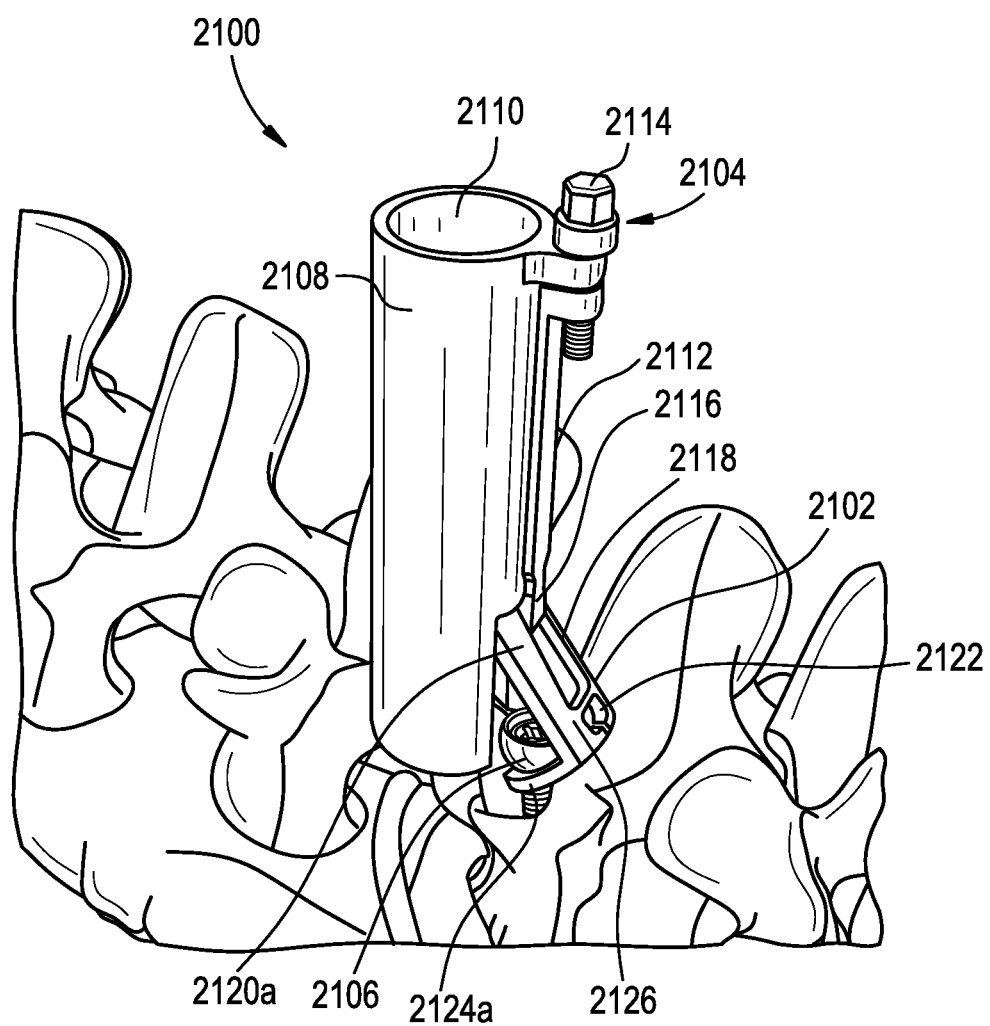
FIG. 21 is a perspective view of one embodiment of an access port coupled to an anchor and configured for selective locking relative thereto.
Figure 22:
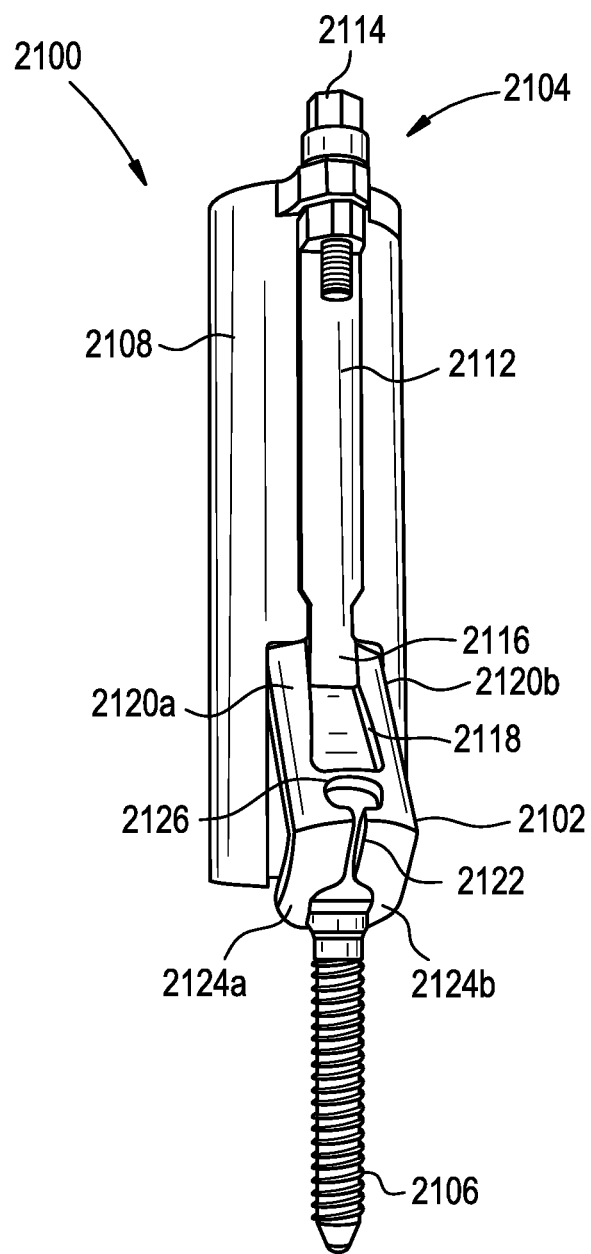
FIG. 22 is a perspective view of the access port and anchor of FIG. 21.

FIGS. 21 and 22 illustrate an alternative embodiment of an access port 2100 with a pivoting linkage portion 2102 and a locking mechanism 2104 to selectively lock a position of the access port relative to an anchor 2106, such as a pedicle or other bone screw. As in the above-described embodiment, the access port 2100 can include a generally cylindrical body 2108 that defines an inner lumen 2110 that can serve as a channel to access a surgical site. The linkage portion 2102 can be pivotably coupled to the body 2108. The locking mechanism 2104 can include an actuator arm 2112 threadingly coupled to a proximal locking screw 2114 at a proximal end thereof. A distal portion of the actuator arm 2112 can include a wedge or dovetail shape 2116 disposed within a tapered slot 2118 formed in a proximal portion of the linkage portion 2102.

To operate the locking mechanism 2104, a user can rotate the locking screw 2114 at a proximal end of the access port 2100. Rotation of the screw 2114 can cause proximal translation of the actuator arm 2112 relative to the body 2108. Proximal movement of the actuator arm 2112 can cause the wedge 2116 to contact sidewalls of the tapered slot 2118 formed in the proximal portion of the linkage portion 2102. This can result in the opposed proximal arms 2120a, 2120b of the linkage portion 2102 being urged laterally outward into contact with sidewalls of the body 2108. Friction between the sidewalls of the body 2108, the proximal arms 2120a, 2120b, and the actuator arm 2112 can lock a position of the linkage portion 2102 relative to the body 2108 of the access port 2000.

Moreover, the linkage portion 2102 can include a slot 2122 formed in a distal portion thereof such that a fork is formed at a distal end of the linkage portion that includes opposed distal arms 2124a, 2124b. The opposed distal arms 2124a, 2124b can be configured to interface with the anchor 2106 in the same manner described above, e.g., around a narrowed shank or neck disposed below a wider proximal anchor head. In such an embodiment, proximal translation of the actuator arm 2112 that urges the proximal arms 2120a, 2120b laterally outward into frictional engagement with the sidewalls of the body 2108 can also cause a corresponding movement of the arms 2124a, 2124b laterally inward, thereby increasing friction of the arms 2124a, 2124b against the anchor 2106. This is because a central portion 2126 of the linkage portion 2102 can serve as a fulcrum about which the two sides of the linkage portion can pivot relative to one another. Accordingly, actuation of the locking screw 2114 can simultaneously lock movement of the linkage portion 2102 relative to the access port body 2108 and the anchor 2106, thereby locking a position of the access port 2000 relative to the anchor.

Other embodiments of locking mechanisms are also possible. For example, in one embodiment a locking mechanism can include an actuator arm driven distally to push against a fork that interfaces with an anchor. Distal advancement of the actuator arm can cause the linkage portion, including the fork, to pivot back towards a center of the access port. This pivoting motion can pinch the screw or anchor head between the fork and an exterior surface of the access tube, thereby locking the tube in place with respect to the screw. In still another embodiment, a hook can be utilized that extends in a plane perpendicular to a longitudinal axis of the access tube. The hook can be attached to a longitudinal screw extending down along a length of the access tube. As the screw is rotated, the hook can rotate about an axis parallel to the longitudinal axis of the access tube. The rotating hook can grab onto the implanted bone anchor and pull it tight to the outside of the access tube to lock the tube in place.

The access ports 2000 and 2100 described above can advantageously transition between a first configuration in which a linkage portion thereof forms a portion of an outer circumference of the access port and a second configuration in which the linkage portion is pivoted or split away from the remainder of the access port body. This can allow the access ports 2000 and 2100 to be inserted in a configuration wherein a longitudinal axis of an inner lumen of the access port is coaxial with a longitudinal axis of an anchor and subsequently moved to a configuration in which a longitudinal axis of an inner lumen of the access port and a longitudinal axis of the anchor are non-coaxial, e.g., as shown in FIGS. 20A-22. Further, the access port can be repeatedly moved between these configurations during a surgical procedure. Thus, the access ports 2000 and 2100 can both define a channel to a surgical site adjacent to an anchor, as well as function as a screw extension providing a channel to the anchor itself, thereby facilitating other procedure steps, including receiver head insertion, spinal fixation element insertion, locking cap insertion, etc.

Figure 23C:
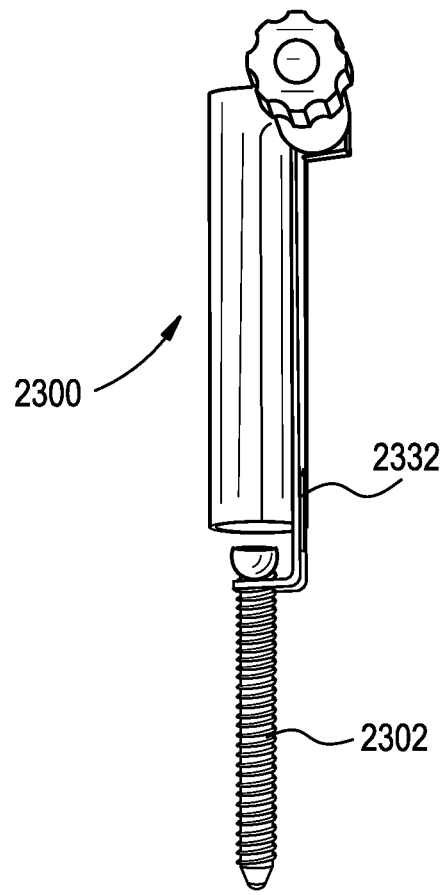
FIG. 23C is a side view of the access port and anchor of FIG. 23A in a second configuration.

FIGS. 23A-23I illustrate one embodiment of a surgical procedure utilizing an access port 2300 similar to that shown in FIGS. 20A and 20B. Similar procedures are also possible utilizing the access port 2100 of FIGS. 21 and 22. As shown in FIG. 23A, a procedure can include implanting a bone screw or other anchor 2302 that is pre-assembled to the access port 2100 in a configuration in which a longitudinal axis $L_7$ of the access port is aligned with a longitudinal axis $L_8$ of the anchor. The components can be maintained in such a position by inserting a dilator and/or driver 2304 through a lumen or channel of the access port 2300 and engaging a proximal end of the anchor 2302. Application of distal force by the driver 2304 to the anchor 2302 can securely restrain a position of the anchor between a distal end of the driver 2304 and a fork 2306 of the access port 2300. In some embodiments, the driver 2304 and fork 2306 can cooperatively restrain the anchor 2302 from axial movement along its longitudinal axis $L_8$, but allow for rotational movement of the driver and anchor relative to the fork during insertion into a patient's bone.

Following percutaneous insertion of the access port 2300 and anchor 2302 utilizing the dilator and/or driver 2304, the driver can be withdrawn proximally out of the access port channel or lumen, thereby leaving the access port coupled to the anchor and positioned in line therewith. In some embodiments, and as described above, the access port fork 2306 can be held against a proximal head 2308 of the anchor 2302 by upward or inward force applied to the fork from tissue surrounding the anchor and access port, or by inserting a locking element, such as the lock screw 2020 and hook 2022 described above in connection with the access port 2000.

In order to provide access to a surgical site, such as intervertebral disc space adjacent to a vertebra in which the anchor 2302 is implanted, a user can angle or otherwise move a portion of the access port 2300, such as the access port body 2310, relative to the anchor to align its channel 2312 with the surgical site. As shown in FIG. 23B, in such a position the longitudinal axis $L_7$ of the access port 2300 can be non-coaxial with the longitudinal axis $L_8$ of the anchor 2302. The access port body 2310 can remain coupled to and stabilized by the anchor 2302 via a linkage portion 2314 that can pivot relative to the body. Further, in some embodiments a lock, such as the thumbwheel lock 2316, can be utilized to selectively lock a position of the linkage portion 2314 relative to the body 2310.

After positioning the access port 2300 as shown in FIG. 23B, a user can perform any of a variety of surgical procedures at the surgical site by introducing one or more instruments through the access port channel 2312. For example, in embodiments wherein the access port is positioned to access intervertebral disc space, a user can perform a spinal fusion cage insertion procedure via the channel 2312 of the access port 2300 while the access port remains secured in position relative to the anchor 2302.

Figure 23D:
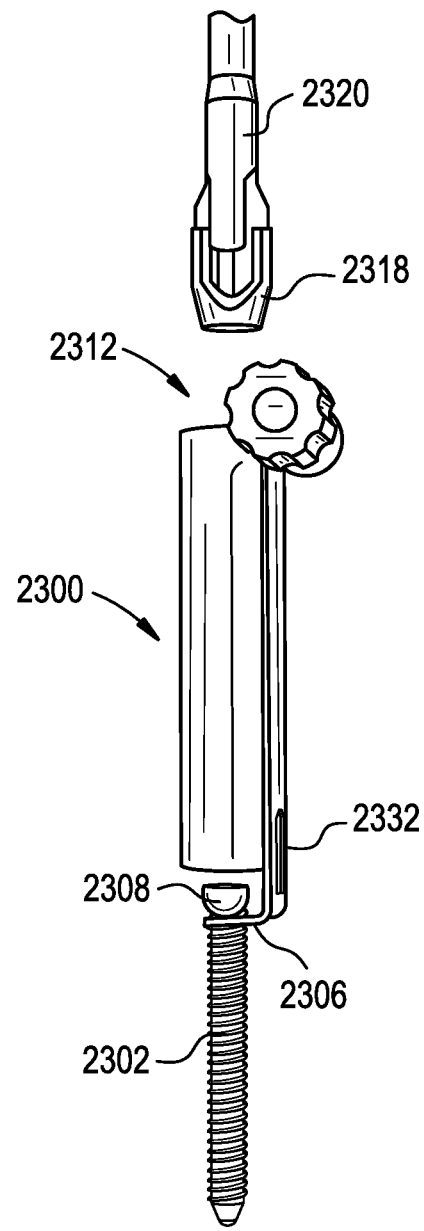
FIG. 23D is a side view of the access port and anchor of FIG. 23A and a receiving member being introduced through the access port.
Figure 23E:
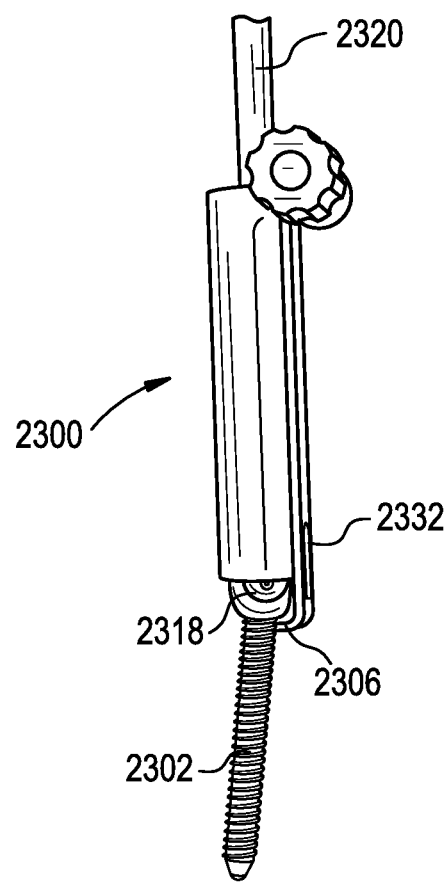
FIG. 23E is a side view of the receiving member of FIG. 23D being coupled to the anchor.

Following completion of intervertebral disc procedures, or any other surgical procedures, any locks (e.g., thumbwheel lock 2316 and/or a fork/anchor lock like the screw 2020 and hook 2022) can be at least partially disengaged and the access port body 2310 can be returned to its insertion position wherein the longitudinal axes $L_7$ and $L_8$ are aligned. Any locks can be reengaged in such a configuration such that the access port 2300 can serve as an anchor extension tower for further surgical procedures, such as receiver head insertion, spinal fixation element insertion, locking cap insertion and tightening, etc. FIG. 23C shows the access port 2300 returned to the configuration of FIG. 23A, but without any dilator and/or driver 2304. FIG. 23D illustrates a polyaxial screw receiver head 2318 being inserted through the channel 2312 of the access port 2300 using a tool 2320. The receiver head 2318 can be advanced distally through the channel 2312 of the access port and coupled to the proximal head 2308 of the anchor 2302. The head 2318 can be coupled to the anchor 2302 without interference from the access port fork 2306 because the fork engages the anchor distal of, or below in the figure, the spherical proximal head 2308 of the anchor (if a locking screw 2020 and hook 2022 are employed, these components may need to be removed before coupling the receiver head 2318 to the anchor 2302). FIG. 23E shows the receiver head 2318 disposed over the proximal head (not visible) of the anchor 2302. Following coupling of the receiver head 2318 and anchor 2302, the insertion tool 2320 utilized to introduce the head through the access port channel 2312 can be removed.

Figure 23F:
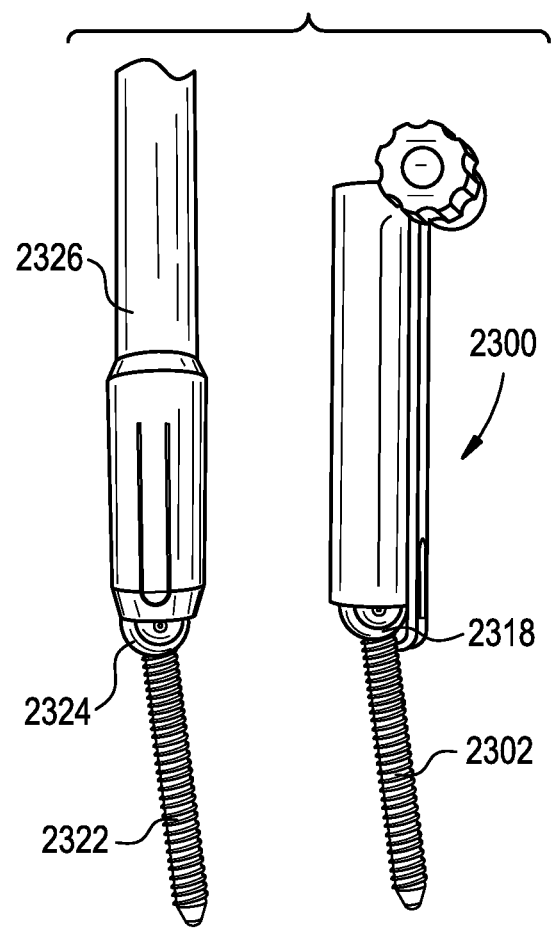
FIG. 23F is a side view of the access port, anchor, and receiving member of FIG. 23E adjacent to a second anchor.
Figure 23G:
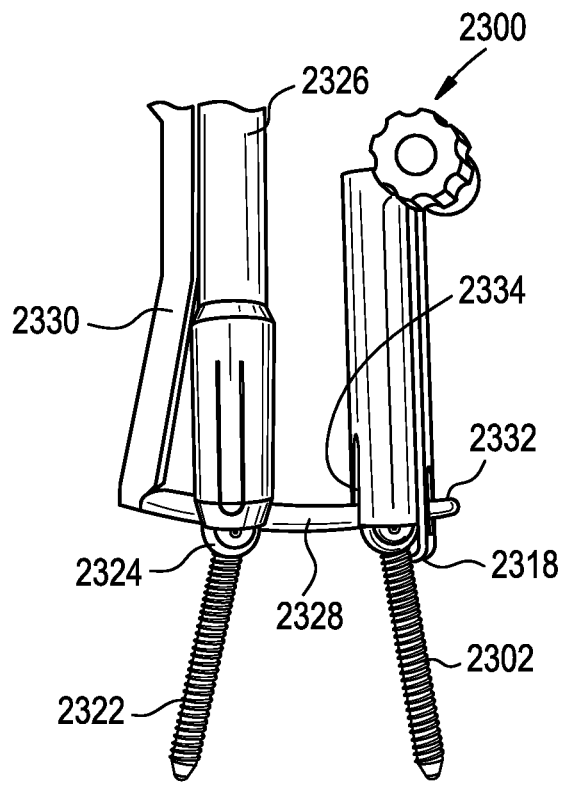
FIG. 23G is a side view of a spinal fixation element being inserted through the receiving member of the anchor and adjacent anchor of FIG. 23F.

FIG. 23F illustrates a further step in which an adjacent anchor 2322 is introduced into a patient's bone, e.g., into an adjacent vertebra on an ipsilateral side of the patient's body. The anchor 2322 can be introduced pre-assembled to a receiver head 2324 and extension tower 2326 that permits manipulation of and access to the anchor 2322 from outside the patient's body. As shown in FIG. 23G, a spinal fixation element, such as a rod 2328, can be passed through the receiver heads 2324 and 2318 using a tool 2330. Note that the extension tower 2326 and access port 2300 can include opposed through-holes formed in sidewalls thereof to allow passage of the rod 2328 or other spinal fixation element. For example, the linkage portion 2314 of the access port 2300 can include a through-hole 2332 that can be utilized for rod passage as well as interfacing with a locking mechanism, such as the above-described locking screw 2020 and hook 2022. The access port body 2310 can also include a through-hole 2334 or slot or other cut-out formed therein that is aligned with the through-hole 2332 to allow the rod 2328 to pass through during insertion. Following rod insertion, a user can introduce locking caps, such as locking caps or set screws 2336 and 2338 shown in FIG. 23I, through the extension tower 2326 and access port channel 2312 to secure the rod 2328 or other spinal fixation element relative to each receiver head/anchor assembly.

Figure 23H:
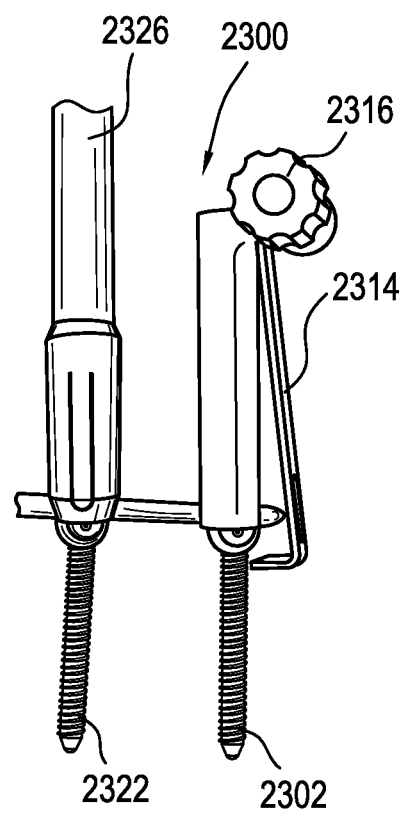
FIG. 23H is an alternative view of the spinal fixation element of FIG. 23G.
Figure 23I:
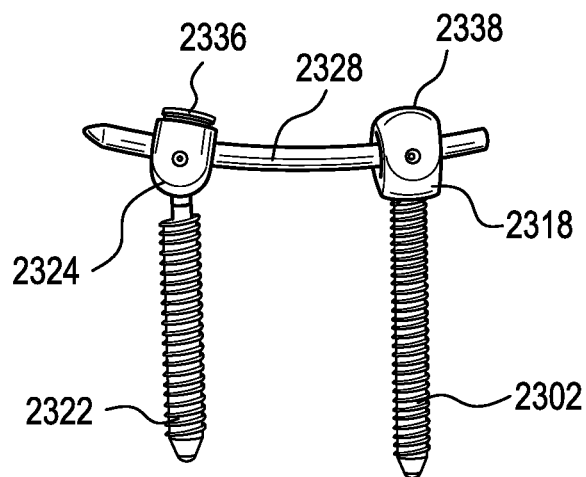
FIG. 23I is a side view of the anchors of FIG. 23H after removal of the access port and adjacent screw extensions.

As shown in FIG. 23H, a further step can include removing the extension tower 2326 and access port 2300 to leave a final in-situ fixation construct, as shown in FIG. 23I. In some embodiments, removal of the access port 2300 can include loosening the thumbwheel lock 2316 to allow the linkage portion 2314 to release from the rod 2328 and anchor 2302.

Figure 24A:
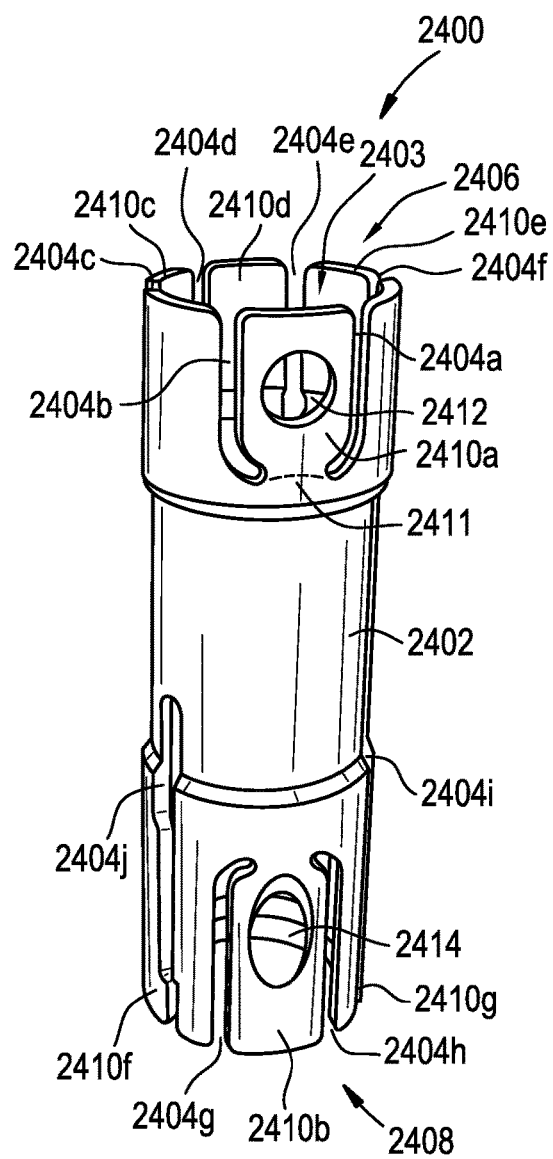
FIG. 24A is a side perspective view of one embodiment of an access port having deformable portions.
Figure 24B:
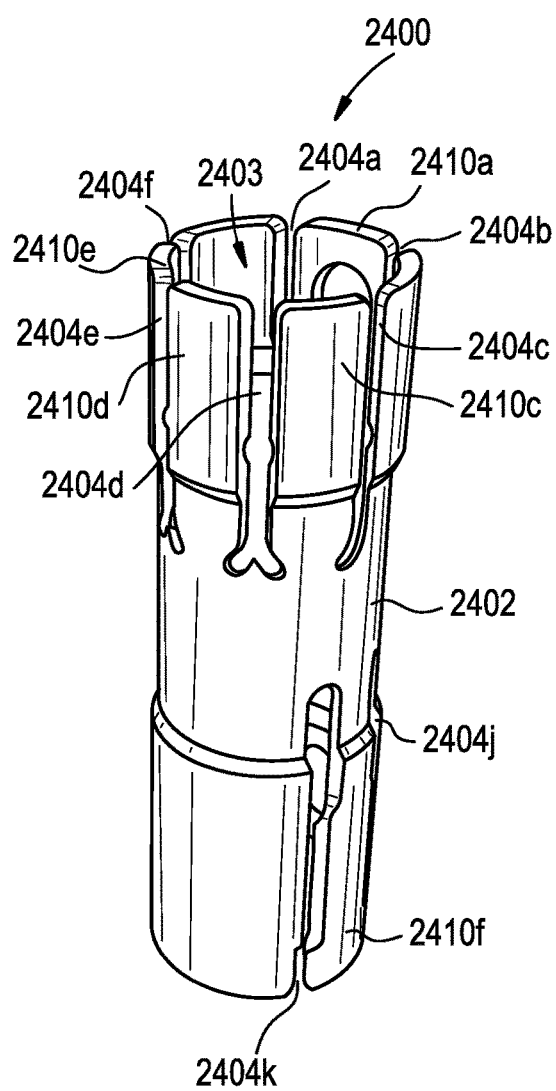
FIG. 24B is a front perspective view of the access port of FIG. 24A.

FIGS. 24A-31D illustrate a further embodiment of an access port that includes one or more malleable or bendable tabs to facilitate use of the access port in procedures like those described above. FIGS. 24A and 24B, for example, illustrate one embodiment of an access port 2400 having a generally cylindrical body 2402 defining an access channel 2403 that can be formed from a malleable material, such as any of a variety of metals and polymers. The body 2402 can include a plurality of slots or slits 2404*a*-2404*k* formed therein and extending axially from any of a proximal end 2406 and a distal end 2408 thereof to form one or more bendable tabs at each end of the access port 2400. For example, the slots 2404*a*-2404*k* illustrated in FIGS. 24A and 24B can form a plurality of tabs 2410*a*-2410*g* that can be deformed or bent away from the illustrated configuration in which they form part of the outer circumference of the cylindrical body 2402. The positioning of the slots or slits 2404*a*-2404*k*, in combination with the material's malleability, can allow for isolated deformation at desired locations, such as the virtual hinge line 2411 of the tab 2404*a* shown in FIG. 24A.

Figure 25:
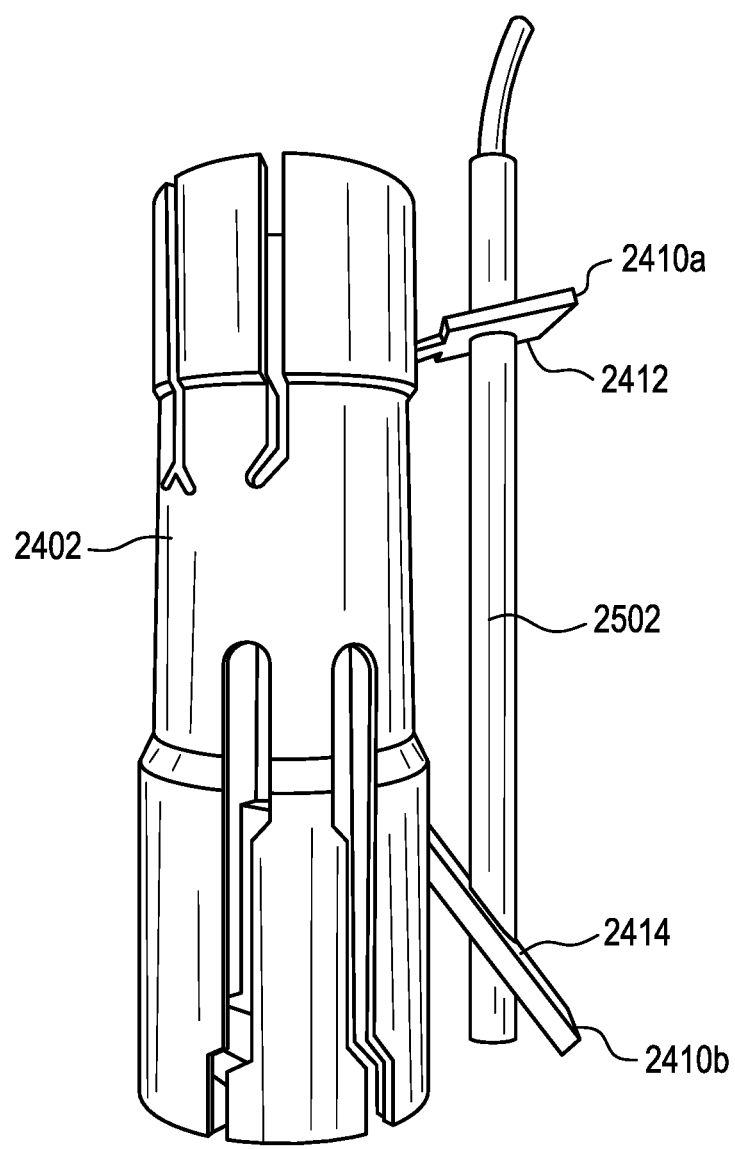
FIG. 25 is a front view of the access port of FIG. 24A receiving a light and/or camera.

The one or more tabs 2410 can serve a variety of purposes in different surgical procedures. For example, in some embodiments corresponding proximal and distal tabs (e.g., tabs 2410*a* and 2410*b*) can include through-holes 2412, 2414, respectively, formed therein to accommodate a surgical visualization system, camera, scope, or light, similar to the secondary lumen 2012 described above in connection with the access port 2000. FIG. 25 illustrates the access port 2400 with a visualization system 2502 disposed through the through-holes 2412, 2414 of the tabs 2410*a*, 2410*b* that have been deformed or bent away from the cylindrical body 2402.

At a distal end 2408 of the access port 2400, a tab 2410*g* can be utilized as a linkage for coupling with an anchor 2602, as shown in FIG. 26. More specifically, the tab 2410*g* can be configured to be coupled to a link 2604 that couples with the anchor 2602. The link 2604, shown in detail in FIG. 27, can include a distal portion with a fork 2606 having opposed arms 2702*a*, 2702*b* configured to engage the anchor 2602 below a proximal head portion thereof. The proximal head portion of the anchor can include a spherical head in the case of an unassembled bone anchor, as described above, or a distal end of a receiver head 2608 in the case of an assembled polyaxial bone screw. A proximal portion of the link 2604 can include a pair of opposed arms 2704*a*, 2704*b* that can be configured to capture the tab 2410*g* to couple the link and the access port body 2402, as shown in FIG. 26.

The link 2604 of the access port 2400 can include features to facilitate securing the link to an anchor 2602, as described above. For example, the link can include a through-hole 2610 formed therein that can receive a hook 2612 that forms part of a locking mechanism, similar to the locking screw 2020 and hook 2022 of FIGS. 20A and 20B. In some embodiments, a locking mechanism may not be employed and upward and/or inward force exerted by surrounding tissue can be relied upon to secure the fork 2606 relative to the anchor 2602.

In use, the access port 2300 can be inserted in the configuration of FIG. 28A, wherein a longitudinal axis $L_9$ of the access port 2300 is aligned with a longitudinal axis $L_{10}$ of the anchor 2602. In some embodiments, a preassembled assembly as shown in FIG. 28A can be inserted using a driver, similar to the embodiment shown in FIG. 23A. In other embodiments, the access port 2400 can be positioned over an implantation site and the anchor 2602 and link 2604 can be implanted by passing them through the central channel or lumen of the access port from a proximal end thereof to a distal end thereof. The link 2604 can then be coupled to a distal portion of the access port 2400 by, e.g., sliding the tab 2410f between the opposed arms 2704a, 2704b of the link, as shown in FIGS. 28A and 28B. In still other embodiments, the anchor 2602 can be implanted independently by passing it through the access port channel or by implanting without the aid of the access port, then the link 2604 can be coupled to the anchor 2602 and the access port 2400. In still other embodiments, the access port 2400 can be inserted down onto the link 2604 that is already coupled to an anchor 2602 implanted in a patient's bone.

In this embodiment, instead of having a locking/unlocking thumbwheel or knob at the top of the access port where the port attaches to the linkage, the access port 2400 can include a bendable tab 2410f or 2410g that allows the port to be moved relative to the anchor 2602 and to then hold the port in place. It is apparent in comparing FIGS. 26-28B that the access port 2400 can include a plurality of distal tabs, such as tabs 2410f and 2410g that are opposed about a midline of the access port 2400, for coupling to a link 2604 in different orientations. Regardless of which tab is utilized, the port 2400 can be placed in a desired position/orientation by bending or deforming the tab and can be maintained there after positioning by the material's inherent rigidity.

As shown in FIGS. 28A and 28B, the access port 2400 can be moved from the above-described axially-aligned configuration of FIG. 28A to a configuration in which the longitudinal axis $L_9$ of the access port is non-coaxial with the longitudinal axis $L_{10}$ of the anchor, as shown in FIG. 28B. Moreover, the access port 2400 can repeatedly be moved between the configurations of FIGS. 28A and 28B to allow for use in a variety of procedures, such as the procedure described above in connection with FIGS. 23A-23I.

The access port 2400 can also be configured to couple to other surgical components, such as a nerve shield or soft tissue retractor 2902. FIG. 29 illustrates a plurality of retractors 2902a, 2902b coupled to the tabs 2410c, 2410d, respectively. FIG. 30 illustrates the retractor 2902 in greater detail. The retractor 2902 can include a proximal handle 3002 for manipulating the retractor and any tab it is coupled to, as well as an elongate body 3004 and a distal retracting tip 3006 configured to shield and/or retract soft tissue. The retractor 2902 can also include a pair of opposed arms 3008a, 3008b for capturing a tab 2410 of the access port 2400, similar to the opposed arms 2704a, 2704b of the above-described link 2604.

Figure 31A:
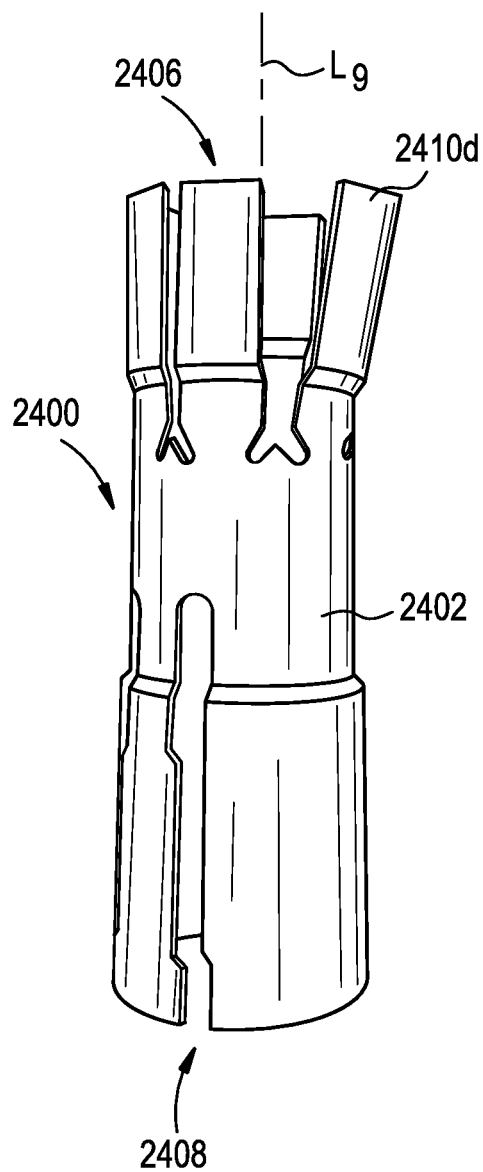
FIG. 31A is a front view of the access port of FIG. 24A prior to coupling to a nerve shield.
Figure 31B:
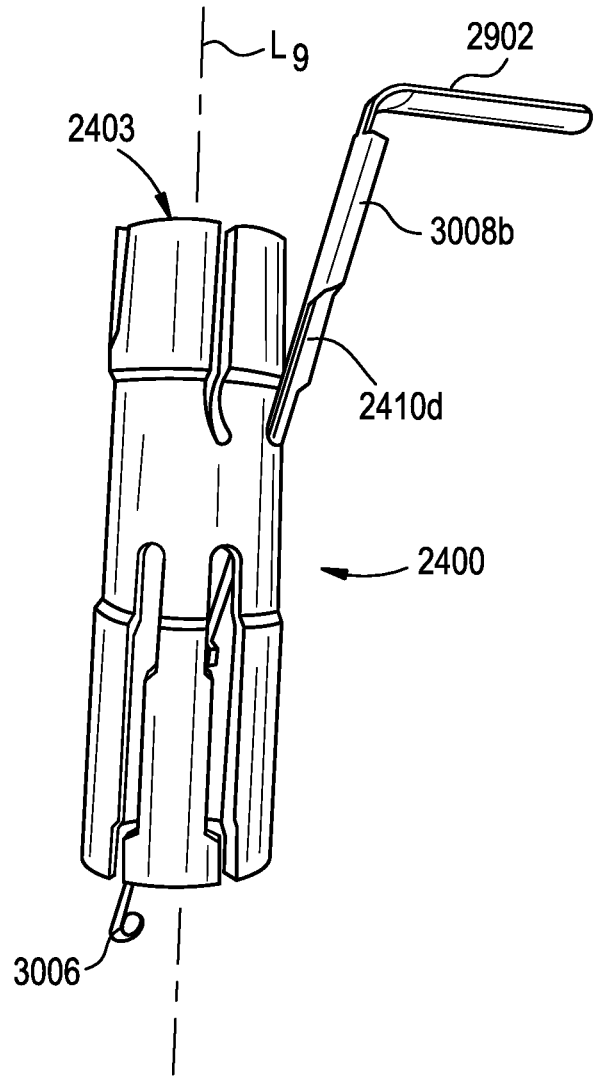
FIG. 31B is a front view of the access port of FIG. 31A after coupling to a nerve shield.

FIGS. 31A-31D illustrate one embodiment of a method for utilizing a soft tissue retractor or nerve shield 2902 in connection with the access port 2400. As shown in FIG. 31A, the method can include deforming or bending a tab 2910d at a proximal end 2406 of the access port 2400 away from a central longitudinal axis $L_9$ such that the tab splits away from an initial configuration in which it forms part of the outer circumference of the cylindrical body 2402 of the access port. The soft tissue retractor 2902 can then be introduced into the channel or lumen 2403 of the access port 2400 in a manner that engages the tab 2410d and the opposed arms 3008a, 3008b of the retractor 2902, as shown by FIGS. 31B and 31C. In so doing, the distal retracting tip 3006 can cross the longitudinal axis $L_9$ or a midline of the channel 2403 to protrude from a distal end 2408 of the access port on an opposite side of the port from the tab 2410d. After completing distal advancement of the retractor 2902, a user can utilize the handle 3002 to bend or deform the tab 2910d back to its original position aligned with an outer circumference of the access port cylindrical body 2402, as shown in FIG. 31D. As the tab is moved, the distal retractor tip 3006 can move back across the access tube longitudinal axis $L_9$ or midline such that the tip is positioned on a same side as the tab 2910d. As it moves, the retractor tip can capture and move any soft tissue it encounters, such as nerves, etc. Such a retractor 2902 can be useful in moving, for example, nerves commonly encountered during surgical procedures on a patient's vertebrae. As shown in FIG. 29, in some embodiments a plurality of retractors can be employed simultaneously. For example, the proximal end 2406 of the access port 2400 can include four slits or slots 2404c-2404f that create three identical tabs 2410c-2410e to which a retractor 2902 can be coupled.

In another embodiment, a method for utilizing the access port 2400 can include deforming proximal and distal tabs 2410a, 2410b and positioning an endoscope or surgical visualization system 2502 through holes 2412, 2414 formed in the tabs 2410a, 2410b. The access port 2400 and endoscope or other visualization system 2502 can be introduced into a patient with a pedicle screw or other anchor 2602 (the screw can be preassembled with any of a variety of receiver heads, e.g., polyaxial, monoaxial, favored angle, etc., or can be headless). For introduction into the patient's body, the port 2400 can be aligned with the anchor 2602 such that a longitudinal axis of the port 2400 and a longitudinal axis of the anchor 2602 are aligned. Introduction and insertion can be facilitated by inserting a dilator and/or driver tool through a working channel of the access port 2400 such that it interfaces with the anchor 2602. Following introduction and insertion of the anchor 2602 into a patient's bone, any dilator or driver tool can be removed and the port 2400 can be manipulated into a desired position, e.g., over intervertebral disc space adjacent to the vertebra into which the anchor 2602 was inserted, by deforming whichever tab 2410f, 2410g is coupled to the anchor by the link 2604. In some embodiments, the desired position can be on an ipsilateral side of the patient's body (e.g., adjacent to the anchor 2602 on a same side of a patient's spine or midline axis). When in the desired position, a longitudinal axis of the access port 2400 can be non-coaxial with a longitudinal axis of the anchor. In some embodiments, a position of the link 2604 and port 2400 can be locked relative to the anchor 2602 using, for example, a locking screw and hook 2612 to drive the distal fork 2606 of the link 2604 upward against a proximal portion of the anchor.

The method can further include deforming one or more of the proximal tabs 2410c, 2410d, 2410e outward away from a central longitudinal axis of the access port. A retractor 2902 can be coupled to a deformed tab 2410 and advanced distally beyond a distal end of the port 2400 where, for example, soft tissue creep may have occurred. A distal retractor tip 3006 of the retractor 2902 can be positioned on an opposite side of the soft tissue from the deformed tab 2910 that is coupled to a proximal portion of the retractor. The retractor can then be manipulated in a manner that deforms the tab coupled thereto back to an original position. This movement can cause the distal retractor tip 3006 to capture the soft tissue and retract it towards the side of the access port 2400 where the tab 2410 couples to the retractor 2902, thereby clearing a central portion of the access tube lumen 2403. The retractor 2902 and captured tissue can be maintained in this position because force exerted by the captured tissue can be less than a force required to cause the tab 2410 to deform.

A user can complete any of a variety of surgical procedures through the lumen 2403 of the access port 2400. For example, procedures on the intervertebral disc space, such as disc replacement, discectomy, endplate preparation, fusion cage insertion, bone graft delivery, and the like can be performed by passing instruments or implants through the access port 2400. Once complete, any locking relative to the anchor 2602 can be released and any tissue retractor 2902 removed, if present, and whichever tab 2410f, 2410g is coupled to the link 2604 can be deformed back to its original position, thereby returning the access port 2400 to its insertion configuration wherein a longitudinal axis of the access port is aligned with a longitudinal axis of the anchor. The access port 2400 can continue to act as a screw tower over the anchor 2602 to aid in anchor receiver head insertion and coupling, spinal fixation element insertion, as well as locking cap insertion and tightening, as described above in connection with FIGS. 23A-23I. When all operations are complete, the link 2604 can be disengaged from the anchor 2602 and the port 2400 can be removed.

Figure 32:
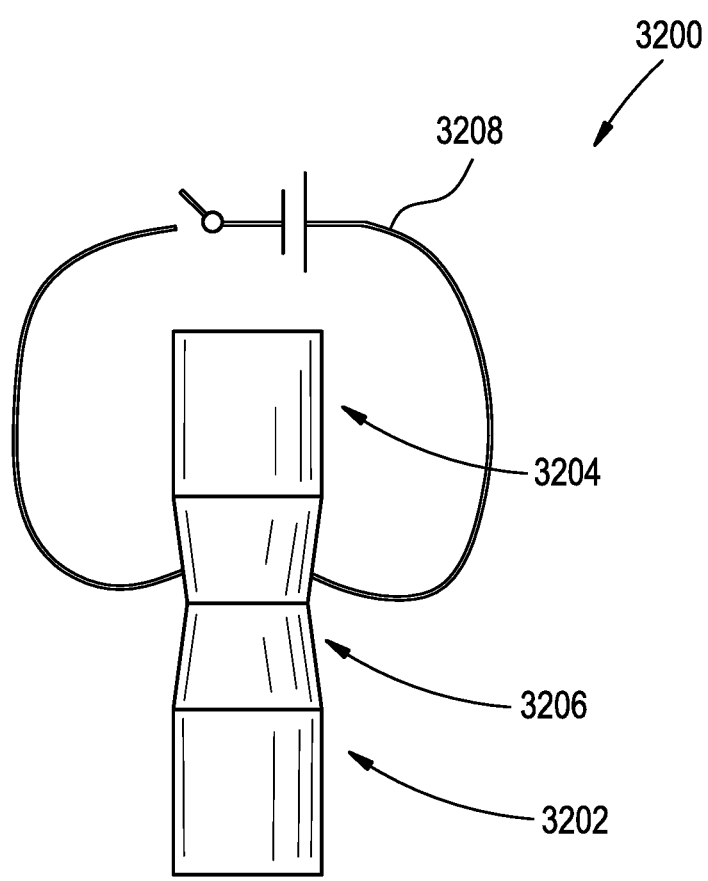
FIG. 32 is a schematic of a selectively deformable linkage between an anchor and an access port.

FIG. 32 illustrates still another embodiment of a linkage 3200 to couple an access port and an anchor in a selectively lockable manner. A distal portion 3202 of the linkage 3200 can be configured to couple to an anchor, such as a pedicle screw. The coupling can be achieved using a variety of known mechanisms, including a threaded engagement, interfacing with one or more notches or other mating features formed on an anchor, etc. Similarly, a proximal portion 3204 of the linkage 3200 can be configured to couple to an access port using any of a variety of known mechanisms. The proximal portion 3202 and distal portion 3204 can be coupled to one another by a "smart" material 3206 having mechanical properties that can be varied by application of electrical current or other input. For example, the material 3206 can be normally free to move and flex, but can be made rigid by applying an electric current 3208 or other input thereto. Alternatively, the material 3206 can be reversed such that it is normally rigid and made flexible by application of an electric current or other input.

In such an embodiment, an access port can be positioned relative to a bone screw or other anchor as desired, then current or other input can be applied to the smart material 3206 to hold it in place. The configuration of FIG. 32 is one example of how such a material can be utilized, but it is possible to employ it in a variety of manners in connection with the systems and devices described herein. For example, such materials could be utilized to achieve clamping of extension tabs, such as the tabs described in connection with FIGS. 4-12C above. Such materials could also be utilized to clamp a connector onto a screw tower or port, etc.

One example of such a "smart" material 3206 can be electroplastic elastomer hydrogels, which can exhibit altered tensile strength (e.g., from flexible to hard) based on electric current applied thereto. Other exemplary materials can include electroactive polymers (EAP), nitinol or shape memory materials, hydrogels, etc.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The instruments disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the instruments disclosed herein can have varying degrees of rigidity or flexibility, as appropriate for their use. Device sizes can also vary greatly, depending on the intended use and surgical site anatomy. Furthermore, particular components can be formed from a different material than other components. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of spinal surgery on a human patient, it will be appreciated that the methods and devices disclosed herein can be used in any of a variety of surgical procedures with any human or animal subject, or in non-surgical procedures.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

One skilled in the art will appreciate further features and advantages based on the above-described embodiments.

Accordingly, the disclosure is not to be limited by what has been particularly shown and described. All publications and references cited herein are expressly incorporated herein by reference in their entirety.

What is claimed is:

1. A surgical system, comprising:
   an access port configured for percutaneous insertion into a patient to define a channel to a surgical site;
   an extension tower configured to couple to an implant in the spine of a patient; and
   a linkage having a first connection to receive the access port, a second connection to receive to the extension tower, and a plurality of rigid segments extending therebetween, wherein the linkage is selectively lockable to lock a position of the access port relative to the extension tower,
   wherein the plurality of rigid segments of the linkage includes a first pair of segments pivotably coupled to a second pair of segments, the segments in each of the first pair of segments and the second pair of segments being positioned such that an axis drawn transverse to a longitudinal axis of a first segment in the first pair of segments or the second pair of segments and a longitudinal axis of a second segment in the first pair of segments or the second pair of segments passes through both the first segment and the second segment of the first pair of segments or the second pair of segments.

2. The system of claim 1, wherein the first pair of segments includes the first connection at a distal end thereof and the second pair of segments includes the second connection at a distal end thereof.

3. The system of claim 1, wherein the first connection is configured to lock to the access port and the second connection is configured to lock to the extension tower independently of one another.

4. The system of claim 1, wherein the first connection is configured to removably receive the access port and the second connection is configured to removably receive the extension tower.

5. The system of claim 1, further comprising an extension post extending from a sidewall of the access port, the linkage being configured to couple to the extension post for forming the first connection.

6. The system of claim 1, wherein a longitudinal axis of the access port is non-coaxial with a longitudinal axis of the extension tower.

7. The system of claim 1, wherein a longitudinal axis of the access port is obliquely angled with respect to a longitudinal axis of the extension tower.

8. The system of claim 1, wherein the access port further comprises a secondary lumen configured to receive one or more instruments therethrough, the secondary lumen extending substantially parallel to the channel through a length of the access port.

9. The system of claim 8, wherein the secondary lumen merges with the channel across a portion of the access port.

10. The system of claim 8, wherein the secondary lumen is configured to receive a camera or a light source therethrough to aid a user in performing a surgical procedure.

11. The system of claim 10, wherein the camera is configured to pass out of a distal end of the secondary lumen to view a surgical site located beyond a distal end of the channel.

12. The system of claim 1, further comprising a knob disposed in the linkage to lock the position of the access port relative to the extension tower.

13. The system of claim 1, wherein the linkage is configured to pivot relative to the access port.

14. The system of claim 1, wherein the linkage is coupled to the extension tower via a sleeve disposed about an outer circumference of the extension tower.

15. The system of claim 14, wherein the sleeve further comprises a cam lever to selectively lock the sleeve to the extension tower.

16. The system of claim 1, wherein the access port is unitary.

17. The system of claim 1, wherein the access port further comprises at least one tab extending proximally therefrom.

18. The system of claim 17, wherein the at least one tab further comprises at least one opening configured to receive at least a portion of an instrument passing through the access port therethrough.

* * * * *